US010273303B2

(12) United States Patent
Ng et al.

(10) Patent No.: US 10,273,303 B2
(45) **Date of Patent: *Apr. 30, 2019**

(54) MONOVALENT ANTIGEN BINDING CONSTRUCTS TARGETING EGFR AND/OR HER2 AND USES THEREOF

(71) Applicant: Zymeworks Inc., Vancouver (CA)

(72) Inventors: Gordon Yiu Kon Ng, Vancouver (CA); Peter Wing Yiu Chan, Richmond (CA); Grant Raymond Wickman, Vancouver (CA)

(73) Assignee: Zymeworks Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/036,174

(22) PCT Filed: Nov. 13, 2014

(86) PCT No.: PCT/US2014/065546

§ 371 (c)(1),
(2) Date: May 12, 2016

(87) PCT Pub. No.: WO2015/073721

PCT Pub. Date: May 21, 2015

(65) Prior Publication Data

US 2016/0289328 A1 Oct. 6, 2016

Related U.S. Application Data

(60) Provisional application No. 61/903,825, filed on Nov. 13, 2013.

(51) Int. Cl.

| | |
|---|---|
| ***A61K 39/395*** | (2006.01) |
| ***C07K 16/28*** | (2006.01) |
| ***C07K 16/32*** | (2006.01) |
| ***A61K 47/68*** | (2017.01) |
| *A61K 39/00* | (2006.01) |

(52) U.S. Cl.

CPC ...... *C07K 16/2863* (2013.01); *A61K 47/6803* (2017.08); *A61K 47/6849* (2017.08); *A61K 47/6851* (2017.08); *C07K 16/32* (2013.01); *A61K 2039/505* (2013.01); *A61K 2039/507* (2013.01); *C07K 2317/35* (2013.01); *C07K 2317/41* (2013.01); *C07K 2317/52* (2013.01); *C07K 2317/55* (2013.01); *C07K 2317/569* (2013.01); *C07K 2317/64* (2013.01); *C07K 2317/72* (2013.01); *C07K 2317/73* (2013.01); *C07K 2317/732* (2013.01); *C07K 2317/76* (2013.01); *C07K 2317/77* (2013.01); *C07K 2317/92* (2013.01)

(58) Field of Classification Search

CPC ................................................ A61K 2039/505

See application file for complete search history.

(56) References Cited

U.S. PATENT DOCUMENTS

| | | | | |
|---|---|---|---|---|
| 6,737,056 | B1 | 5/2004 | Presta | |
| 7,642,228 | B2 | 1/2010 | Carter et al. | |
| 7,678,890 | B2 | 3/2010 | Bosch et al. | |
| 7,951,917 | B1 | 5/2011 | Arathoon et al. | |
| 8,592,562 | B2 | 11/2013 | Kannan et al. | |
| 9,493,578 | B2 * | 11/2016 | Lazar | A61K 47/48507 |
| 9,562,109 | B2 * | 2/2017 | Von Kreudenstein | C07K 16/00 |
| 2004/0110226 | A1 | 6/2004 | Lazar et al. | |
| 2006/0074225 | A1 | 4/2006 | Chamberlain et al. | |
| 2007/0105199 | A1 * | 5/2007 | Yan | C07K 16/00 435/69.7 |
| 2009/0148905 | A1 | 6/2009 | Ashman et al. | |
| 2009/0214541 | A1 | 8/2009 | Gillies et al. | |
| 2012/0149876 | A1 | 6/2012 | Von Kreudenstein et al. | |
| 2012/0244578 | A1 | 9/2012 | Kannan et al. | |
| 2013/0156796 | A1 | 6/2013 | Setiadi et al. | |
| 2014/0105889 | A1 | 4/2014 | Igawa et al. | |
| 2014/0154253 | A1 * | 6/2014 | Ng | C07K 16/2803 424/136.1 |

(Continued)

FOREIGN PATENT DOCUMENTS

| | | | |
|---|---|---|---|
| WO | WO 2004/032961 | 4/2004 | |
| WO | WO 2011/117330 | 9/2011 | |
| WO | WO-2012058768 A1 * | 5/2012 | C07K 16/00 |

(Continued)

OTHER PUBLICATIONS

Merchant et al., Monovalent antibody design and mechanism of action of onartuzumab, a MET antagonist with anti-tumor activity as a therapeutic agent PNAS, 110(32):E2987-E2996, publisehd online URL:<http://www.pnas.org/content/110/32/E2987>, E2987-2996, Jul. 23, 2013.*

Sridhar et al., Inhibition of epidermal-growth-factor receptors: a review of clinical research focusing on non-small-cell lung cancer, Lancet Oncol., 4(7): 397-406, Jul. 2003.*

Junttila et al., Superior in vivo efficacy of afucosylated trastuzumab in the treatment of HER2-amplified breast cancer, Canc. Res. 70(11):4481-9, 2010.*

Lamminmaki et al., Crystal structure of a recombinant anti-estadiol Fab fragment in complex with 17B-Estradiol, J. Biol. Chem. 276:36687, 2001.*

(Continued)

*Primary Examiner* — Prema M Mertz

(74) *Attorney, Agent, or Firm* — Fenwick & West LLP

(57) ABSTRACT

Provided herein are monovalent antigen-binding constructs targeting EGFR and/or HER2. The monovalent antigen-binding constructs can include at least one antigen-binding polypeptide comprising a heavy chain variable domain, wherein the antigen-bind polypeptide specifically binds EGFR and/or HER2; and a heterodimeric Fc domain, the Fc domain comprising at least two CH3 domains, wherein the Fc domain is coupled, with or without a linker, to the antigen-binding polypeptide. Also provided are methods of making the constructs and methods of using the constructs.

21 Claims, 21 Drawing Sheets

Specification includes a Sequence Listing.

(56) References Cited

U.S. PATENT DOCUMENTS

2014/0199294 A1 7/2014 Mimoto et al.
2015/0307628 A1* 10/2015 Kim ....................... C07K 16/00
530/387.3

FOREIGN PATENT DOCUMENTS

WO WO 2013/026837 2/2013
WO WO 2013/033008 3/2013
WO WO-2013063702 A1 * 5/2013 ............ C07K 16/46
WO WO 2013/166594 11/2013
WO WO-2013166604 A1 * 11/2013 ............ C07K 16/32

OTHER PUBLICATIONS

MacCallum et al., Antibody-antigen interactions: contact analysis and binding site topograpy, J. Mol. Biol 262:732, 1996.*
Phillips et al., Targeting HER2-positive breast cancer with trastuzumab-DM1, an antibody-cytotoxic drug conjugate, Canc. Res. 68(22):9280-9290, Nov. 2008.*
Carter, P. , From knobs-into-Holes to Onartuzumab (MetMAb), Prot. Sci., 21(Suppl 1):57-58, abstract 16, Aug. 2012.*
Janeway et al., Immunobiology: The structure of a typical antibody molecule, In: The Immune System in Health and Disease. 5th edition. New York: Garland Science; 2001. [Retrieved online from: <URL: https://www.ncbi.nlm.nih.gov/books/NBK27144/>. {Retrieved on Jun. 27, 2018].*
Ferguson, K.M., Structure-based view of epidermal growth factor receptor regulation, Ann. Rev. Biophys. 37:353-373, 2008.*
Boland, W.K., et al., "Nimotuzumab: a novel anti-EGFR monoclonal antibody that retains anti-EGFR activity while minimizing skin toxicity," Expert Opin. Boil. Ther., vol. 9, No. 9, pp. 1199-1206, Sep. 2009.
Derer, S., et al., "Impact of Epidermal Growth Factor Receptor (EGFR) Cell Surface Expression Levels on Effector Mechanisms of EGFR Antibodies," The Journal of Immunology, pp. 1-10, Oct. 24, 2012.
Junghans, R.P., "Cruel antibody fictions! Cellular antigen enumeration by 'saturation' binding," Immunology Today, vol. 20, No. 9, pp. 401-406, Sep. 1999.
Patent Cooperation Treaty, International Search Report and Written Opinion of the International Searching Authority, International Patent Application No. PCT/US2014065546, dated Apr. 6, 2015, 17 Pages.
Bell, A., et al., Differential tumor-targeting abilities of three single-domain antibody formats. Cancer Letters, 2010; 289: 81-90.
Gaborit, N., et al., Time-resolved Fluorescence Resonance Energy Transfer (TR-FRET) to Analyze the Disruption of EGFR/HER2 Dimers: A New Method to Evaluate the Efficiency of Targeted Therapy using Monoclonal Antibodies. J. Biol. Chem., Apr. 2011; 286(13): 11337-11345.
Gerdes, C. A., et al., GA201 (RG7160): a novel, humanized, glycoengineered anti-EGFR antibody with enhanced ADCC and superior in vivo efficacy compared with cetuximab. Clin Cancer Res, (2013), 19:5; 1126-1138.
Kelton, C., et al., Anti-EGFR biparatopic-SEED antibody has enhanced combination-activity in single molecule. Arch Biochem Biophys, 2012; 526(2): 219-225.
Larbouret, C., et al., In pancreatic carcinoma, dual EGFR/HER2 targeting with cetuximab/trastuzumab is more effective than treatment with trastuzumab/erlotinib or lapatinib alone: implication of receptors' down-regulation and dimers' disruption. Neoplasia, Feb. 2012; 14(2): 121-130.
Martinelli, E., et al., Anti-epidermal growth factor receptor monoclonal antibodies in cancer therapy. Clin Exp Immunol., Oct. 2009; 158(1): 1-9.
Melosky, B., et al., Management of skin rash during EGRF-targeted monoclonal antibody treatment for gastrointestinal malignancies: Canadian recommendations. Curr Oncol, Jan. 2009; 16(1): 16-26.
Mendelsohn, J., and Baselga, J., The EGF receptor family as targets for cancer therapy. Oncogene, Dec. 2000; 19(56): 6550-6565.
Muda, M., et al., Therapeutic assessment of SEED: a new engineered antibody platform designed to generate mono- and specific antibodies. Protein Engineering, Design & Selection (2011); 24(5): 447-454.
Pirker, R., et al., EGFR expression as a predictor of survival for first-line chemotherapy plus cetuximab in patients with advanced non-small-cell lung cancer: analysis of data from the phase 3 FLEX study. Lancet Oncol., Jan. 2012; 13(1): 33-42.
Roovers, R.C., et al., A biparatopic anti-EGFR nanobody efficiently inhibits solid tumour growth. Int J Cancer, Oct. 2011; 129(8): 2013-2024.
Rüschoff, J., et al., Reproducibility of immunohistochemical scoring for epidermal growth factor receptor expression in non-small cell lung cancer: round robin test. Arch Pathol Lab Med., Sep. 2013; 137(9): 1255-1261.
Vitetta, E.S., et al., "Considering Therapeutic Antibodies." Science, Jul. 21, 2006, vol. 313, pp. 308-309.
Zhou, X., et al., In vitro and in vivo anti-tumor activities of anti-EGFR single-chain variable fragment fused with recombinant gelonin toxin. J Cancer Res Clin Oncol (2012) 138:7; 1081-1090.
Zhou, Y., et al., Impact of intrinsic affinity on functional binding and biological activity of EGFR antibodies. Mol Cancer Ther., Jul. 2012; 11(7): 1467-1476.
U.S. Appl. No. 13/289,934—Restriction Requirement dated Sep. 16, 2014.
U.S. Appl. No. 13/289,934—Non-Final Office Action dated Feb. 27, 2015, 15 pages.
U.S. Appl. No. 13/289,934—Final Office Action dated Nov. 16, 2015, 19 pages.
U.S. Appl. No. 13/289,934—Advisory Action dated Feb. 5, 2016, 8 pages.
U.S. Appl. No. 13/289,934—Notice of Allowance dated Apr. 25, 2016, 9 pages.
U.S. Appl. No. 13/289,934—Notice of Allowance dated Sep. 29, 2016, 9 pages.
U.S. Appl. No. 13/892,198—Restriction Requirement dated Jul. 10, 2015, 12 pages.
U.S. Appl. No. 13/892,198—Non-Final Office Action dated Oct. 6, 2015, 23 pages.
U.S. Appl. No. 14/989,648—Restriction Requirement dated Jan. 9, 2018, 6 pages.
U.S. Appl. No. 13/927,065—Restriction Requirement dated Apr. 15, 2015, 9 pages.
U.S. Appl. No. 13/927,065—Non-Final Office Action dated Oct. 7, 2015, 10 pages.
U.S. Appl. No. 13/927,065—Final Office Action dated Feb. 22, 2016, 6 pages.
U.S. Appl. No. 13/927,065—Notice of Allowance dated Aug. 26, 2016, 7 pages.
U.S. Appl. No. 15/355,019—Non-Final Office Action dated Jul. 21, 2017, 7 pages.
U.S. Appl. No. 15/355,019—Notice of Allowance dated Nov. 17, 2017, 8 pages.
U.S. Appl. No. 13/668,098—Restriction Requirement dated Dec. 5, 2014, 10 pages.
U.S. Appl. No. 13/668,098—Non-Final Office Action dated Apr. 3, 2015, 18 pages.
U.S. Appl. No. 13/668,098—Final Office Action dated Nov. 17, 2015. 16 pages.
U.S. Appl. No. 13/668,098—Notice of Allowance dated Sep. 23, 2016, 12 pages.
U.S. Appl. No. 13/638,362—Restriction Requirement dated Jan. 29, 2015, 9 pages.
U.S. Appl. No. 13/638,362—Non-Final Office Action dated May 26, 2015, 12 pages.
U.S. Appl. No. 13/638,362—Notice of Allowance dated Dec. 18, 2015, 10 pages.
U.S. Appl. No. 15/046,379—Restriction Requirement dated Feb. 8, 2018, 6 pages.
U.S. Appl. No. 14/893,503—Restriction Requirement dated Dec. 28, 2017, 7 pages.

(56) References Cited

OTHER PUBLICATIONS

U.S. Appl. No. 14/893,503—Non-Final Office Action dated Mar. 30, 2018, 16 pages.

* cited by examiner

A
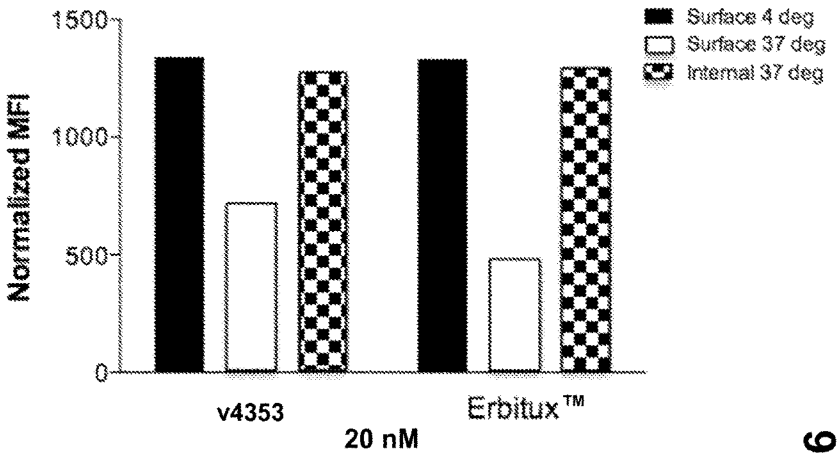
FIG. 6
B
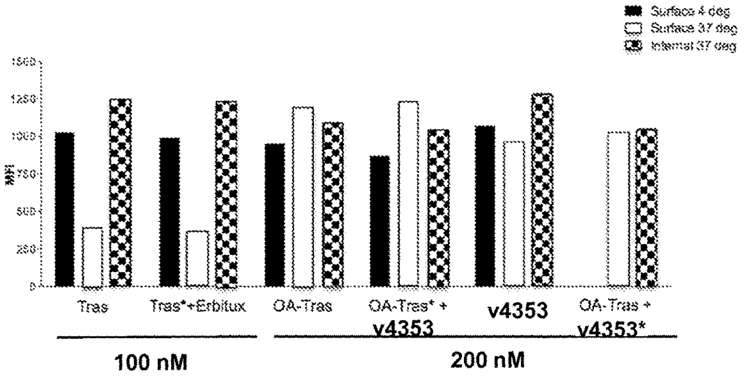

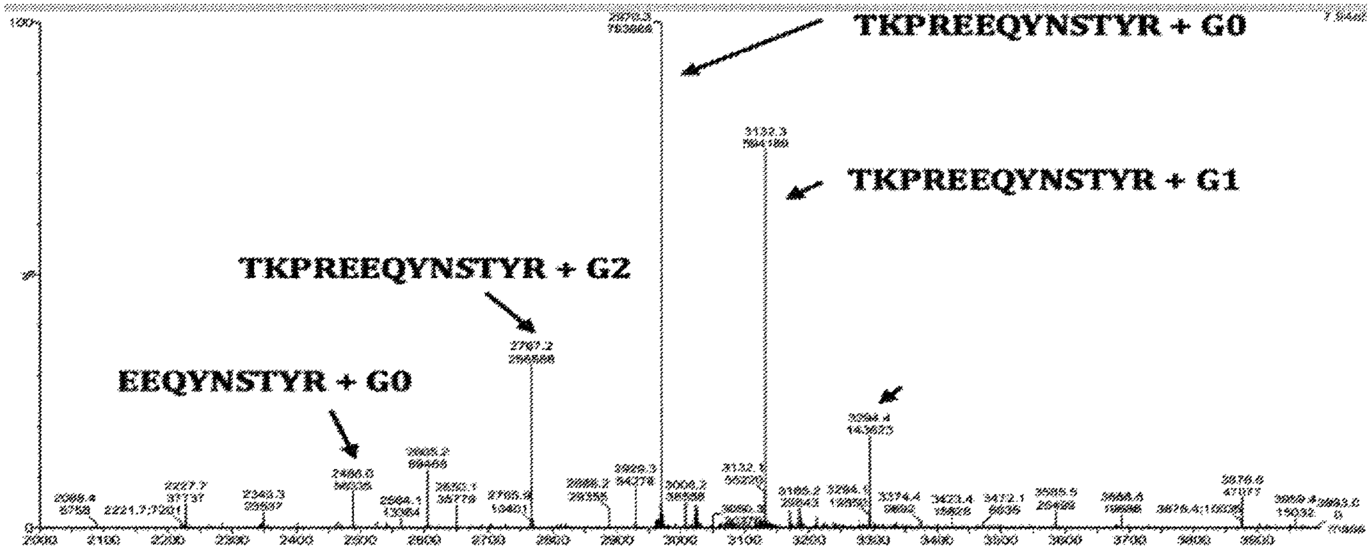

| Glycopeptide Mass (Da) | Peptide | Glycan Composition | Glycan i.d. | Rel. int. (%) in 4353-363-Afuco |
|---|---|---|---|---|
| 2605.15 | TKPREEQYNSTYR | HexNAc Hex | | 4.10 |
| 2227.7 | EEQYNSTYR | HexNAc3Hex2Fuc | | 1.73 |
| 2767.21 | TKPREEQYNSTYR | HexNAc Hex | | 11.75 |
| 2888.2 | TKPREEQYNSTYR | HexNAc Hex | | 1.34 |
| 3374.4 | TKPREEQYNSTYR | HexNAc Hex | | 0.44 |
| 2929.26 | TKPREEQYNSTYR | HexNAc Hex | | 2.94 |
| 2487.99 | EEQYNSTYR | HexNAc Hex | G0 | 2.58 |
| 2970.29 | TKPREEQYNSTYR | HexNAc Hex | G0 | 36.34 |
| 2650.04 | EEQYNSTYR | HexNAc Hex | G1 | 1.64 |
| 3132.34 | TKPREEQYNSTYR | HexNAc Hex | G1 | 27.20 |
| 3294.39 | TKPREEQYNSTYR | HexNAc Hex | G2 | 6.57 |
| 3423.3 | TKPREEQYNSTYR | HexNAc Hex SA | G1N | 0.00 |
| 3585.4 | TKPREEQYNSTYR | HexNAc Hex SA | G2N | 1.21 |

FIG. 11

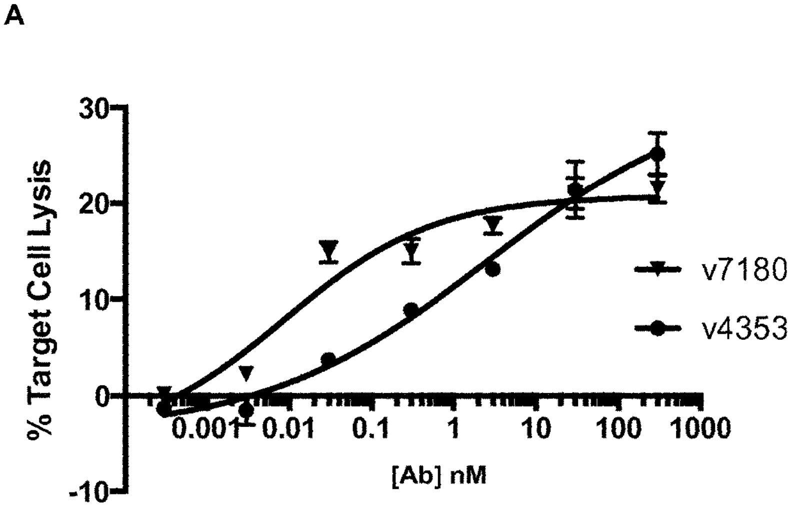
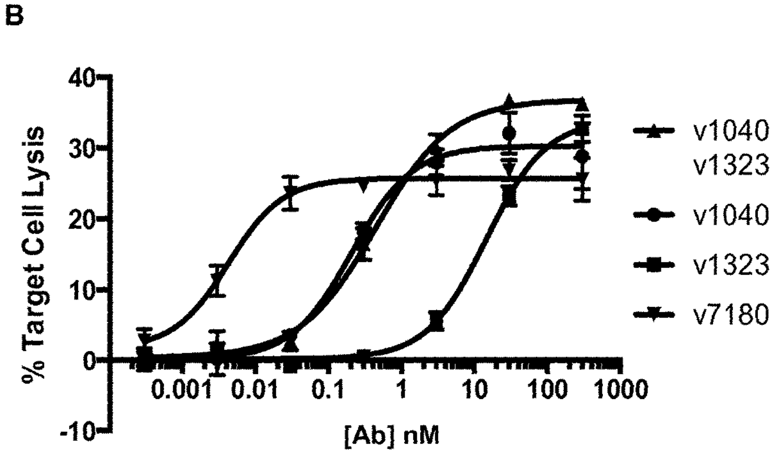
FIG. 15

A
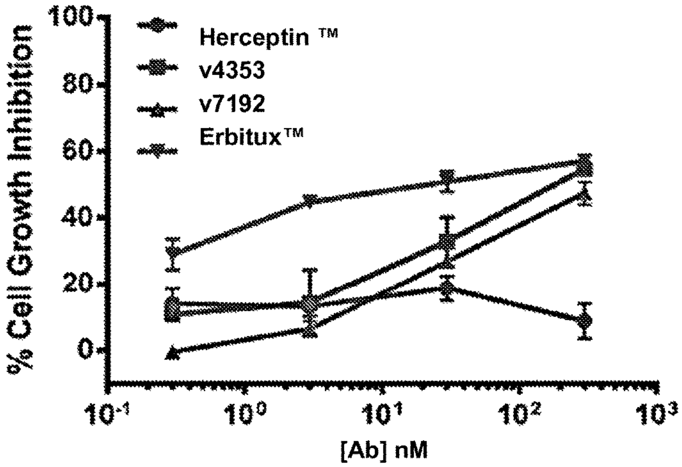
B
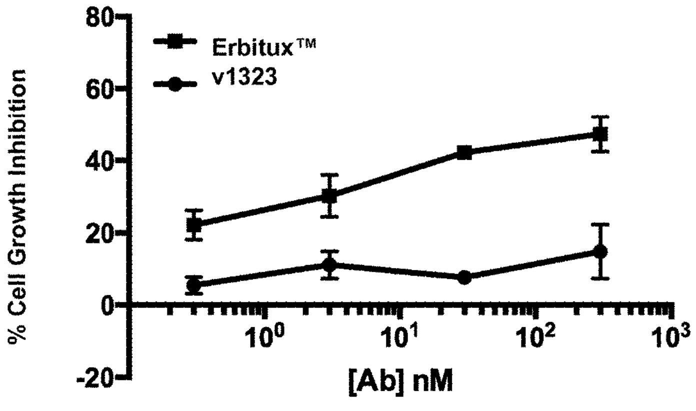
FIG. 18

MONOVALENT ANTIGEN BINDING CONSTRUCTS TARGETING EGFR AND/OR HER2 AND USES THEREOF

CROSS REFERENCE TO RELATED APPLICATIONS

This application is a 371 national phase entry of PCT/US2014/065546, filed on Nov. 13, 2014, which claims the benefit of U.S. Provisional Application No. 61/903,825, filed Nov. 13, 2013, which is hereby incorporated in its entirety by reference.

SEQUENCE LISTING

The instant application contains a Sequence Listing which has been submitted via EFS-Web and is hereby incorporated by reference in its entirety. Said ASCII copy, created on Nov. 19, 2014, is named 27951PCT_sequencelisting.txt, and is 71,182 bytes in size.

BACKGROUND

Human epidermal growth factor receptor (also known as HER-1 or Erb-B1) is a 170 kDa transmembrane receptor encoded by the c-erbB protooncogene, and exhibits intrinsic tyrosine kinase activity (Modjtahedi et al., Br. J. Cancer 73:228-235 (1996); Herbst and Shin, Cancer 94:1593-1611 (2002)). SwissProt database entry P00533 provides the sequence of EGFR. There are also isoforms and variants of EGFR (e.g., alternative RNA transcripts, truncated versions, polymorphisms, etc.) including but not limited to those identified by Swissprot database entry numbers P00533-1, P00533-2, P00533-3, and P00533-4. EGFR is known to bind ligands including epidermal growth factor (EGF), transforming growth factor-alpha (TGF-alpha), amphiregulin, heparin-binding EGF (hb-EGF), betacellulin, and epiregulin (Herbst and Shin, Cancer 94:1593-1611 (2002); Mendelsohn and Baselga, Oncogene 19:6550-6565 (2000)). EGFR regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay et al., Ann. Oncology 14:1346-1363 (2003); Tsao and Herbst, Signal 4:4-9 (2003); Herbst and Shin, Cancer 94:1593-1611 (2002); Modjtahedi et al., Br. J. Cancer 73:228-235 (1996)).

Overexpression of EGFR has been reported in numerous human malignant conditions, including cancers of the bladder, brain, head and neck, pancreas, lung, breast, ovary, colon, prostate, and kidney. (Atalay et al., Ann. Oncology 14:1346-1363 (2003); Herbst and Shin, Cancer 94:1593-1611 (2002) Modjtahedi et al., Br. J. Cancer 73:228-235 (1996)). In many of these conditions, the overexpression of EGFR correlates or is associated with poor prognosis of the patients. (Herbst and Shin, Cancer 94:1593-1611 (2002) Modjtahedi et al., Br. J. Cancer 73:228-235 (1996)). EGFR is also expressed in the cells of normal tissues, particularly the epithelial tissues of the skin, liver, and gastrointestinal tract, although at generally lower levels than in malignant cells (Herbst and Shin, Cancer 94:1593-1611 (2002)).

Various strategies to target EGFR and block EGFR signaling pathways have been reported. Small-molecule tyrosine kinase inhibitors like gefitinib, erlotinib, and CI-1033 block autophosphorylation of EGFR in the intracellular tyrosine kinase region, thereby inhibiting downstream signaling events (Tsao and Herbst, Signal 4: 4-9 (2003)). Monoclonal antibodies, on the other hand, target the extracellular portion of EGFR, which results in blocking ligand binding and thereby inhibits downstream events such as cell proliferation (Tsao and Herbst, Signal 4: 4-9 (2003)).

Chimeric antibodies comprising portions of antibodies from two or more different species (e.g., mouse and human) have been developed as an alternative to "conjugated" antibodies. For example, U.S. Pat. No. 5,891,996 (Mateo de Acosta del Rio et al.) discusses a mouse/human chimeric antibody, R3, directed against EGFR, and U.S. Pat. No. 5,558,864 discusses generation of chimeric and humanized forms of the murine anti-EGFR MAb 425. Also, Erbitux™ is a chimeric mouse/human anti-EGFR monoclonal antibody (based on mouse M225 monoclonal antibody, which resulted in HAMA responses in human clinical trials) that has been reported to demonstrate antitumor efficacy in various human xenograft models. (Herbst and Shin, Cancer 94:1593-1611 (2002)). The efficacy of Erbitux™ has been attributed to several mechanisms, including inhibition of cell events regulated by EGFR signaling pathways, and possibly by increased antibody-dependent cellular toxicity (ADCC) activity (Herbst and Shin, Cancer 94:1593-1611 (2002)). Erbitux™ was also used in clinical trials, including in combination with radiotherapy and chemotherapy (Herbst and Shin, Cancer 94:1593-1611 (2002)). Abgenix, Inc. (Fremont, Calif.) has developed ABX-EGF for cancer therapy. ABX-EGF is a fully human anti-EGFR monoclonal antibody. (Yang et al., Crit. Rev. Oncol./Hematol. 38: 17-23 (2001)). U.S. Pat. No. 8,097,436 provides further examples of EGFR targeting antibodies.

Therapy with anti-EGFR monoclonal antibodies and other EGFR inhibitors is known to be associated with a high prevalence of skin toxicity, which is thought to occur due to the expression of EGFR on normal tissues of the epidermis, sebaceous glands and hair follicular epithelium. The most often reported side-effect is a papulo-pustular rash primarily in the seborrheic areas seen in up to 90% of patients, 30% of which are severe enough to require medical intervention. In some cases, the dermatological side effects are severe enough that therapy with anti-EGFR monoclonals is suspended, continued at reduced dosage or discontinued. (Boone et al., Oncology 72:152-159 (2007)).

This application is also related to co-owned patent applications PCT/CA2011/001238, filed Nov. 4, 2011, PCT/CA2012/050780, filed Nov. 2, 2012, PCT/CA2013/00471, filed May 10, 2013, and PCT/CA2013/050358, filed May 8, 2013, the entire disclosure of each is hereby incorporated by reference in its entirety for all purposes.

SUMMARY

Provided herein is a method of treating a subject having an epidermal growth factor receptor (EGFR)-expressing tumor, comprising: contacting the tumor with an effective amount of an isolated monovalent EGFR-binding construct comprising at least one antigen-binding polypeptide comprising a heavy chain variable domain coupled, with or without a linker, to a heterodimeric Fc, wherein the antigen-binding polypeptide binds or specifically binds to EGFR, and wherein the construct binds to EGFR with a greater $B_{max}$ as compared to the corresponding isolated monospecific bivalent antigen-binding construct that binds or specifically binds EGFR.

In some aspects, the Fc is a heterodimeric human IgG1 Fc having the mutations T350V_L351Y_F405A_Y407V in Chain A, according to EU numbering, and the mutations T350V_T366L_K392L_T394W in Chain B, according to EU numbering, wherein the antigen-binding polypeptide binds to an epitope located in the extracellular domain of EGFR, wherein the subject experiences less skin toxicity from the treatment compared to a subject treated with the isolated corresponding monospecific bivalent antigen-binding construct that binds or specifically binds EGFR, and wherein the tumor expresses a first level of cell surface EGFR that is equal to or less than a second level of cell surface EGFR of one or more than one of the following cell lines: A431, A549, BT474, CACO2, HCT116, JIMT1, MDA-MB-231, SKOV3, MCF7, or SKBR3.

In some aspects, the isolated monovalent EGFR-binding construct is OA-CTX (v4353) or OA-EG2 (v1323).

In some aspects, the Fc is a heterodimeric IgG1 Fc, the Fc comprising at least two CH3 sequences, wherein the Fc is coupled, with or without a linker, to the antigen-binding polypeptide. In some aspects, the Fc is a human heterodimeric IgG1 Fc having the mutations T350V_L351Y_F405A_Y407V in Chain A, according to EU numbering, and the mutations T350V_T366L_K392L_T394W in Chain B, according to EU numbering. In some aspects, the isolated monovalent EGFR-binding construct comprises a CDR1, CDR2, and/or CDR3, and wherein the CDR1, CDR2, and/or CDR3 is the corresponding sequence shown in Table B. In some aspects, the isolated monovalent EGFR-binding construct binds to an epitope located in the extracellular domain of EGFR. In some aspects, the construct is a construct described herein, e.g., an isolated monovalent EGFR-binding construct.

In some aspects, the monovalent EGFR-binding construct is afucosylated. In some aspects, the monovalent EGFR-binding construct is conjugated to a drug, optionally wherein the drug is maytansinoid or DM1. In some aspects, the time period for treatment of the subject with the isolated monovalent EGFR-binding construct with increased efficacy and reduced adverse effects is greater than the time period for treatment with the corresponding isolated monospecific bivalent antigen-binding construct that binds or specifically binds EGFR. In some aspects, the tumor is an epidermal cell-derived cancer, a lung cancer, a breast cancer, a triple negative breast cancer, a ductal breast ductal cancer, a gastric cancer, an ovarian cancer, a HER2+ cancer, glioblastoma, a cervical cancer, a renal cancer, an uterine cancer, or a colorectal cancer.

In some aspects, the isolated monovalent EGFR-binding construct blocks binding of EGF to EGFR on the tumor. In some aspects, the isolated monovalent EGFR-binding construct blocks constitutive EGFR signaling in the tumor. In some aspects, contacting the tumor with the isolated monovalent EGFR-binding construct results in ADCC. In some aspects, contacting the tumor with the isolated monovalent EGFR-binding construct results in internalization of the isolated monovalent EGFR-binding construct.

In some aspects, the tumor expresses a first level of cell surface EGFR that is equal to or less than or less than a second level of cell surface EGFR of one or more than one of the following cell lines: A431, A549, BT474, CACO2, HCT116, JIMT1, MDA-MB-231, SKOV3, MCF7, or SKBR3. In some aspects, a sample of the tumor expresses a median level of EGFR of less than or equal to 3+, less than or equal to 2+, or less than or equal to 1+, as assessed using immunohistochemistry (IHC) staining. In some aspects, the tumor expresses a median of $3.5\times10^6$ or less, $2.8\times10^6$ or less, $1.2\times10^6$ or less, $2.4\times10^5$ or less, $2.6\times10^5$ or less, or $4.2\times10^4$ or less EGFRs per cell.

In some aspects, the treatment results in shrinking the tumor, inhibiting the growth of the tumor, increasing time to progression of the tumor, prolonging disease-free survival of the subject, decreasing metastases, increasing the progression-free survival of the subject, or increasing the overall survival of a population of subjects.

In some aspects, the subject is administered a fixed dose of the construct and experiences less skin toxicity from the treatment compared to a subject treated with a fixed dose of the corresponding isolated monospecific bivalent antigen-binding construct that binds or specifically binds EGFR, and optionally wherein the fixed dose is determined on a molar basis. In some aspects, the growth of the subject's keratinocytes is reduced less following treatment with a fixed dose of the construct compared to a subject treated with a fixed dose of the corresponding isolated monospecific bivalent antigen-binding construct that binds or specifically binds EGFR, and optionally wherein the fixed dose is determined on a molar basis.

In some aspects, the tumor is resistant or refractory to trastuzumab and/or pertuzumab and/or cetuximab.

In some aspects, the subject is a human subject.

In some aspects, the method further comprises providing an additional agent. In some aspects, the additional agent binds HER2. In some aspects, the additional agent is pertuzumab or trastuzumab. In some aspects, the monovalent EGFR binding construct and the additional agent are provided simultaneously. In some aspects, the monovalent EGFR binding construct and the additional agent are provided separately. In some aspects, the additional agent is a second isolated antigen binding construct. In some aspects, the second isolated antigen binding construct binds or specifically binds to HER2 or an extracellular domain of HER2. In some aspects, the second isolated antigen binding construct binds or specifically binds to ECD2 and/or ECD4 of HER2.

In some aspects, the treatment results in shrinking the tumor, inhibiting the growth of the tumor, increasing time to progression of the tumor, prolonging disease-free survival of the subject, or increasing the survival of the subject. In some aspects, the second isolated antigen binding construct is identical to an isolated monovalent EGFR-binding construct described herein except that the antigen-bind polypeptide of the second isolated antigen binding construct binds or specifically binds HER2 or an extracellular domain of HER2.

Also described herein is an isolated monovalent antigen-binding construct comprising: at least one antigen-binding polypeptide comprising a heavy chain variable domain, wherein the antigen-binding polypeptide binds or specifically binds epidermal growth factor receptor (EGFR); and a heterodimeric Fc, the Fc comprising at least two CH3 sequences, wherein the Fc is coupled, with or without a linker, to the antigen-binding polypeptide; wherein the monovalent antigen-binding construct selectively and/or binds or specifically binds EGFR with a greater $B_{max}$ as compared to an isolated, corresponding monospecific bivalent antigen-binding construct that binds or specifically binds EGFR; and wherein the dimerized CH3 sequences have a melting temperature (Tm) of about 68° C. or higher.

In some aspects, the isolated monovalent EGFR-binding construct is OA-CTX (v4353) or OA-EG2 (v1323).

In some aspects, a construct described herein at a construct to target ratio of 1:1 the increase in $B_{max}$ relative to the monospecific bivalent antigen-binding construct is observed at a concentration greater than the observed equilibrium constant (Kd) of the constructs up to saturating concentrations.

In some aspects, the isolated monovalent antigen-binding construct has a lower affinity for EGFR relative to isolated, corresponding monospecific bivalent antigen-binding construct that binds or specifically binds EGFR.

In some aspects, the isolated monovalent antigen-binding construct binds to an epitope located in extracellular domains 1, 2, 3, or 4 of EGFR or the extracellular domain of EGFR.

In some aspects, the antigen-binding polypeptide further comprises a light chain variable domain, a light chain CL1 domain, and/or a heavy chain CH1 domain. In some aspects, the amino acid sequence of the heavy chain variable domain is at least 80, 85, 90, 91, 92, 93, 94, 95, 96, 97, 98, 99, or 100% identical to the amino acid sequence of an EGFR-specific antigen-binding polypeptide heavy chain variable domain set forth in Table B, and wherein the amino acid sequence of the light chain variable domain is at least 80, 85, 90, 91, 92, 93, 94, 95, 96, 97, 98, 99, or 100% identical to the amino acid sequence of an EGFR-specific antigen-binding polypeptide light chain variable domain set forth in Table B. In some aspects, the amino acid sequence of the light chain CL1 domain is at least 80, 85, 90, 91, 92, 93, 94, 95, 96, 97, 98, 99, or 100% identical to the amino acid sequence of an EGFR-specific antigen-binding polypeptide light chain CL1 domain set forth in Table B, and wherein the amino acid sequence of the heavy chain CH1 domain is at least 80, 85, 90, 91, 92, 93, 94, 95, 96, 97, 98, 99, or 100% identical to the amino acid sequence of an EGFR-specific antigen-binding polypeptide heavy chain CH1 domain set forth in Table B. In some aspects, the antigen binding polypeptide is an Fab fragment, an scFv, an sdAb, an antigen binding peptide, or a protein domain capable of binding the antigen.

In some aspects, the antigen binding polypeptide comprises a heavy chain polypeptide and a light chain polypeptide. In some aspects, the heavy chain polypeptide comprises an amino acid sequence at least 80, 85, 90, 91, 92, 93, 94, 95, 96, 97, 98, 99, or 100% identical to the amino acid sequence of an EGFR-specific antigen-binding polypeptide heavy chain set forth in Table B and the light chain polypeptide comprises an amino acid sequence at least 80, 85, 90, 91, 92, 93, 94, 95, 96, 97, 98, 99, or 100% identical to the amino acid sequence of an EGFR-specific antigen-binding polypeptide light chain set forth in Table B.

In some aspects, a construct described herein has a binding affinity ($K_D$) for EGFR of less than or equal to 1.16E-8 M to 8.51E-10 M.

In some aspects, a construct described herein, when bound to EGFR, inhibits A431 cell growth relative to a control and/or increases % ADCC-mediated target cell lysis of BT-474 cells relative to a control and/or causes internalization of EGFR, and/or causes downregulation of EGFR.

In some aspects, the construct is internalized into a cell upon binding to EGFR on the cell.

In some aspects, the Fc is fused to the antigen-binding polypeptide by a linker. In some aspects, the linker is a polypeptide linker. In some aspects, the linker comprises an IgG1 hinge region.

In some aspects, EGFR is EGFR isoform A or EGFRvIII.

In some aspects, the construct is conjugated to at least one drug. In some aspects, the drug is a maytansinoid. In some aspects, the maytansinoid is DM1. In some aspects, the maytansinoid is conjugated to the construct through an SMCC linker.

In some aspects, the construct or the antigen-binding polypeptide is neutralizing. In some aspects, the construct or the antigen-binding polypeptide is non-neutralizing.

In some aspects, the Fc is a human Fc. In some aspects, the human Fc is a human IgG1 Fc.

In some aspects, the dimerized CH3 sequences have a melting temperature (Tm) of about 68, 69, 70, 71, 72, 73, 74, 75, 76, 77, 77.5, 78, 79, 80, 81, 82, 83, 84, or 85° C. or higher. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

In some aspects, the heterodimeric Fc comprises one or more modifications in at least one of the CH3 sequences. In some aspects, the heterodimeric Fc domain comprises one or more modifications in at least one of the CH3 sequences that promote the formation of a heterodimer with stability comparable to a wild-type homodimeric Fc. In some aspects, the heterodimeric Fc domain comprises a heterodimeric IgG1 Fc having the mutations T350V_L351Y_F405A_Y407V in Chain A, according to EU numbering, and the mutations T350V_T366L_K392L_T394W in Chain B, according to EU numbering.

In some aspects, the heterodimeric Fc further comprises at least one CH2 domain. In some aspects, the CH2 domain(s) of the heterodimeric Fc comprises one or more modifications.

In some aspects, the heterodimeric Fc comprises one or more modifications to promote selective binding of Fc-gamma receptors.

Also described herein is a second isolated monovalent antigen-binding construct that competes for binding to EGFR with an isolated monovalent antigen-binding construct described herein, optionally wherein, the second isolated monovalent antigen-binding construct displaces the isolated monovalent antigen-binding construct according to any preceding construct claim by greater than 50%, 60%, 70%, 80%, 90%, 95%, 99%, or 100%.

Also described herein is an isolated monovalent antigen-binding construct, wherein the construct is characterized by one or more of:

a. higher cell surface binding ($B_{MAX}$) as determined by FACS on one or more of BT474 cells, HCT116 cells, MDA-MB-234 cells, or SKOV3 cells compared to the corresponding isolated monospecific bivalent antigen-binding construct that binds or specifically binds EGFR,
b. mediation of increased antibody dependent cellular cytotoxicity (ADCC) of BT-474 cells compared to that mediated by the corresponding isolated monospecific bivalent antigen-binding construct that binds or specifically binds EGFR, or
c. internalization by JIMT1 cells;

when the cells are contacted by the construct.

Also described herein is an isolated monovalent antigen-binding construct, wherein the construct is afucosylated, and wherein the construct mediates a 1.9 fold increase in ADCC of A549 cells and/or a 1.4-fold increase in ADCC of HCT116 cells over that mediated by the corresponding isolated monospecific bivalent antigen-binding construct that binds or specifically binds EGFR.

In some aspects, an antigen binding construct comprises at least one modification, and wherein the modification is afucosylation.

Also described herein is an isolated polynucleotide or set of isolated polynucleotides comprising at least one sequence that encodes an isolated monovalent antigen-binding construct described herein. In some aspects, the polynucleotide or set of polynucleotides is cDNA.

Also described herein is a vector or set of vectors comprising one or more of the polynucleotides or sets of polynucleotides described herein. In some aspects, the vector is selected from the group consisting of a plasmid, a viral vector, a non-episomal mammalian vector, an expression vector, and a recombinant expression vector.

Also described herein is an isolated cell comprising a polynucleotide or set of polynucleotides described herein or a vector described herein. In some aspects, the cell is a hybridoma, a Chinese Hamster Ovary (CHO) cell, or a HEK293 cell.

Also described herein is a pharmaceutical composition comprising an isolated monovalent antigen-binding construct described herein and a pharmaceutically acceptable carrier. In some aspects, the composition further includes one or more substances selected from the group consisting of a buffer, an antioxidant, a low molecular weight molecule, a drug, a protein, an amino acid, a carbohydrate, a lipid, a chelating agent, a stabilizer, and an excipient.

In some aspects, the composition further includes a second isolated antigen binding construct. In some aspects, the second construct specifically binds to HER2 or an extracellular domain of HER2. In some aspects, the second construct specifically binds to extracellular domain (ECD)2 and/or ECD4 of HER2. In some aspects, the second construct is identical to the isolated monovalent EGFR-binding construct described herein except that the antigen-bind polypeptide specifically binds HER2 or an extracellular domain of HER2.

Also described herein is a pharmaceutical composition comprising a construct described herein for use in a medicine. In some aspects, the composition is for use in treating a cancerous condition. In some aspects, the cancerous condition is an EGFR-expressing cancer, an epithelial cell-derived cancer, breast cancer, a HER2-expressing cancer, a lung cancer, a triple negative breast cancer, a ductal breast ductal cancer, a gastric cancer, an ovarian cancer, a head and neck cancer, glioblastoma, a cervical cancer, a renal cancer, an uterine cancer, a pancreatic cancer, or a colorectal cancer.

Also described herein is a method of obtaining an isolated monovalent antigen-binding construct described herein, the method comprising the steps of: (a) obtaining a host cell culture, wherein the host cell comprises one or more nucleic acid sequences encoding the antigen-binding construct; (b) culturing the host cell culture under conditions sufficient to express the isolated monovalent antigen-binding construct; and (c) recovering the antigen-binding construct from the host cell culture.

Also described herein is a method of treating cancer or a disorder related to EGFR and/or HER signaling in a subject comprising providing to a subject in need thereof an effective amount of a pharmaceutical composition or a construct described herein.

In some aspects, the cancer is an EGFR-expressing cancer, an epithelial cell-derived cancer, breast cancer, a HER2-expressing cancer, a lung cancer, a triple negative breast cancer, a ductal breast ductal cancer, a gastric cancer, an ovarian cancer, glioblastoma, a cervical cancer, a renal cancer, an uterine cancer, or a colorectal cancer.

In some aspects, the method comprises providing the isolated monovalent construct in addition to an additional agent. In some aspects, the isolated monovalent construct is provided simultaneously with the additional agent. In some aspects, the isolated monovalent construct is provided separately from the additional agent. In some aspects, the additional agent is a second, distinct isolated antigen binding construct. In some aspects, the second construct specifically binds to HER2 or an extracellular domain of HER2. In some aspects, the second construct specifically binds to ECD2 and/or ECD4 of HER2. In some aspects, the second construct is identical to the isolated monovalent antigen-binding construct of claim 1 except that the antigen-bind polypeptide specifically binds HER2 or an extracellular domain of HER2.

In some aspects, the isolated monovalent EGFR-binding construct blocks binding of EGF to EGFR on the tumor. In some aspects, the isolated monovalent EGFR-binding construct blocks constitutive EGFR signaling in the tumor. In some aspects, contacting the tumor with the isolated monovalent EGFR-binding construct results in ADCC. In some aspects, contacting the tumor with the isolated monovalent EGFR-binding construct results in internalization of the isolated monovalent EGFR-binding construct.

Also described herein is a method of inhibiting growth of a tumor, shrinking a tumor, or increasing the survival of a subject having a tumor, comprising contacting the tumor with an effective amount of a composition or construct described herein.

In some aspects, the tumor is an epithelial cell-derived tumor or a HER2+ tumor. In some aspects, the isolated monovalent EGFR-binding construct blocks binding of EGF to EGFR on the tumor. In some aspects, the isolated monovalent EGFR-binding construct blocks constitutive EGFR signaling in the tumor. In some aspects, contacting the tumor with the isolated monovalent EGFR-binding construct results in ADCC. In some aspects, contacting the tumor with the isolated monovalent EGFR-binding construct results in internalization of the isolated monovalent EGFR-binding construct.

Also described herein is a method of inhibiting, reducing or blocking the EGFR and/or HER signaling in a cell, comprising contacting the cell with an effective amount of a construct or composition described herein.

In some aspects, the cell is an EGFR-expressing cancer cell, a breast cancer cell, an epithelial cell-derived tumor cell, a HER2+ tumor cell, a lung cancer cell, a triple negative breast cancer cell, a ductal breast cancer cell, a gastric cancer cell, and head and neck cancer cell, a pancreatic cancer cell, an ovarian cancer cell, a glioblastoma cell, a cervical cancer cell, a renal cancer cell, an uterine cancer cell, or a colorectal cancer cell.

Also described herein is a kit comprising an isolated antigen binding construct described herein and instructions for use, and optionally, further comprising a second isolated antigen binding construct.

Also described herein is an isolated antigen binding construct as described herein for use in the manufacture of a medicament for treating a disease, optionally wherein the disease is cancer, e.g., an EGFR-expressing cancer, an epithelial cell-derived cancer, breast cancer, a HER2-expressing cancer, a lung cancer, a triple negative breast cancer, a ductal breast ductal cancer, a gastric cancer, an ovarian cancer, glioblastoma, a cervical cancer, a renal cancer, an uterine cancer, or a colorectal cancer.

BRIEF DESCRIPTION OF THE DRAWINGS

These and other features, aspects, and advantages of the present invention will become better understood with regard to the following description, and accompanying drawings, where:

FIG. 1A shows the SEC profile of v4353 with the main peak at retention volume of 79.95 ml. FIG. 1B shows the SEC profile of v1323 with main peak at retention volume of 84.74 ml. FIG. 1C shows the SDS-PAGE analysis of both v4353 and v1323 with species at approximately 110 kDa and 66 kDa, respectively. FIG. 1D is a schematic drawing of an exemplary one armed anti-EGFR antibody in the format of v4353. FIG. 1E is a schematic drawing of an exemplary one armed anti-EGFR antibody in the format of v1323. FIG. 1F is a schematic drawing of a bivalent (full size) anti-EGFR antibody in the format of v7180.

FIGS. 2A and 2B depict the sensorgrams for v4353 (neutralizing antibody) and its ability to bind to EGFR and lack of binding to HER2, respectively. FIGS. 2C and 2D depict the sensorgrams for v1323 (non-neutralizing) and its ability to bind to EGFR and lack of binding to HER2, respectively.

FIG. 6 depicts measurement of the ability of an exemplary OA-EGFR antibody to be internalized and to downregulate EGFR expression. FIG. 6A shows the effect of 20 nM of v4353 to internalize and downregulate EGFR expression in JIMT-1 cells. FIG. 6B shows the effect of 100 nM and 200 nM of v4353 to internalize and downregulate EGFR expression in JIMT-1 cells, either alone, or in combination with other antibodies. For each experimental group in 6A and 6B, the left bar is surface at 4 C degrees; the middle bar is surface at 37 C degrees; and the right bar is internal at 37 C degrees.

FIG. 11 shows the glycan analysis of the tryptic digest of the exemplary afucosylated antibody v7192 by LC-MS. "TKPREEQYNSTYR" disclosed as SEQ ID NO: 69 and "EEQYNSTYR" disclosed as SEQ ID NO: 70.

FIGS. 15A and 15B show the concentration dependent ADCC dose response curves of the exemplary OAAs on the Caco2 cell line assessed at a PBMC effector to target Caco2 E:T ratio of 50:1.

FIG. 18A shows the growth inhibition dose response curves of exemplary OA-EGFR antibodies v4353 and v7192 compared to Erbitux™ and Herceptin™ on an immortalized HACAT keratinocyte cell line in the presence of serum. FIG. 18B shows the growth inhibition dose response curves of OA-EGFR antibody v1323 compared to that of Erbitux™ in the absence of serum.

DETAILED DESCRIPTION

Figure 1:
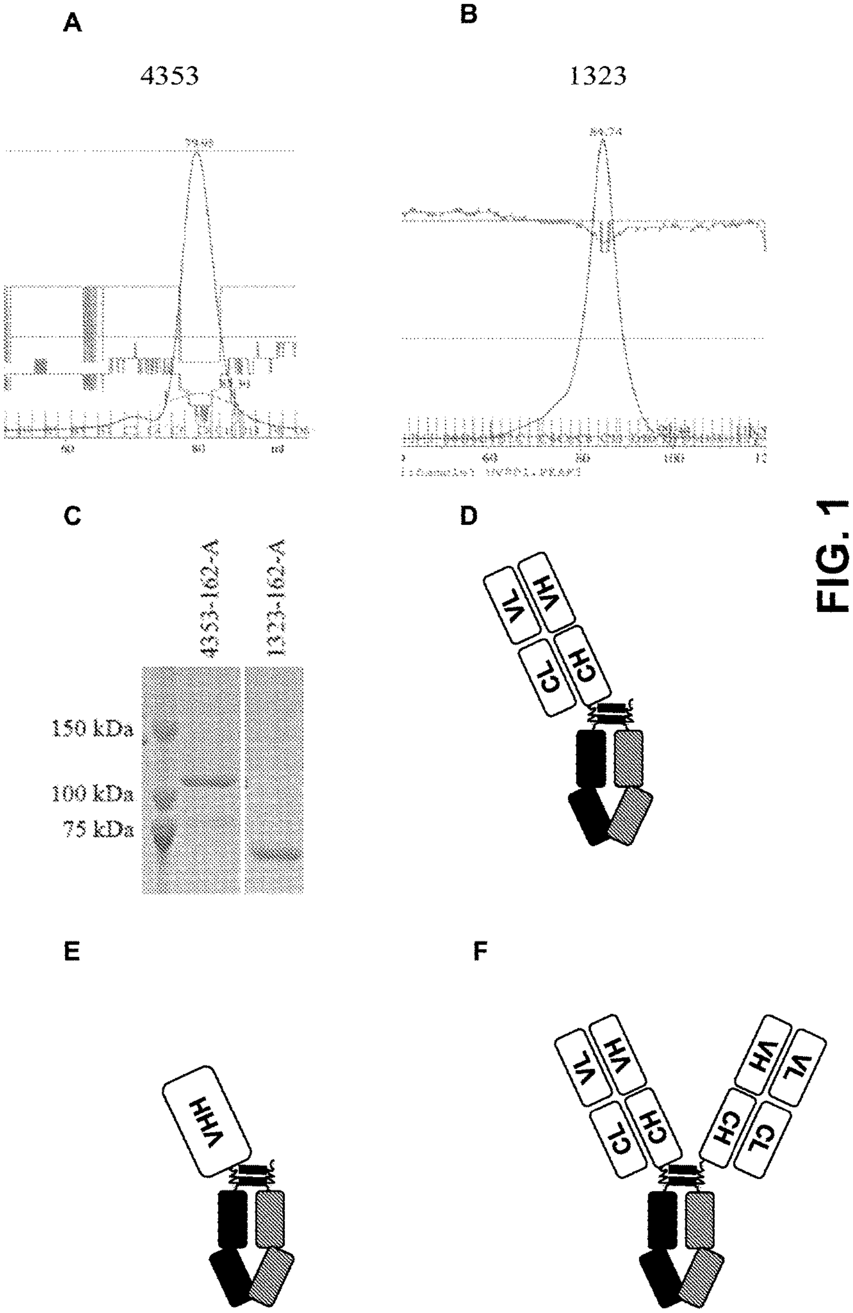
FIG. 1 depicts the assessment of purity of exemplary one armed anti-EGFR antibodies (OA-EGFR), v4353 and 1323.

Provided herein are monovalent antigen-binding constructs comprising an antigen-binding polypeptide construct which monovalently binds an antigen. In some aspects, the construct includes a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said monovalent antigen-binding construct displays an increase in binding density and $B_{max}$ to a target cell displaying said antigen as compared to a corresponding monospecific bivalent antigen-binding construct with two antigen binding regions, and wherein said monovalent antigen-binding construct shows superior efficacy and/or bioactivity as compared to the corresponding bivalent antigen-binding construct, and wherein said superior efficacy and/or bioactivity is the result of the increase in binding density and resulting increase in decoration of a target cell. The increase in $B_{max}$ or binding density and resultant increase in target decoration by the monovalent antigen-binding construct provided here is the effect of specific target binding and not due to nonspecific binding. In certain embodiments the maximum binding occurs at a target to antibody ratio of 1:1.

In certain embodiments, the monovalent antigen-binding constructs provided herein possess at least one or more of the following attributes: increased $B_{max}$ compared to corresponding monospecific bivalent antigen-binding constructs (FSA); $K_d$ comparable to corresponding FSA; same or slower off-rate compared to corresponding FSA; decreased or partial agonism; no cross-linking and dimerization of targets; specificity and/or selectivity for target cell of interest; full or partial or no inhibition of target cell growth; complete Fc capable of inducing effector activity; and ability to be internalized by target cell.

In certain embodiments, the monovalent antigen-binding constructs provided herein possess the following minimal attributes: increased $B_{max}$ compared to corresponding FSA; $K_d$ comparable to corresponding FSA; same or slower off-rate compared to corresponding FSA; decreased or partial agonism; no cross-linking and dimerization of targets; specificity and/or selectivity for target cell of interest; full or partial or no inhibition of target cell growth; complete Fc capable of inducing effector activity; and optionally ability to be internalized by target cell.

Provided herein is a monovalent antigen-binding construct wherein said construct is at least one of: a monovalent lytic antibody, a monovalent internalizing antibody and combinations thereof. In some embodiments, the antigen-binding construct is a monovalent lytic antibody and/or a monovalent internalizing antibody depending on the balance these antibodies display between the following efficacy factors: a) the ability of the monovalent antigen-binding construct to be internalized, b) the increased $B_{max}$ and Kd/on-off rate of the monovalent antigen-binding construct, and c) the degree of agonism/partial agonism of the monovalent antigen-binding construct Provided herein is a method of increasing antibody concentration in at least one target cell comprising providing to the target cell a monovalent antigen-binding construct comprising: an antigen-binding polypeptide construct which monovalently binds an antigen; a dimeric Fc domain; wherein said monovalent antigen-binding construct displays an increase in binding density and Bmax (maximum binding) to a target cell displaying said antigen as compared to a corresponding bivalent antigen-binding construct with two antigen binding regions, and wherein said monovalent antigen-binding construct shows better therapeutic efficacy compared to a corresponding bivalent antigen-binding construct, and wherein said efficacy is not caused by crosslinking of the antigen, antigen dimerization, prevention of antigen modulation, or prevention of antigen activation. Conversely, the other is true that efficacy can be caused by antigen modulation or antigen activation so long as these do not overcome the net killing effect.

In some embodiments is an isolated monovalent antigen-binding construct described herein, wherein said antigen-binding construct exhibits no avidity.

Provided herein is an isolated monovalent antigen-binding construct comprising an antigen-binding polypeptide construct which monovalently binds an antigen; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said monovalent antigen-binding construct displays an increase in binding density and Bmax (maximum binding) to a target cell displaying said antigen as compared to a corresponding FSA construct with two antigen binding regions, wherein said monovalent antigen-binding construct shows superior efficacy and/or bioactivity as compared to the corresponding bivalent antigen-binding construct, and wherein said superior efficacy and/or bioactivity is the result of the increase in binding density.

Provided in certain embodiments is an isolated monovalent antigen-binding construct described herein, wherein the increase in binding density and Bmax relative to a monospecific bivalent antibody is observed at a concentration greater than the observed equilibrium constant (Kd) and at saturating concentrations of the antibodies. In some embodiments the superior efficacy and/or bioactivity is the result of increased FcγR or complement (C1q) binding and at least one of higher ADCC, higher ADCP and higher CDC as compared to said corresponding bivalent antigen-binding construct. In specific embodiments, the isolated monovalent antigen-binding construct is anti-proliferative and is internalized. In certain embodiments is an isolated monovalent antigen-binding construct described herein wherein said increase in binding density and Bmax relative to the FSA is independent of the density of the antigen on the target cell. In some embodiments is provided an isolated monovalent antigen-binding construct described herein, wherein the target cell is a cancer cell, or an EGFR and/or HER2 expressing diseased cell. In an embodiment, the isolated monovalent antigen-binding construct described herein exhibits no avidity.

Definitions

It is to be understood that this invention is not limited to the particular protocols; cell lines, constructs, and reagents described herein and as such may vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

A "dimer" or "heterodimer" is a molecule comprising at least a first monomer polypeptide and a second monomer polypeptide. In the case of a heterodimer, one of said monomers differs from the other monomer by at least one amino acid residue. In certain embodiments, the assembly of the dimer is driven by surface area burial. In some embodiments, the monomeric polypeptides interact with each other by means of electrostatic interactions and/or salt-bridge interactions that drive dimer formation by favoring the desired dimer formation and/or disfavoring formation of other non-desired specimen. In some embodiments, the monomer polypeptides interact with each other by means of hydrophobic interactions that drive desired dimer formation by favoring desired dimer formation and/or disfavoring formation of other assembly types. In certain embodiments, the monomer polypeptides interact with each other by means of covalent bond formation. In certain embodiments, the covalent bonds are formed between naturally present or introduced cysteines that drive desired dimer formation. In certain embodiments described herein, no covalent bonds are formed between the monomers. In some embodiments, the polypeptides interact with each other by means of packing/size-complementarity/knobs-into-holes/protruberance-cavity type interactions that drive dimer formation by favoring desired dimer formation and/or disfavoring formation of other non-desired embodiments. In some embodiments, the polypeptides interact with each other by means of cation-pi interactions that drive dimer formation. In certain embodiments the individual monomer polypeptides cannot exist as isolated monomers in solution.

The term "Fc domain" or "Fc", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc domain may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc domain. An Fc polypeptide may be obtained from any suitable immunoglobulin, such as IgG1, IgG2, IgG3, or IgG4 subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

Antibody "effector functions" refer to those biological activities attributable to the Fc domain (a native sequence Fc domain or amino acid sequence variant Fc domain) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell.

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen.

"Antibody-dependent cellular phagocytosis and "ADCP" refer to the destruction of target cells via monocyte or macrophage-mediated phagocytosis.

The terms "Fc receptor" and "FcR" are used to describe a receptor that binds to the Fc domain of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

A "disorder" is any condition that would benefit from treatment with an antibody or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, myeloma (e.g., multiple myeloma), hepatocellular cancer, gastrointestinal cancer, pancreatic cancer, glioblastoma/glioma (e.g., anaplastic astrocytoma, glioblastoma multiforme, anaplastic oligodendroglioma, anaplastic oligodendroastrocytoma), cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishing of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder. In one embodiment, antibodies and methods of the invention effect tumor regression. In one embodiment, antibodies and methods of the invention effect inhibition of tumor/cancer growth.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the protein has been secreted, including medium either before or after a proliferation step. The term also may encompass buffers or reagents that contain host cell lysates, such as in the case where an antigen binding construct described herein is produced intracellularly and the host cells are lysed or disrupted to release the heteromultimer.

As used herein, the term "modulated serum half-life" means the positive or negative change in circulating half-life of an antigen binding polypeptide that is comprised by an antigen-binding construct described herein relative to its native form. Serum half-life is measured by taking blood samples at various time points after administration of the construct, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of an antigen binding polypeptide comprised by a monovalent antigen-binding construct described herein, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitutions providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139]8) Cysteine (C), Methionine (M) (see, e.g., Creighton, Proteins: Structures and Molecular Properties (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of monovalent antigen-binding construct being administered, which will relieve to some extent one or more of the symptoms of the disease, condition or disorder being treated. Compositions containing the construct described herein can be administered for prophylactic, enhancing, and/or therapeutic treatments.

The terms "enhance" or "enhancing" means to increase or prolong either in potency or duration a desired effect. Thus, in regard to enhancing the effect of drug molecule or therapeutic agents, the term "enhancing" refers to the ability to increase or prolong, either in potency or duration, the effect of therapeutic agents on a system. An "enhancing-effective amount," as used herein, refers to an amount adequate to enhance the effect of another therapeutic agent or drug in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

The term "monospecific bivalent antigen-binding construct" as used herein refers to an antigen-binding construct which has two antigen binding domains (bivalent), both of which bind to the same epitope/antigen (monospecific). The antigen binding domains could be, but are not limited to, protein constructs such as Fab (fragment antigen binding), scFv (single chain Fv) and sdab (single domain antibody). The monospecific bivalent antigen-binding construct is also referred to herein as a "full-size antibody" or "FSA." In some embodiments, a monospecific bivalent antigen-binding construct is a reference against which the properties of the monovalent antigen-binding constructs are measured. In other embodiments, a combination of two monospecific bivalent antigen-binding constructs is a reference against which the properties of a combination of two monovalent antigen-binding constructs are measured. In cases where a combination of two monospecific bivalent antigen-binding constructs is used, the monospecific bivalent antigen-binding constructs bind to non-overlapping epitopes on EGFR. In some embodiments, where a combination of two monospecific bivalent antigen-binding constructs is used, a single monospecific bivalent antigen-binding construct is used as a reference, where the single monospecific bivalent antigen-binding construct represents a standard of care (SOC) therapy, e.g., Erbitux.

The phrase that a construct "specifically binds" to a target refers to a binding reaction which is determinative of the presence of the target in the presence of a heterogeneous population of other biologics. Thus, under designated immunoassay conditions, a specified construct specifically binds to a particular target and does not bind in a significant amount to other biologics present in the sample. Specific binding of an antigen binding construct to a target under such conditions requires the antigen binding construct to be specific to the target. A variety of immunoassay formats can be used to select antigen binding constructs specifically immunoreactive with a particular protein. For example, solid-phase ELISA immunoassays are routinely used to select antigen binding constructs (e.g., monoclonal antibodies) specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The term "avidity" is used here to refer to the combined synergistic strength of binding affinities and a key structure and biological attribute of therapeutic monospecific bivalent antibodies. Lack of avidity and loss of synergistic strength of binding can result in reduced apparent target binding affinity. On the other hand, on a target cell with fixed number of antigens, avidity resulting from the multivalent (or bivalent) binding causes increased occupancy of the target antigen at a lower number of antibody molecules relative to antibody which displays monovalent binding. With a lower number of antibody molecules bound to the target cell, in the application of bivalent lytic antibodies, antibody dependent cytotoxic killing mechanisms may not occur efficiently resulting in reduced efficacy. Not enough antibodies are bound to mediate ADCC, CDC, ADCP as these types of effector functions are generally considered to be Fc concentration threshold dependent. In the case of agonistic antibodies, reduced avidity reduces their efficiency to crosslink and dimerize antigens and activate the pathway.

"Single domain antibodies" or "Sdab"—Single domain antibodies such as the Camelid VhH domain are individual immunoglobulin domains. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

As used herein, the term "EGFR" refers to epidermal growth factor receptor (also known as HER-1 or Erb-B1), including the human form(s) (Ulrich, A. et al., Nature 309:418-425 (1984); SwissProt Accession #P00533; secondary accession numbers: O00688, O00732, P06268, Q14225, Q92795, Q9BZS2, Q9GZX1, Q9H2C9, Q9H3C9, Q9UMD7, Q9UMD8, Q9UMG5), as well as naturally-occurring isoforms and variants thereof. Such isoforms and variants include but are not limited to the EGFRvIII variant, alternative splicing products (e.g., as identified by SwissProt Accession numbers P00533-1, P00533-2, P00533-3, P00533-4), variants GLN-98, ARG-266, Lys-521, ILE-674, GLY-962, and PRO-988 (Livingston, R. J. et al., NIEHS-SNPs, environmental genome project, NIEHS ES15478, Department of Genome Sciences, Seattle, Wash. (2004)), and others identified by the following accession numbers: NM005228.3, NM201282.1, NM201283.1, NM201284.1 (REFSEQ mRNAs); AF125253.1, AF277897.1, AF288738.1, AI217671.1, AK127817.1, AL598260.1, AU137334.1, AW163038.1, AW295229.1, BC057802.1, CB160831.1, K03193.1, U48722.1, U95089.1, X00588.1, X00663.1; H5448451, H5448453, H5448452 (MIPS assembly); DT.453606, DT.86855651, DT.95165593, DT.97822681, DT.95165600, DT.100752430, DT.91654361, DT.92034460, DT.92446349, DT.97784849, DT.101978019, DT.418647, DT.86842167, DT.91803457, DT.92446350, DT.95153003, DT.95254161, DT.97816654, DT.87014330, DT.87079224 (DOTS Assembly). All accession numbers referenced herein are taken from the NCBI database (or other relevant, referenced database) as of Nov. 8, 2013.

A "HER receptor" is a receptor protein tyrosine kinase which belongs to the human epidermal growth factor receptor (HER) family and includes EGFR, HER2, HER3 and HER4 receptors. The HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated.

The extracellular (ecto) domain of HER2 comprises four domains, Domain I (ECD1, amino acid residues from about 1-195), Domain II (ECD2, amino acid residues from about 196-319), Domain III (ECD3, amino acid residues from about 320-488), and Domain IV (ECD4, amino acid residues from about 489-630) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), Tse et al. *Cancer Treat Rev.* 2012 April; 38(2):133-42 (2012), or Plowman et al. *Proc. Natl. Acad. Sci.* 90:1746-1750 (1993).

The expressions "ErbB2" and "HER2" are used interchangeably herein and refer to human HER2 protein described, for example, in Semba et al., *PNAS* (*USA*) 82:6497-6501 (1985) and Yamamoto et al. *Nature* 319:230-234 (1986) (Genebank accession number X03363). The term "erbB2" and "neu" refers to the gene encoding human ErbB2 protein. p185 or p185neu refers to the protein product of the neu gene. Preferred HER2 is native sequence human HER2.

By "HER ligand" is meant a polypeptide which binds to and/or activates an HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)) or cripto (CR-1) (Kannan et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4 and heregulins.

"Heregulin" (HRG) when used herein refers to a polypeptide encoded by the heregulin gene product as disclosed in U.S. Pat. No. 5,641,869 or Marchionni et al., *Nature,* 362:312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641,869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)). The term includes biologically active fragments and/or amino acid sequence variants of a native sequence HRG polypeptide, such as an EGF-like domain fragment thereof (e.g. HRGβ1177-244).

"HER activation" or "HER2 activation" refers to activation, or phosphorylation, of any one or more HER receptors, or HER2 receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

The "Fab fragment" of an antibody (also referred to as fragment antigen binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen binding. Fab' fragments differ from Fab fragments by the addition of a few residues at the carboxy terminus of the heavy chain CH1 domain including one or more cysteines from the antibody hinge region.

"Single-chain Fv" or "scFv" antibody fragments comprise the VH and VL domains of an antibody, wherein these domains are present in a single polypeptide chain. In one embodiment, the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or Trastuzumab (HERCEPTIN®) as described in Table 3 of U.S. Pat. No. 5,821,337 expressly incorporated herein by reference; humanized 520C9 (WO93/21319) and 20' humanized 2C4 antibodies as described in US Patent Publication No. 2006/0018899.

The "epitope 2C4" is the region in the extracellular domain of HER2 to which the antibody 2C4 binds. In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 2C4 epitope of HER2 using methods known in the art and/or one can study the antibody-HER2 structure (Franklin et al. *Cancer Cell* 5:317-328 (2004)) to see what domain(s) of HER2 is/are bound by the antibody. Epitope 2C4 comprises residues from domain II in the extracellular domain of HER2. 2C4 and Pertuzumab bind to the extracellular domain of HER2 at the junction of domains I, II and III. Franklin et al. *Cancer Cell* 5:317-328 (2004).

The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, see FIG. 1 of US Patent Publication No. 2006/0018899).

The "epitope 7C2/F3" is the region at the N terminus, within Domain I, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of HER2, see FIG. 1 of US Patent Publication No. 2006/0018899).

The term "antigen modulation" as used herein refers to a change or loss of surface receptor density via internalization or down regulation) such as in the ADC.

Antigen-Binding Constructs

Provided in certain embodiments is an isolated monovalent antigen-binding construct that binds EGFR and/or HER2 on a target cell with low EGFR and/or HER2 expression, comprising: an antigen binding polypeptide construct which monovalently binds EGFR and/or HER2; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said antigen-binding construct is anti-proliferative and is internalized by a target cell, wherein said construct displays an increase in binding density and Bmax (maximum binding) to EGFR and/or HER2 displayed on the target cell as compared to a corresponding bivalent antigen-binding construct which binds EGFR and/or HER2, and wherein said construct displays at least one of higher ADCC, higher ADCP and higher CDC as compared to said corresponding bivalent EGFR and/or HER2 binding antigen-binding constructs. In certain embodiments, the target cell with low EGFR and/or HER2 expression is a cancer cell. In some embodiments the target cell with low EGFR and/or HER2 expression is an epithelial cell-derived cancer cell, a breast cancer cell, a lung cancer cell, a triple negative breast cancer cell, a ductal breast ductal cancer cell, a gastric cancer cell, a head and neck cancer cell, a pancreatic cancer cell, an ovarian cancer cell, or a colorectal cancer cell. In some embodiments, the target cell with low EGFR and/or HER2 expression is a breast cancer cell.

In certain embodiments, antigen-binding polypeptide constructs which monovalently bind an antigen can be derived from known antibodies or antigen-binding domains, or can be derived from novel antibodies or antigen-binding domains. The identification of an antigen-binding polypeptide construct for the monovalent antigen-binding construct is based on the selection of the target cell and on the selection of an antigen expressed on the surface of the target cell. For example, once the target cell has been selected, an antigen is then selected that is a) expressed on the cell surface of the target cell, but not expressed on the surface of other cells, or b) expressed at higher levels on the cell surface of the target cell, but expressed at lower levels on the surface of other cells. This allows for selective targeting of the target cell.

EGFR Binding Constructs

In some embodiments the monovalent antigen-binding construct described herein is designed to target a cell expressing EGFR and the antigen-binding polypeptide construct binds EGFR. EGFR is proto-oncogene belonging to the human epidermal growth factor receptor (EGFR) family and is often over-expressed in a subset of cancers. In some embodiments, the antigen-binding polypeptide construct binds EGFR and the target cell is a low, medium or high EGFR expressing cell. In an embodiment, the antigen-binding polypeptide construct binds EGFR and the target cell is a low EGFR expressing cell. In another embodiment, the antigen-binding polypeptide construct binds EGFR and the target cell is a low EGFR expressing cell with decreased binding to bivalent EGFR binding antibodies. In a further embodiment, the antigen-binding polypeptide construct binds EGFR and the target cell is a low EGFR expressing cell. In an embodiment, the antigen-binding polypeptide construct binds EGFR and the target cell is a cancer cell. In a certain embodiment, the antigen-binding polypeptide construct binds EGFR and the target cell is an epithelial cell-derived cancer cell, a breast cancer cell, a lung cancer cell, a triple negative breast cancer cell, a ductal breast ductal cancer cell, a gastric cancer cell, a head and neck cancer cell, a pancreatic cancer cell, an ovarian cancer cell, or a colorectal cancer cell.

In some embodiments of the monovalent antigen-binding construct described herein, the dimeric Fc polypeptide construct is heterodimeric. In some embodiments of the monovalent antigen-binding construct described, the antigen-binding polypeptide construct binds EGFR. In some embodiments, the antigen-binding polypeptide construct binds at least one EGFR extracellular domain. In certain embodiments, the antigen-binding polypeptide construct binds EGFR expressed by a target cell which is a low, medium or high EGFR expressing cell. In certain embodiments, the EGFR expressing cell displays decreased binding to bivalent EGFR binding antibodies. In an embodiment, the antigen-binding polypeptide construct binds EGFR and the target cell is at least one of an estrogen receptor negative cell, a progesterone receptor negative cell and anti-EGFR antibody resistant tumor cell with decreased binding to bivalent EGFR binding antibodies.

In some embodiments of the monovalent antigen-binding construct described herein, the dimeric Fc polypeptide construct is heterodimeric. In certain embodiments of the monovalent antigen-binding construct described herein, the monovalent antigen binding polypeptide construct is a Fab fragment, an scFv, and sdAb, an antigen binding peptide or a protein domain capable of binding the antigen. In some embodiments is provided an isolated monovalent antigen-binding construct as described herein wherein the monovalent antigen binding polypeptide construct is a Fab fragment comprising a heavy chain polypeptide and a light chain polypeptide.

Provided herein is an isolated monovalent antigen-binding construct that binds EGFR comprising: an antigen binding polypeptide construct which monovalently binds EGFR; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said antigen-binding construct is anti-proliferative and is internalized by a target cell, wherein said construct displays an increase in binding density and Bmax (maximum binding) to EGFR displayed on the target cell as compared to a corresponding bivalent antigen-binding construct which binds EGFR, and wherein said construct displays at least one of higher ADCC, higher ADCP and higher CDC as compared to said corresponding bivalent EGFR binding antigen-binding constructs.

Provided in certain embodiments is an isolated monovalent antigen-binding construct that binds EGFR on a target cell with low EGFR expression, comprising: an antigen binding polypeptide construct which monovalently binds EGFR; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said antigen-binding construct is anti-proliferative and is internalized by a target cell, wherein said construct displays an increase in binding density and Bmax (maximum binding) to EGFR displayed on the target cell as compared to a corresponding bivalent antigen-binding construct which binds EGFR, and wherein said construct displays at least one of higher ADCC, higher ADCP and higher CDC as compared to said corresponding bivalent EGFR binding antigen-binding constructs. In certain embodiments, the target cell with low EGFR expression is a cancer cell. In some embodiments, the target cell with low EGFR expression is a epithelial cell-derived cancer cell.

In an embodiment is the isolated monovalent antigen-binding construct described herein, wherein the antigen-binding construct inhibits target cell proliferation. In some embodiments is an isolated monovalent antigen-binding construct described herein wherein said monovalent EGFR binding polypeptide construct is at least one of Fab, an scFv, an sdAb, or a polypeptide. In some embodiments is the isolated monovalent antigen-binding construct described herein, wherein said construct possesses a higher degree of at least one of the ADCC, ADCP and CDC of a corresponding bivalent antigen-binding construct with two antigen binding polypeptide construct. In some embodiments is the isolated monovalent antigen-binding construct described herein, wherein said construct possesses at least about 105% of at least one of the ADCC, ADCP and CDC of a corresponding bivalent antigen-binding construct with two antigen binding polypeptide construct. In some embodiments is an isolated monovalent antigen-binding construct described herein, wherein said construct possesses greater than about 110% of at least one of the ADCC, ADCP and CDC of a corresponding bivalent antigen-binding construct with two antigen binding polypeptide constructs.

HER2 Binding Constructs

In some embodiments the monovalent antigen-binding construct described herein is designed to target a cell expressing HER2 and the antigen-binding polypeptide construct binds HER2. HER2 is proto-oncogene belonging to the human epidermal growth factor receptor (EGFR) family and is often overexpressed in a subset of breast cancers. The HER2 protein is also referred as the product of the neu gene, EGFR2, CD340, ErbB2 and p185. In some embodiments, the antigen-binding polypeptide construct binds HER2 and the target cell is a low, medium or high HER2 expressing cell. In an embodiment, the antigen-binding polypeptide construct binds HER2 and the target cell is a low HER2 expressing cell. In another embodiment, the antigen-binding polypeptide construct binds HER2 and the target cell is a low HER2 expressing cell with decreased binding to bivalent HER2 binding antibodies. In a further embodiment, the antigen-binding polypeptide construct binds HER2 and the target cell is a low HER2 expressing cell with decreased binding to trastuzumab. In an embodiment, the antigen-binding polypeptide construct binds HER2 and the target cell is a cancer cell. In a certain embodiment, the antigen-binding polypeptide construct binds HER2 and the target cell is a breast cancer cell.

In some embodiments of the monovalent antigen-binding construct described herein, the dimeric Fc polypeptide construct is heterodimeric. In some embodiments of the monovalent antigen-binding construct described, the antigen-binding polypeptide construct binds HER2. In some embodiments, the antigen-binding polypeptide construct binds at least one HER2 extracellular domain. In certain embodiments, the extracellular domain is at least one of ECD1, ECD2, ECD3 and ECD4. In certain embodiments, the antigen-binding polypeptide construct binds HER2 expressed by a target cell which is a low, medium or high HER2 expressing cell. In certain embodiments, the HER2 expressing cell displays decreased binding to bivalent HER2 binding antibodies. In an embodiment, the antigen-binding polypeptide construct binds HER2 and the target cell is at least one of an estrogen receptor negative cell, a progesterone receptor negative cell and anti-HER2 antibody resistant tumor cell with decreased binding to bivalent HER2 binding antibodies.

In some embodiments of the monovalent antigen-binding construct described herein, the dimeric Fc polypeptide construct is heterodimeric. In certain embodiments of the monovalent antigen-binding construct described herein, the monovalent antigen binding polypeptide construct is a Fab fragment, an scFv, and sdAb, an antigen binding peptide or a protein domain capable of binding the antigen. In some embodiments is provided an isolated monovalent antigen-binding construct as described herein wherein the monovalent antigen binding polypeptide construct is a Fab fragment comprising a heavy chain polypeptide and a light chain polypeptide.

Provided herein is an isolated monovalent antigen-binding construct that binds HER2 comprising: an antigen binding polypeptide construct which monovalently binds HER2; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said antigen-binding construct is anti-proliferative and is internalized by a target cell, wherein said construct displays an increase in binding density and Bmax (maximum binding) to HER2 displayed on the target cell as compared to a corresponding bivalent antigen-binding construct which binds HER2, and wherein said construct displays at least one of higher ADCC, higher ADCP and higher CDC as compared to said corresponding bivalent HER2 binding antigen-binding constructs.

Provided in certain embodiments is an isolated monovalent antigen-binding construct that binds HER2 on a target cell with low HER2 expression, comprising: an antigen binding polypeptide construct which monovalently binds HER2; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said antigen-binding construct is anti-proliferative and is internalized by a target cell, wherein said construct displays an increase in binding density and Bmax (maximum binding) to HER2 displayed on the target cell as compared to a corresponding bivalent antigen-binding construct which binds HER2, and wherein said construct displays at least one of higher ADCC, higher ADCP and higher CDC as compared to said corresponding bivalent HER2 binding antigen-binding constructs. In certain embodiments, the target cell with low HER2 expression is a cancer cell. In some embodiments, the target cell with low HER2 expression is a breast cancer cell.

Provided herein is an isolated monovalent antigen-binding construct that binds HER2 comprising: an antigen binding polypeptide construct which monovalently binds HER2 at an extracellular domain (ECD) which is at least one of ECD 1, ECD 2 and ECD 3-4; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said antigen-binding construct is anti-proliferative and is internalized by a target cell, wherein said construct displays an increase in binding density and Bmax (maximum binding) to at least one of HER2 ECD 1, 2, and 3-4 displayed on the target cell as compared to a corresponding bivalent antigen-binding construct which binds HER2, and wherein said construct displays at least one of higher ADCC, higher ADCP and higher CDC as compared to said corresponding bivalent HER3 binding antigen-binding constructs.

Provided herein is an isolated monovalent antigen-binding construct that binds HER2 comprising: an antigen binding polypeptide construct which monovalently binds HER2 at an extracellular domain (ECD) which is at least one of ECD 1, ECD 2, ECD 3 and ECD4; and a dimeric Fc polypeptide construct comprising two monomeric Fc polypeptides each comprising a CH3 domain, wherein one said monomeric Fc polypeptide is fused to at least one polypeptide from the antigen-binding polypeptide construct; wherein said antigen-binding construct is anti-proliferative and is internalized by a target cell, wherein said construct displays an increase in binding density and Bmax (maximum binding) to at least one of HER2 ECD 1, 2, 3 and 4 displayed on the target cell as compared to a corresponding bivalent antigen-binding construct which binds HER2, and wherein said construct displays at least one of higher ADCC, higher ADCP and higher CDC as compared to said corresponding bivalent HER2 binding antigen-binding constructs.

In an embodiment is the isolated monovalent antigen-binding construct described herein, wherein the antigen-binding construct inhibits target cell proliferation. In some embodiments is an isolated monovalent antigen-binding construct described herein wherein said monovalent HER2 binding polypeptide construct is at least one of Fab, an scFv, an sdAb, or a polypeptide. In some embodiments is the isolated monovalent antigen-binding construct described herein, wherein said construct possesses a higher degree of at least one of the ADCC, ADCP and CDC of a corresponding bivalent antigen-binding construct with two antigen binding polypeptide construct. In some embodiments is the isolated monovalent antigen-binding construct described herein, wherein said construct possesses at least about 105% of at least one of the ADCC, ADCP and CDC of a corresponding bivalent antigen-binding construct with two antigen binding polypeptide construct. In some embodiments is an isolated monovalent antigen-binding construct described herein, wherein said construct possesses greater than about 110% of at least one of the ADCC, ADCP and CDC of a corresponding bivalent antigen-binding construct with two antigen binding polypeptide constructs.

Selection of Target Cells

The target cell is selected based on the intended use of the monovalent antigen-binding construct. In one embodiment, the target cell is a cell which is activated or amplified in a cancer, an infectious disease, an autoimmune disease, or in an inflammatory disease.

In one embodiment, where the monovalent antigen-binding construct is intended for use in the treatment of cancer, the target cell is derived from a tumor that exhibits EGFR and/or HER2 3+ overexpression. In one embodiment, the target cell is derived from a tumor that exhibits EGFR and/or HER2 low expression. In one embodiment, the target cell is derived from a tumor that exhibits EGFR and/or HER2 resistance. In one embodiment, the target cell is derived from a tumor that is a triple negative (ER/PR/HER2) tumor.

In embodiments where the monovalent antigen-binding construct is intended for use in the treatment of cancer, the target cell is a cancer cell line that is representative of EGFR and/or HER2 3+ overexpression. In one embodiment, the target cell is a cancer cell line that is representative of EGFR and/or HER2 low expression. In one embodiment, the target cell is a cancer cell line that is representative of EGFR and/or HER2 resistance. In one embodiment, the target cell is a cancer cell line that is representative of breast cancer triple negative e.g., MDA-MD-231 cells.

In one embodiment, the monovalent antigen-binding construct according to the invention is designed to target a breast cancer cell or epithelial cell-derived cancer cell.

In one embodiment, the monovalent antigen-binding construct described herein is designed to target Gastric and Esophageal Adenocarcinomas. Exemplary histologic types include: HER2 positive proximal gastric carcinomas with intestinal phenotype and HER2 positive distal diffuse gastric carcinomas. Exemplary classes of gastric cancer cells include but are not limited to (N-87, OE-19, SNU-216 and MKN-7).

In another embodiment, a monovalent antigen-binding construct described herein is designed to target Metastatic HER2+ Breast Cancer Tumors in the Brain. Exemplary classes of gastric cancer cells include but are not limited to BT474.

In embodiments where the monovalent antigen-binding construct according to the invention is designed to target a cancer cell, the antigen-binding polypeptide construct monovalently binds an antigen that is expressed on the surface of the cancer cell. Suitable antigens include, but are not limited to EGFR and/or HER2. In one embodiment, the epitope that the antigen-binding polypeptide construct binds to an extracellular domain of the target antigen on the target cell.

In embodiments where the monovalent antigen-binding construct comprises an antigen-binding polypeptide construct that binds to EGFR, the antigen-binding polypeptide construct binds to EGFR or to a particular domain or epitope of EGFR. In one embodiment, the antigen-binding polypeptide construct binds to an extracellular domain of EGFR.

Selection of Antibodies

In embodiments where the monovalent antigen-binding construct comprises an antigen-binding polypeptide construct that binds to EGFR, the antigen-binding polypeptide construct can be derived from known anti-EGFR antibodies or anti-EGFR binding domains in various formats including Fab fragments, scFvs, and sdab. In certain embodiments the antigen-binding polypeptide construct can be derived from humanized, or chimeric versions of these antibodies. In one embodiment, the antigen-binding polypeptide construct is derived from a Fab fragment of trastuzumab, pertuzumab, cetuximab, or humanized versions thereof. In one embodiment, the antigen-binding polypeptide construct is derived from an scFv. In one embodiment, the antigen-binding polypeptide construct is derived from an sdab.

FC

The antigen-binding constructs can comprise an Fc, e.g., a dimeric Fc.

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, Md., 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence.

An Fc domain comprises either a CH3 domain or a CH3 and a CH2 domain. The CH3 domain comprises two CH3 sequences, one from each of the two Fc polypeptides of the dimeric Fc. The CH2 domain comprises two CH2 sequences, one from each of the two Fc polypeptides of the dimeric Fc.

In some aspects, the Fc comprises at least one or two CH3 sequences. In some aspects, the Fc is coupled, with or without one or more linkers, to a first antigen-binding construct and/or a second antigen-binding construct. In some aspects, the Fc is a human Fc. In some aspects, the Fc is a human IgG or IgG1 Fc. In some aspects, the Fc is a heterodimeric Fc. In some aspects, the Fc comprises at least one or two CH2 sequences.

In some aspects, the Fc comprises one or more modifications in at least one of the CH3 sequences. In some aspects, the Fc comprises one or more modifications in at least one of the CH2 sequences. In some aspects, an Fc is a single polypeptide, e.g., a dimeric Fc where the two polypeptides of the dimer are linked by a polypeptide linker. In some aspects, an Fc is multiple peptides, e.g., two polypeptides.

In some aspects, an Fc is an Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

Modified CH3 Domains

In some aspects, the antigen-binding construct described herein comprises a heterodimeric Fc comprising a modified CH3 domain that has been asymmetrically modified. The heterodimeric Fc can comprise two heavy chain constant domain polypeptides: a first Fc polypeptide and a second Fc polypeptide, which can be used interchangeably provided that Fc comprises one first Fc polypeptide and one second Fc polypeptide. Generally, the first Fc polypeptide comprises a first CH3 sequence and the second Fc polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table A provides the amino acid sequence of the human IgG1 Fc sequence, corresponding to amino acids 231 to 447 of the full-length human IgG1 heavy chain. The CH3 sequence comprises amino acid 341-447 of the full-length human IgG1 heavy chain.

Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a mutant sequence shown in Table A. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

TABLE A

| IgG1 Fc sequences | | |
|---|---|---|
| Human IgG1 Fc sequence 231-447 (EU-numbering) | APELLGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALPAPI EKTISKAKGQPREPQVYTLPPSRDELTKNQVSLT CLVKGFYPSDIAVEWESNGQPENNYKTTPPVLDS DGSFFLYSKLTVDKSRWQQGNVFSCSVMHEALHN HYTQKSLSLSPGK (SEQ ID NO: 40) | |
| Variant IgG1 Fc sequence (231-447) | Chain | Mutations |
| 1 | A | L351Y_F405A_Y407V |
| 1 | B | T366L_K392M_T394W |
| 2 | A | L351Y_F405A_Y407V |
| 2 | B | T366L_K392L_T394W |
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from L351Y, F405A, and Y407V, and the second CH3 sequence having one or more amino acid modifications selected from T366L, T366I, K392L, K392M, and T394W.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351, F405 and Y407, and a second CH3 sequence having amino acid modifications at position T366, K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394 and one of said first and second CH3 sequences further comprising amino acid modification of D399R or D399K and the other CH3 sequence comprising one or more of T411E, T411D, K409E, K409D, K392E and K392D. In another embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, wherein one or both of said CH3 sequences further comprise the amino acid modification of T350V.

In one embodiment, a heterodimeric Fc comprises a modified CH3 domain comprising the following amino acid modifications, where "A" represents the amino acid modifications to the first CH3 sequence, and "B" represents the amino acid modifications to the second CH3 sequence: A:L351Y_F405A_Y407V, B:T366L_K392M_T394W, A:L351Y_F405A_Y407V, B:T366L_K392L_T394W, A:T350V_L351Y_F405A_Y407V, B:T350V_T366L_K392L_T394W, A:T350V_L351Y_F405A_Y407V, B:T350V_T366L_K392M_T394W, A:T350V_L351Y_S400E_F405A_Y407V, and/or B:T350V_T366L_N390R_K392M_T394W.

The one or more asymmetric amino acid modifications can promote the formation of a heterodimeric Fc in which the heterodimeric CH3 domain has a stability that is comparable to a wild-type homodimeric CH3 domain. In an embodiment, the one or more asymmetric amino acid modifications promote the formation of a heterodimeric Fc domain in which the heterodimeric Fc domain has a stability that is comparable to a wild-type homodimeric Fc domain. In an embodiment, the one or more asymmetric amino acid modifications promote the formation of a heterodimeric Fc domain in which the heterodimeric Fc domain has a stability observed via the melting temperature (Tm) in a differential scanning calorimetry study, and where the melting temperature is within 4° C. of that observed for the corresponding symmetric wild-type homodimeric Fc domain. In some aspects, the Fc comprises one or more modifications in at least one of the $C_{H3}$ sequences that promote the formation of a heterodimeric Fc with stability comparable to a wild-type homodimeric Fc.

In one embodiment, the stability of the CH3 domain can be assessed by measuring the melting temperature of the CH3 domain, for example by differential scanning calorimetry (DSC). Thus, in a further embodiment, the CH3 domain has a melting temperature of about 68° C. or higher. In another embodiment, the CH3 domain has a melting temperature of about 70° C. or higher. In another embodiment, the CH3 domain has a melting temperature of about 72° C. or higher. In another embodiment, the CH3 domain has a melting temperature of about 73° C. or higher. In another embodiment, the CH3 domain has a melting temperature of about 75° C. or higher. In another embodiment, the CH3 domain has a melting temperature of about 78° C. or higher. In some aspects, the dimerized CH3 sequences have a melting temperature (Tm) of about 68, 69, 70, 71, 72, 73, 74, 75, 76, 77, 77.5, 78, 79, 80, 81, 82, 83, 84, or 85° C. or higher.

In some embodiments, a heterodimeric Fc comprising modified CH3 sequences can be formed with a purity of at least about 75% as compared to homodimeric Fc in the expressed product. In another embodiment, the heterodimeric Fc is formed with a purity greater than about 80%. In another embodiment, the heterodimeric Fc is formed with a purity greater than about 85%. In another embodiment, the heterodimeric Fc is formed with a purity greater than about 90%. In another embodiment, the heterodimeric Fc is formed with a purity greater than about 95%. In another embodiment, the heterodimeric Fc is formed with a purity greater than about 97%. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

Additional methods for modifying monomeric Fc polypeptides to promote heterodimeric Fc formation are described in International Patent Publication No. WO 96/027011 (knobs into holes), in Gunasekaran et al. (Gunasekaran K. et al. (2010) J Biol Chem. 285, 19637-46, electrostatic design to achieve selective heterodimerization), in Davis et al. (Davis, J H. et al. (2010) Prot Eng Des Sel; 23(4): 195-202, strand exchange engineered domain (SEED) technology), and in Labrijn et al [Efficient generation of stable bispecific IgG1 by controlled Fab-arm exchange. Labrijn A F, Meesters J I, de Goeij B E, van den Bremer E T, Neijssen J, van Kampen M D, Strumane K, Verploegen S, Kundu A, Gramer M J, van Berkel P H, van de Winkel J G, Schuurman J, Parren P W. Proc Natl Acad Sci USA. 2013 Mar. 26; 110(13):5145-50.

In some embodiments an isolated antigen-binding construct described herein comprises an antigen binding polypeptide construct which binds an antigen; and a dimeric Fc that has superior biophysical properties like stability and ease of manufacture relative to an antigen binding construct which does not include the same dimeric Fc. A number of amino acid modifications in the Fc region are known in the art for selectively altering the affinity of the Fc for different Fcgamma receptors. In some aspects, the Fc comprises one or more modifications to promote selective binding of Fc-gamma receptors. These types of amino acid modifications are typically located in the CH2 domain or in the hinge region of antigen-binding construct.

CH2 Domains

The CH2 domain of an Fc is amino acid 231-340 of the sequence shown in Table A. Exemplary mutations are listed below:

S298A/E333A/K334A, S298A/E333A/K334A/K326A (Lu Y, Vernes J M, Chiang N, et al. J Immunol Methods. 2011 Feb. 28; 365(1-2):132-41);

F243L/R292P/Y300L/V3051/P396L, F243L/R292P/Y300L/L235V/P396L (Stavenhagen J B, Gorlatov S, Tuaillon N, et al. Cancer Res. 2007 Sep. 15; 67(18): 8882-90; Nordstrom J L, Gorlatov S, Zhang W, et al. Breast Cancer Res. 2011 Nov. 30; 13(6):R123);

F243L (Stewart R, Thom G, Levens M, et al. Protein Eng Des Sel. 2011 September; 24(9):671-8.), S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45(15):3926-33);

S239D/D265S/S298A/I332E, S239E/S298A/K326A/A327H, G237F/S298A/A330L/I332E, S239D/I332E/S298A, S239D/K326E/A330L/I332E/S298A, G236A/S239D/D270L/I332E, S239E/S267E/H268D, L234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) lists mutations on page 283.

In some embodiments a CH2 domain comprises one or more asymmetric amino acid modifications. In some embodiments a CH2 domain comprises one or more asymmetric amino acid modifications to promote selective binding of a FcγR. In some embodiments the CH2 domain allows for separation and purification of an isolated construct described herein. Additional modifications to improve effector function.

In some embodiments an antigen binding construct described herein can be modified to improve its effector function. Such modifications are known in the art and include afucosylation, or engineering of the affinity of the Fc towards an activating receptor, mainly FCGR3a for ADCC, and towards C1q for CDC. The following Table B1 summarizes various designs reported in the literature for effector function engineering.

Thus, in one embodiment, a construct described herein can include a dimeric Fc that comprises one or more amino acid modifications as noted in Table B1 that confer improved effector function. In another embodiment, the construct can be afucosylated to improve effector function.

TABLE B1

CH2 domains and effector function engineering.

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Fc modifications reducing FcγR and/or complement binding and/or effector function are known in the art. Recent publications describe strategies that have been used to engineer antibodies with reduced or silenced effector activity (see Strohl, W R (2009), Curr Opin Biotech 20:685-691, and Strohl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO 2006/105338 (Xencor), US Patent Publication No. 2012/0225058 (Xencor), US Patent Publication No. 2012/0251531 (Genentech), and Strop et al ((2012) J. Mol. Biol. 420: 204-219) describe specific modifications to reduce FcγR or complement binding to the Fc.

Specific, non-limiting examples of known amino acid modifications include those identified in the following table:

TABLE C modifications to reduce FcγR or complement binding to the Fc

| Company | Mutations |
|---|---|
| GSK | N297A |
| Ortho Biotech | L234A/L235A |
| Protein Design labs | IGG2 V234A/G237A |
| Wellcome Labs | IGG4 L235A/G237A/E318A |
| GSK | IGG4 S228P/L236E |
| Alexion | IGG2/IGG4combo |
| Merck | IGG2 H268Q/V309L/A330S/A331S |
| Bristol-Myers | C220S/C226S/C229S/P238S |
| Seattle Genetics | C226S/C229S/E3233P/L235V/L235A |
| Amgen | *E.coli* production, non glyco |
| Medimune | L234F/L235E/P331S |
| Trubion | Hinge mutant, possibly C226S/P230S |

In one embodiment, the Fc comprises at least one amino acid modification identified in the above table. In another embodiment the Fc comprises amino acid modification of at least one of L234, L235, or D265. In another embodiment, the Fc comprises amino acid modification at L234, L235 and D265. In another embodiment, the Fc comprises the amino acid modification L234A, L235A and D265S.

FcRn Binding and PK Parameters

As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport. Thus, in one embodiment, the antigen-binding constructs of the described herein are able to bind FcRn.

Linkers

The antigen-binding constructs described herein can include one or more antigen binding polypeptide constructs operatively coupled to an Fc described herein. In some aspects, an Fc is coupled to the one or more antigen binding polypeptide constructs with one or more linkers. In some aspects, Fc is directly coupled to the one or more antigen binding polypeptide constructs. In some aspects, Fc is coupled to the heavy chain of each antigen binding polypeptide by a linker.

In some aspects, the one or more linkers are one or more polypeptide linkers. In some aspects, the one or more linkers comprise one or more IgG1 hinge regions.

Additional Modifications of Antigen Binding Constructs to Improve a Function

In some embodiments is an isolated monovalent antigen-binding construct described herein comprising an antigen-binding polypeptide construct which monovalently binds an antigen; and a dimeric Fc polypeptide construct comprising a CH3 domain and further comprising a variant CH2 domain. In some embodiments the variant CH2 domain is comprising asymmetric amino acid modifications to promote selective binding of a FcγR. In some embodiment the variant CH2 domain allows for separation and purification of the isolated monovalent antibody described herein.

In some embodiment is an isolated monovalent antigen-binding construct described herein comprising an antigen binding polypeptide that monovalently binds an antigen; and wherein the antigen binding polypeptide is fused via a polypeptide to a monomeric Fc polypeptide comprising CH2 and CH3 domains.

In some embodiment is an isolated monovalent antigen-binding construct described herein comprising an antigen binding polypeptide that monovalently binds an antigen; and wherein the antigen binding polypeptide is a Fab, wherein the heavy chain of the Fab is fused via a polypeptide to a monomeric Fc polypeptide comprising CH2 and CH3 domains and the light chain of the Fab is fused via a polypeptide to a second monomeric Fc polypeptide comprising CH2 and CH3 domains.

In some embodiment is an isolated monovalent antigen-binding construct described herein comprising an antigen binding polypeptide that monovalently binds an antigen; and where in the antigen binding polypeptide is fused to a monomeric Fc polypeptide comprising CH2 and CH3 domains and a second polypeptide incapable of binding to any antigen; wherein the second polypeptide is fused to the second monomeric Fc polypeptide comprising the CH2 and CH3 domains; wherein the two monomeric Fc polypeptides pair to form a dimer.

In some embodiments the monovalent antigen-binding constructs according to the invention may be modified to improve their effector function. Such modifications are known in the art and include afucosylation, or engineering of the affinity of the Fc portion of antibodies towards the activating receptors, mainly FCGR3a for ADCC, and towards C1q, for CDC. The following table A3 summarizes the different designs reported in the literature for effector function engineering.

TABLE A3

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Thus, in one embodiment, the monovalent antigen-binding constructs can include a dimeric Fc polypeptide construct that comprises one or more amino acid modifications as noted in the above table that confer improved effector function. In another embodiment, the monovalent antigen-binding construct are afucosylated to improve effector function.

Methods of producing antigen-binding constructs with little or no fucose on the Fcγ glycolsylation site (Asn 297 EU numbering) without altering the amino acid sequence are well known in the art. The GlymaX® technology (ProBioGen AG) is based on the introduction of a gene for an enzyme which deflects the cellular pathway of fucose biosynthesis into cells used for antigen-binding construct production. This prevents the addition of the sugar "fucose" to the N-linked antibody carbohydrate part by antigen-binding construct-producing cells. (von Horsten et al. (2010) *Glycobiology.* 2010 December; 20 (12):1607-18. Another approach to obtaining antigen-binding constructs with lowered levels of fucosylation can be found in U.S. Pat. No. 8,409,572, which teaches selecting cell lines for antigen-binding construct production for their ability to yield lower levels of fucosylation on antigen-binding constructs Antigen-binding constructs can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

In instances where it is desirable to increase the affinity of the antigen-binding polypeptide construct for its cognate antigen, methods known in the art can be used to increase the affinity of the antigen-binding polypeptide construct for its antigen. Examples of such methods are described in the following references, Birtalan et al. (2008) *JMB* 377, 1518-1528; Gerstner et al. (2002) *JMB* 321, 851-862; Kelley et al. (1993) *Biochem* 32(27), 6828-6835; Li et al. (2010) *JBC* 285(6), 3865-3871, and Vajdos et al. (2002) *JMB* 320, 415-428.

One example, of such a method is affinity maturation. One exemplary method for affinity maturation of HER2 antigen-binding domains is described as follows. Structures of the trastuzumab/HER2 (PDB code 1N8Z) complex and pertuzumab/HER2 complex (PDB code 1S78) are used for modeling. Molecular dynamics (MD) can be employed to evaluate the intrinsic dynamic nature of the WT complex in an aqueous environment. Mean field and dead-end elimination methods along with flexible backbones can be used to optimize and prepare model structures for the mutants to be screened. Following packing a number of features will be scored including contact density, clash score, hydrophobicity and electrostatics. Generalized Born method will allow accurate modeling of the effect of solvent environment and compute the free energy differences following mutation of specific positions in the protein to alternate residue types. Contact density and clash score will provide a measure of complementarity, a critical aspect of effective protein packing. The screening procedure employs knowledge-based potentials as well as coupling analysis schemes relying on pair-wise residue interaction energy and entropy computations. Literature mutations known to enhance HER2 binding, and combinations of thereof are summarized in the following tables:

TABLE A4

Trastuzumab mutations known to increase binding to HER2 for the Trastuzumab-HER2 system.

| Mutation | Reported Improvement |
|---|---|
| H_D102W (H_D98W) | 3.2X |
| H_D102Y | 3.1X |
| H_D102K | 2.3X |
| H_D102T | 2.2X |
| H_N55K | 2.0X |
| H_N55T | 1.9X |
| L_H91F | 2.1X |
| L_D28R | 1.9X |

TABLE A5

Pertuzumab mutations known to increase binding to HER2 for the Pertuzumab-HER2 system.

| Mutation | Reported Improvement |
|---|---|
| L_I31A | 1.9X |
| L_Y96A | 2.1X |
| L_Y96F | 2.5X |
| H_T30A | 2.1X |
| H_G56A | 8.3X |
| H_F63V | 1.9X |

The monovalent antigen-binding constructs described herein are internalized once they bind to the target cell. In one embodiment, the monovalent antigen-binding constructs are internalized to a similar degree compared to the corresponding monospecific bivalent antigen-binding constructs. In some embodiments, the monovalent antigen-binding constructs are internalized more efficiently compared to the corresponding monospecific bivalent antigen-binding constructs.

Dissociation Constant ($K_D$) and Maximal Binding (Bmax)

In some embodiments, an antigen binding construct is described by functional characteristics including but not limited to a dissociation constant and a maximal binding.

The term "dissociation constant (KD)" as used herein, is intended to refer to the equilibrium dissociation constant of a particular ligand-protein interaction. As used herein, ligand-protein interactions refer to, but are not limited to protein-protein interactions or antibody-antigen interactions. The KD measures the propensity of two proteins (e.g. AB) to dissociate reversibly into smaller components (A+B), and is define as the ratio of the rate of dissociation, also called the "off-rate ($k_{off}$)", to the association rate, or "on-rate ($k_{on}$)". Thus, KD equals $k_{off}/k_{on}$ and is expressed as a molar concentration (M). It follows that the smaller the KD, the stronger the affinity of binding. Therefore, a KD of 1 mM indicates weak binding affinity compared to a KD of 1 nM. KD values for antigen binding constructs can be determined using methods well established in the art. One method for determining the KD of an antigen binding construct is by using surface plasmon resonance (SPR), typically using a biosensor system such as a Biacore® system. Isothermal titration calorimetry (ITC) is another method that can be used to determine.

The binding characteristics of an antigen binding construct can be determined by various techniques. One of which is the measurement of binding to target cells expressing the antigen by flow cytometry (FACS, Fluorescence-activated cell sorting). Typically, in such an experiment, the target cells expressing the antigen of interest are incubated with antigen binding constructs at different concentrations, washed, incubated with a secondary agent for detecting the antigen binding construct, washed, and analyzed in the flow cytometer to measure the median fluorescent intensity (MFI) representing the strength of detection signal on the cells, which in turn is related to the number of antigen binding constructs bound to the cells. The antigen binding construct concentration vs. MFI data is then fitted into a saturation binding equation to yield two key binding parameters, Bmax and apparent KD.

Apparent KD, or apparent equilibrium dissociation constant, represents the antigen binding construct concentration at which half maximal cell binding is observed. Evidently, the smaller the KD value, the smaller antigen binding construct concentration is required to reach maximum cell binding and thus the higher is the affinity of the antigen binding construct. The apparent KD is dependent on the conditions of the cell binding experiment, such as different receptor levels expressed on the cells and incubation conditions, and thus the apparent KD is generally different from the KD values determined from cell-free molecular experiments such as SPR and ITC. However, there is generally good agreement between the different methods.

The term "Bmax", or maximal binding, refers to the maximum antigen binding construct binding level on the cells at saturating concentrations of antigen binding construct. This parameter can be reported in the arbitrary unit MFI for relative comparison, or converted into an absolute value corresponding to the number of antigen binding constructs bound to the cell with the use of a standard curve. In some embodiments, the antigen binding constructs display a Bmax that is 1.1, 1.2, 1.3, 1.4, 1.5, 1.6, 1.7, 1.8, 1.9, or 2.0 times the Bmax of a reference antigen binding construct.

For the antigen binding constructs described herein, the clearest separation in Bmax versus FSA occurs at saturating concentrations and where Bmax can no longer be increased with a FSA. The significance is less at non-saturating concentrations. In one embodiment the increase in Bmax and KD of the antigen binding construct compared to a reference antigen binding construct is independent of the level of target antigen expression on the target cell.

In some embodiments is an isolated antigen binding construct described herein, wherein said antigen binding construct displays an increase in Bmax (maximum binding) to a target cell displaying said antigen as compared to a corresponding reference antigen binding construct. In some embodiments said increase in Bmax is at least about 125% of the Bmax of the corresponding reference antigen binding construct. In certain embodiments, the increase in Bmax is at least about 150% of the Bmax of the corresponding reference antigen binding construct. In some embodiments, the increase in Bmax is at least about 200% of the Bmax of the corresponding reference antigen binding construct. In some embodiments, the increase in Bmax is greater than about 110% of the Bmax of the corresponding reference antigen binding construct.

Antigen Binding Constructs and Antibody Drug Conjugates (ADC)

In certain embodiments an antigen binding construct is conjugated to a drug, e.g., a toxin, a chemotherapeutic agent, an immune modulator, or a radioisotope. Several methods of preparing ADCs (antibody drug conjugates or antigen binding construct drug conjugates) are known in the art and are described in U.S. Pat. No. 8,624,003 (pot method), U.S. Pat. No. 8,163,888 (one-step), and U.S. Pat. No. 5,208,020 (two-step method) for example.

In some embodiments, the drug is selected from a maytansine, auristatin, calicheamicin, or derivative thereof. In other embodiments, the drug is a maytansine selected from DM1 and DM4. Further examples are described below.

In some embodiments the drug is conjugated to the isolated antigen binding construct with an SMCC linker (DM1), or an SPDB linker (DM4). Additional examples are described below. The drug-to-antigen binding protein ratio (DAR) can be, e.g., 1.0 to 6.0 or 3.0 to 5.0 or 3.5-4.2.

In some embodiments the antigen binding construct is conjugated to a cytotoxic agent. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins such as small molecule toxins or enzymatically active toxins of bacterial, fungal, plant or animal origin, including fragments and/or variants thereof. Further examples are described below.

Drugs

Examples of drugs or payloads used in various embodiments of ADCs include DM1 (maytansine, N2'-deacetyl-N2'-(3-mercapto-1-oxopropyl)- or N2'-deacetyl-N2'-(3-mercapto-1-oxopropyl)-maytansine), mc-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl]amino]propyl]-1-pyrrolidinyl]-1-[(1S)-1-methylpropyl]-4-oxobutyl]-N-methyl-(9Cl)-L-valinamide), mc-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino)heptanoyl-(αR, βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino]phenyl]methoxy]carbonyl]-N-meth yl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives.

Maytansinoid Drug Moieties

In some embodiments the drug is a maytansinoid. Maytansine compounds inhibit cell proliferation by inhibiting the formation of microtubules during mitosis through inhibition of polymerization of the microtubulin protein, tubulin (Remillard et al (1975) Science 189:1002-1005; U.S. Pat. No. 5,208,020). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207. Maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamitocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions Exemplary maytansinoid drug moieties also include those having modifications such as: C-9-SH, prepared by the reaction of maytansinol with H2S or P2S5 (U.S. Pat. No. 4,424,219); C-14-alkoxymethyl(demethoxy/CH2 OR)(U.S. Pat. No. 4,331,598); C-14-hydroxymethyl or acyloxymethyl (CH2OH or CH2OAc) prepared from *Nocardia* (U.S. Pat. No. 4,450,254); C-15-hydroxy/acyloxy, prepared by the conversion of maytansinol by *Streptomyces*(U.S. Pat. No. 4,364,866); C-15-methoxy, isolated from *Trewia nudlflora* (U.S. Pat. Nos. 4,313,946 and 4,315,929); C-18-N-demethyl, prepared by the demethylation of maytansinol by *Streptomyces* (U.S. Pat. Nos. 4,362,663 and 4,322,348); and 4,5-deoxy, prepared by the titanium trichloride/LAH reduction of maytansinol (U.S. Pat. No. 4,371,533).

Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

All stereoisomers of the maytansinoid drug moiety are contemplated for the compounds of the invention, i.e. any combination of R and S configurations at the chiral carbons of D. Embodiments of the ADC include DM1, DM3, DM4 (see US20090202536).

Steric hindrance conferred by alkyl groups such as the methyl groups on the carbon adjacent to the sulfur atom of DM3 and DM4 may affect the rate of intracellular cleavage of the ADC (US 2004/0235840 A1). The variable alkyl unit (CR2)m may therefore affect potency, efficacy, and safety/toxicity in vitro and in vivo.

Auristatins

In some embodiments, the drug is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Pat. Nos. 6,884,869, 7,098,308, 7,256,257, 7,423,116, 7,498,298 and 7,745,394, each of which is incorporated by reference herein in its entirety and for all purposes.

Auristatins have been shown to interfere with microtubule dynamics and nuclear and cellular division and have anticancer activity. Auristatins of the present invention bind tubulin and can exert a cytotoxic or cytostatic effect on a 5T4 expressing cell or cell line. There are a number of different assays, known in the art, that can be used for determining whether an auristatin or resultant antibody-drug conjugate exerts a cytostatic or cytotoxic effect on a desired cell or cell line. Methods for determining whether a compound binds tubulin are known in the art. See, for example, Muller et al., Anal. Chem 2006, 78, 4390-4397; Hamel et al., Molecular Pharmacology, 1995 47: 965-976; and Hamel et al., The Journal of Biological Chemistry, 1990 265:28, 17141-17149.

Chemotherapeutic Agents

In some embodiments the antigen binding construct is conjugated to a chemotherapeutic agent. Examples include but are not limited to Cisplantin and Lapatinib. A "chemotherapeutic agent" is a chemical compound useful in the treatment of cancer.

Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK7; razoxane; sizofiran; spirogermanium; tenuazonic acid; triaziquone; 2, 2',2'=-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Conjugate Linkers

In some embodiments, the drug is linked to the antigen binding construct, e.g., antibody, by a linker. Attachment of a linker to an antibody can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (mc-Val-Cit-PABA) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

A linker can include a group for linkage to the antibody. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio). See generally Wong, Chemistry of Protein Conjugation and Cross-linking; CRC Press, Inc., Boca Raton, 1991.

In one embodiment, covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Bioconjugate Techniques, Third Edition by Greg T. Hermanson, Academic Press 2013 ISBN-13: 978-0123822390).

In another embodiment, the linker may be substituted with groups which modulated solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

In another embodiment, a linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker can react with an electrophilic group on an antibody and form a covalent bond to an antibody unit. Useful nucleophilic groups on a liner include, but are not limited to, hydrazide, oxime, amino, hydrazine, thiosemicarbazone, hydrazine carboxylate, and arylhydrazide. The electrophilic group on an antibody provides a convenient site for attachment to a linker.

Linkers can be peptidic, comprising one or more amino acid units. Peptide linker reagents may be prepared by solid phase or liquid phase synthesis methods (E. Schröder and K. Lübke, The Peptides, volume 1, pp 76-136 (1965) Academic Press) that are well known in the field of peptide chemistry, including t-BOC chemistry (Geiser et al "Automation of solid-phase peptide synthesis" in Macromolecular Sequencing and Synthesis, Alan R. Liss, Inc., 1988, pp. 199-218) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

The compounds expressly contemplate, but are not limited to, ADC prepared with cross-linker reagents: BMPEO, BMPS, EMCS, GMBS, HBVS, LC-SMCC, MBS, MPBH, SBAP, SPDB, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)2, and BM(PEO)3, which are commercially available from Pierce Biotechnology, Inc., Customer Service Department, P.O. Box 117, Rockford, Ill. 61105 U.S.A, U.S.A 1-800-874-3723, International +815-968-0747. See pages 467-498, 2003-2004 Applications Handbook and Catalog.

Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, maytansinoid drug moiety, or linker intermediate include iodoacetamide, bromoacetamide, vinyl pyridine, disulfide, pyridyl disulfide, isocyanate, and isothiocyanate.

Useful linker reagents can also be obtained via other commercial sources, such as Molecular Biosciences Inc. (Boulder, Colo.), or synthesized in accordance with procedures described in Told et al (2002) J. Org. Chem. 67:1866-1872; U.S. Pat. No. 6,214,345 to Firestone et al; WO 02/088172; US 2003130189; US2003096743; WO 03/026577; WO 03/043583; and WO 04/032828.

The linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Preparation of ADCs

The ADC may be prepared by several routes, employing organic chemistry reactions, conditions, and reagents known to those skilled in the art, including: (1) reaction of a nucleophilic group or an electrophilic group of an antibody with a bivalent linker reagent, to form antibody-linker intermediate Ab-L, via a covalent bond, followed by reaction with an activated drug moiety D; and (2) reaction of a nucleophilic group or an electrophilic group of a drug moiety with a linker reagent, to form drug-linker intermediate D-L, via a covalent bond, followed by reaction with the nucleophilic group or an electrophilic group of an antibody. Conjugation methods (1) and (2) may be employed with a variety of antibodies, drug moieties, and linkers to prepare the antibody-drug conjugates described here.

Several specific examples of methods of preparing ADCs are known in the art and are described in U.S. Pat. No. 8,624,003 (pot method), U.S. Pat. No. 8,163,888 (one-step), and U.S. Pat. No. 5,208,020 (two-step method).

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody-drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p 234-242). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Maytansine may, for example, be converted to May-SSCH3, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. Nos. 6,441,163; 5,208,020; 5,416,064; WO 01/024763). The disulfide linker SPP is constructed with linker reagent N-succinimidyl 4-(2-pyridylthio) pentanoate. ADC of the invention include SMCC linkers and the DM1 maytansinoid drug moiety.

In one embodiment of Ab-(SMCC-DM1)p the average p is 1, 2, 3, or 4. (WO 2005/037992). Another embodiment of an ADC is Ab-(SIAB-DM1)p.

The drug has, or is modified to include, a group reactive with a conjugation point on the antibody. For example, a drug can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols. In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 8; about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3. For examples of chemistries that can be used for conjugation, see, e.g., Current Protocols in Protein Science (John Wiley & Sons, Inc.), Chapter 15 (Chemical Modifications of Proteins) (the disclosure of which is incorporated by reference herein in its entirety.)

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

Testing of the Monovalent Antigen-Binding Constructs

The monovalent antigen-binding constructs according to the invention can exhibit enhanced effector function compared to the corresponding monospecific bivalent antigen-binding construct. The effector functions of the monovalent antigen-binding constructs can be tested as follows. In vitro and/or in vivo cytotoxicity assays can be conducted to assess ADCP, CDC and/or ADCC activities. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. Nos. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to determine if the monovalent antigen-binding constructs are capable of binding C1q and hence activating CDC. To assess complement activation, a CDC assay, e.g. as described in Gazzano-Santoro et al., J. Immunol. Methods 202:163 (1996), may be performed. FcRn binding such as by SPR and in vivo PK determinations of antibodies can also be performed using methods well known in the art.

The presence and quantity of antigen-binding constructs described herein may be determined using ELISA, a well known immunoassay known in the art. In one ELISA protocol that would be useful for detecting/quantifying heteromultimers described herein, comprises the steps of coating an ELISA plate with an anti-human serum albumin antibody, blocking the plate to prevent non-specific binding, washing the ELISA plate, adding a solution containing the protein described herein (at one or more different concentrations), adding a secondary anti-antigen-binding construct polypeptide specific antibody coupled to a detectable label (as described herein or otherwise known in the art), and detecting the presence of the secondary antibody.

As indicated herein, the monovalent antigen-binding constructs described herein display superior efficacy and/or bioactivity as compared to the corresponding monospecific bivalent antigen-binding construct. One non-limiting example of the efficacy and/or bioactivity of the monovalent antigen-binding constructs according to the invention are represented by the ability of the monovalent antigen-binding construct to inhibit growth of the target cell. In one embodiment, the superior efficacy and/or bioactivity of the monovalent antigen-binding constructs is mainly a result of increased effector function of the monovalent antigen-binding construct compared to the monospecific bivalent antigen-binding construct. Examples of this type of monovalent antigen-binding construct are represented by the monovalent lytic antibodies (MV-L).

Increased effector functions that can be tested include at least one of ADCC, ADCP, or CDC.

ADCC

In one embodiment, the monovalent antigen-binding construct exhibits a higher degree of cell killing by ADCC than does the corresponding monospecific bivalent antigen-binding construct. In accordance with this embodiment, the monovalent antigen-binding construct exhibits an increase in ADCC activity of between about 1.2- to 1.6-fold over that of the corresponding monospecific bivalent antigen-binding construct. In one embodiment, the monovalent antigen-binding construct exhibits about a 1.3-fold increase in cell killing by ADCC than does the corresponding monospecific bivalent antigen-binding construct. In one embodiment, the monovalent antigen-binding construct exhibits about a 1.4-fold increase in cell killing by ADCC than does the corresponding monospecific bivalent antigen-binding construct. In one embodiment, the monovalent antigen-binding construct exhibits about a 1.5-fold increase in cell killing by ADCC than does the corresponding monospecific bivalent antigen-binding construct.

In one embodiment, the monovalent antigen-binding construct comprises an antigen-binding polypeptide construct that binds to EGFR and/or HER2 and exhibits an increase in ADCC activity of between about 1.2- to 1.6-fold over that of the corresponding monospecific bivalent antigen-binding construct. In one embodiment, the monovalent antigen-binding construct comprises an antigen-binding polypeptide construct that binds to EGFR and/or HER2 and exhibits about a 1.3-fold increase in cell killing by ADCC than does the corresponding monospecific bivalent antigen-binding construct. In one embodiment, the monovalent antigen-binding construct comprises an antigen-binding polypeptide construct that binds to EGFR and/or HER2 and exhibits about a 1.5-fold increase in cell killing by ADCC than does the corresponding monospecific bivalent antigen-binding construct.

In one embodiment, the monovalent antigen-binding construct comprises an afucosylated antigen-binding polypeptide construct that binds to EGFR and/or HER2 and exhibits an increase in ADCC activity of relative to that of the corresponding non-afucosylated antigen binding construct. In some aspects, the increase in ADCC is between about 1 to 3-fold or greater, e.g., 1, 2, or 3-fold.

ADCP

In one embodiment, the monovalent antigen-binding construct exhibits a higher degree of cell killing by ADCP than does the corresponding monospecific bivalent antigen-binding construct.

CDC

In one embodiment, the monovalent antigen-binding construct exhibits a higher degree of cell killing by CDC than does the corresponding monospecific bivalent antigen-binding construct. In one embodiment, the monovalent antigen-binding construct comprises an antigen-binding polypeptide construct that binds to EGFR and/or HER2 and exhibits about a 1.5-fold increase in cell killing by CDC than does the corresponding monospecific bivalent antigen-binding construct.

In some embodiments is an isolated monovalent antigen-binding construct described herein, wherein said construct possesses at least about 125% of at least one of the ADCC, ADCP and CDC of a corresponding bivalent antigen-binding construct with two antigen binding polypeptide constructs. In some embodiments is an isolated monovalent antigen-binding construct described herein, wherein said construct possesses at least about 150% of at least one of the ADCC, ADCP and CDC of a corresponding bivalent antigen-binding construct with two antigen binding polypeptide constructs. In some embodiments is an isolated monovalent antigen-binding construct described herein, wherein said construct possesses at least about 300% of at least one of the ADCC, ADCP and CDC of a corresponding bivalent antigen-binding construct with two antigen binding polypeptide constructs.

Increased Binding Capacity to FcγRs

In some embodiments, the monovalent antigen-binding constructs exhibit a higher binding capacity (Rmax) to one or more FcγRs. In one embodiment where the monovalent antigen-binding construct comprises an antigen-binding polypeptide construct that binds to HER2, the monovalent antigen-binding construct exhibits an increase in Rmax to one or more FcγRs over the corresponding monospecific bivalent antigen-binding construct of between about 1.3- to 2-fold. In one embodiment where the monovalent antigen-binding construct comprises an antigen-binding polypeptide construct that binds to EGFR and/or HER2, the monovalent antigen-binding construct exhibits an increase in Rmax to a CD16 FcγR of between about 1.3- to 1.8-fold over the corresponding monospecific bivalent antigen-binding construct. In one embodiment where the monovalent antigen-binding construct comprises an antigen-binding polypeptide construct that binds to EGFR and/or HER2, the monovalent antigen-binding construct exhibits an increase in Rmax to a CD32 FcγR of between about 1.3- to 1.8-fold over the corresponding monospecific bivalent antigen-binding construct. In one embodiment where the monovalent antigen-binding construct comprises an antigen-binding polypeptide construct that binds to EGFR and/or HER2, the monovalent antigen-binding construct exhibits an increase in Rmax to a CD64 FcγR of between about 1.3- to 1.8-fold over the corresponding monospecific bivalent antigen-binding construct.

Increased Affinity for FcγRs

In some embodiments, the monovalent antigen-binding constructs provided herein have an unexpectedly increased affinity for FcγR as compared to corresponding bivalent antigen-binding constructs. The increased Fc concentration resulting from the decoration is consistent with increased ADCC, ADCP, CDC activity.

In some embodiments, the monovalent antigen-binding constructs exhibit an increased affinity for one or more FcγRs. In one embodiment, where the monovalent antigen-binding construct comprises an antigen-binding polypeptide construct that binds to HER2, the monovalent antigen-binding constructs exhibit an increased affinity for at least one FcγR. In accordance with this embodiment, the monovalent antigen-binding construct exhibits an increased affinity for CD32.

In another embodiment, is a monovalent antigen-binding construct described herein that exhibits increased internalization compared to a corresponding monospecific bivalent antigen-binding construct, thereby resulting in superior efficacy and/or bioactivity.

Pharmacokinetic Parameters

In certain embodiments, a monovalent antigen-binding construct provided herein exhibits pharmacokinetic (PK) properties comparable with commercially available therapeutic antibodies. In one embodiment, the monovalent antigen-binding constructs described herein exhibit PK properties similar to known therapeutic antibodies, with respect to serum concentration, t½, beta half-life, and/or CL. In one embodiment, the monovalent antigen-binding constructs display in vivo stability comparable ro or greater than said monospecific bivalent antigen-binding construct. Such in vivo stability parameters include serum concentration, t½, beta half-life, and/or $C_L$.

In one embodiment, the monovalent antigen-binding constructs provided herein show a higher volume of distribution (Vss) compared to the corresponding monospecific bivalent antigen-binding constructs. Volume of distribution of an antibody relates to volume of plasma or blood (Vp), the volume of tissue (VT), and the tissue-to-plasma partitioning (kP). Under linear conditions, IgG antibodies are primarily distributed into the plasma compartment and the extravascular fluid following intravascular administration in animals or humans. In some embodiments, active transport processes such as uptake by neonatal Fc receptor (FcRn) also impact antibody biodistribution among other binding proteins.

In another embodiment, the monovalent antigen-binding constructs according to the invention show a higher volume of distribution (Vss) and bind FcRn with similar affinity compared to the corresponding monospecific bivalent antigen-binding constructs.

Competition Assays

Competition between antigen binding constructs can be determined by an assay in which an antigen binding construct under test inhibits specific binding of a reference antigen binding construct to a common antigen (see, e.g., Junghans et al., Cancer Res. 50:1495, 1990). A test antigen binding construct competes with a reference antigen binding construct if an excess of a test antigen binding construct (e.g., at least 2×, 5×, 10×, 20×, or 100×) inhibits binding of the reference antigen binding construct by, e.g., at least 50%, 60%, 70%, 75%, 80%, 85%, 90%, 95%, or 99% as measured in a competitive binding assay. Antigen binding constructs identified by competition assay (competing antigen binding construct) include antigen binding constructs binding to the same epitope as the reference antigen binding construct and antigen binding constructs binding to an adjacent epitope sufficiently proximal to the epitope bound by the reference antigen binding construct for steric hindrance to occur. For example, a second, competing isolated monovalent antigen-binding construct can be identified that competes for binding to EGFR with a first isolated monovalent antigen-binding construct described herein. In certain instances, the second construct can inhibit binding of the first construct by, e.g., at least 50%, 60%, 70%, 75%, 80%, 85%, 90%, 95%, or 99% as measured in a competitive binding assay. In certain instances, the second construct can displace the first construct by greater than 50%, 60%, 70%, 75%, 80%, 85%, 90%, 95%, or 99%.

Kits

Provided herein is a kit for detecting the presence of a biomarker of interest in an individual, said kit comprising (a) an isolated monovalent antigen-binding construct described herein; and (b) instructions for use. In certain embodiments are kits for the detection of at least one of EGFR and/or HER2 and a soluble ECD thereof, said kit comprising (a) an isolated monovalent EGFR and/or HER2 binding antigen-binding construct described herein; and (b) instructions for use. In some embodiments is a kit for determining concentration of at least one of EGFR and/or HER2 and a soluble ECD thereof, said kit comprising (a) an isolated monovalent EGFR and/or HER2 binding antigen-binding construct described herein; and (b) instructions for use.

Production of Antigen-Binding Constructs

Antigen-binding constructs may be produced using recombinant methods and compositions, e.g., as described in U.S. Pat. No. 4,816,567. In one embodiment, isolated nucleic acid encoding an antigen-binding construct described herein is provided. Such nucleic acid may encode an amino acid sequence comprising the VL and/or an amino acid sequence comprising the VH of the antigen-binding construct (e.g., the light and/or heavy chains of the antigen-binding construct). In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antigen-binding construct and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antigen-binding construct is provided, wherein the method comprises culturing a host cell comprising nucleic acid encoding the antigen-binding construct, as provided above, under conditions suitable for expression of the antigen-binding construct, and optionally recovering the antigen-binding construct from the host cell (or host cell culture medium).

For recombinant production of the antigen-binding construct, nucleic acid encoding an antigen-binding construct, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antigen-binding construct).

Suitable host cells for cloning or expression of antigen-binding construct-encoding vectors include prokaryotic or eukaryotic cells described herein. For example, antigen-binding construct may be produced in bacteria, in particular when glycosylation and Fc effector function are not needed. For expression of antigen-binding construct fragments and polypeptides in bacteria, see, e.g., U.S. Pat. Nos. 5,648,237, 5,789,199, and 5,840,523. (See also Charlton, *Methods in Molecular Biology, Vol.* 248 (B.K.C. Lo, ed., Humana Press, Totowa, N.J., 2003), pp. 245-254, describing expression of antibody fragments in *E. coli*.) After expression, the antigen-binding construct may be isolated from the bacterial cell paste in a soluble fraction and can be further purified.

In addition to prokaryotes, eukaryotic microbes such as filamentous fungi or yeast are suitable cloning or expression hosts for antigen-binding construct-encoding vectors, including fungi and yeast strains whose glycosylation pathways have been "humanized," resulting in the production of an antigen-binding construct with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antigen-binding constructs are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antigen-binding constructs in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including $DHFR^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antigen-binding construct production, see, e.g., Yazaki and Wu, *Methods in Molecular Biology*, Vol. 248 (B.K.C. Lo, ed., Humana Press, Totowa, N.J.), pp. 255-268 (2003).

In one embodiment, the antigen-binding constructs described herein are produced in stable mammalian cells, by a method comprising: transfecting at least one stable mammalian cell with: nucleic acid encoding the antigen-binding construct, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antigen-binding construct in the expressed product.

In some embodiments is the method of producing a monovalent antigen-binding construct in stable mammalian cells as described herein wherein the expression product of the at least one stable mammalian cell comprises a larger percentage of the desired glycosylated monovalent antibody as compared to the monomeric heavy or light chain polypeptides, or other antibodies.

In some embodiments is the method of producing a glycosylated monovalent antigen-binding construct in stable mammalian cells described herein, said method comprising identifying and purifying the desired glycosylated monovalent antibody. In some embodiments, the said identification is by one or both of liquid chromatography and mass spectrometry.

If required, the antigen-binding constructs can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antigen-binding constructs. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the use of the antigen-binding constructs. In some instances no purification is necessary.

In certain embodiments the antigen-binding constructs are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antigen-binding constructs described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, N α-methyl amino acids, and amino acid analogs in general. Furthermore, the amino acid can be D (dextrorotary) or L (levorotary).

Also provided are antigen-binding constructs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed herein include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antigen-binding constructs can be modified with a detectable label, such as an enzymatic, fluorescent, isotopic, or affinity label to allow for detection and isolation of the protein.

Examples of suitable enzymes include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, antigen-binding constructs or fragments or variants thereof are attached to macrocyclic chelators that associate with radiometal ions.

As mentioned, the antigen-binding constructs described herein can be modified by either natural processes, such as post-translational processing, or by chemical modification techniques which are well known in the art. It will be appreciated that the same type of modification may be present in the same or varying degrees at several sites in a given polypeptide. Polypeptides of the invention may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

In certain embodiments, antigen-binding constructs may also be attached to solid supports, which are particularly useful for immunoassays or purification of polypeptides that are bound by, that bind to, or associate with albumin fusion proteins of the invention. Such solid supports include, but are not limited to, glass, cellulose, polyacrylamide, nylon, polystyrene, polyvinyl chloride or polypropylene.

Also provided herein are chemically modified derivatives of the antigen-binding constructs which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The proteins may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a Therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 105,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa. Provided in certain embodiments is a method of producing a glycosylated monovalent antigen-binding construct in stable mammalian cells, comprising: transfecting at least one stable mammalian cell with: a first DNA sequence encoding a first heavy chain polypeptide comprising a heavy chain variable domain and a first Fc domain polypeptide; a second DNA sequence encoding a second heavy chain polypeptide comprising a second Fc domain polypeptide, wherein said second heavy chain polypeptide is devoid of a variable domain; and a third DNA sequence encoding a light chain polypeptide comprising a light chain variable domain, such that the said first DNA sequence, said second DNA sequence and said third DNA sequences are transfected in said mammalian cell in a pre-determined ratio; translating the said first DNA sequence, said second DNA sequence, and said third DNA sequence in the at least one mammalian cell such that said heavy and light chain polypeptides are expressed as the desired glycosylated monovalent asymmetric antibody in said at least one stable mammalian cell. In some embodiments is the method of producing a glycosylated monovalent antigen-binding construct in stable mammalian cells described herein, comprising transfecting at least two different cells with different pre-determined ratios of said first DNA sequence, said second DNA sequence and said third DNA sequence such that each of the two cells expresses the heavy chain polypeptides and the light chain polypeptide in a different ratio. In some embodiments is the method of producing a glycosylated monovalent antigen-binding construct in stable mammalian cells described herein, comprising transfecting the at least one mammalian cell with a multi-cistrionic vector comprising said first, second and third DNA sequence. In some embodiments, the at least one mammalian cell is selected from the group consisting of a VERO, HeLa, HEK, HEK293, NS0, Chinese Hamster Ovary (CHO), W138, BHK, COS-7, Caco-2 and MDCK cell, and subclasses and variants thereof.

In some embodiments is the method of producing a glycosylated monovalent antigen-binding construct in stable mammalian cells described herein wherein the predetermined ratio of the first DNA sequence:second DNA sequence:third DNA sequence is about 1:1:1. In some embodiments, the said predetermined ratio of the first DNA sequence:second DNA sequence:third DNA sequence is such that the amount of translated first heavy chain polypeptide is about equal to the amount of the second heavy chain polypeptide, and the amount of the light chain polypeptide.

In some embodiments is the method of producing a glycosylated monovalent antigen-binding construct in stable mammalian cells described herein wherein the expression product of the at least one stable mammalian cell comprises a larger percentage of the desired glycosylated monovalent antibody as compared to the monomeric heavy or light chain polypeptides, or other antibodies.

In some embodiments is the method of producing a glycosylated monovalent antigen-binding construct in stable mammalian cells described herein, said method comprising identifying and purifying the desired glycosylated monovalent antibody. In some embodiments, the said identification is by one or both of liquid chromatography and mass spectrometry.

Provided herein is a method of producing antigen-binding constructs with improved ADCC comprising: transfecting at least one stable mammalian cell with: a first DNA sequence encoding a first heavy chain polypeptide comprising a heavy chain variable domain and a first Fc domain polypeptide; a second DNA sequence encoding a second heavy chain polypeptide comprising a second Fc domain polypeptide, wherein said second heavy chain polypeptide is devoid of a variable domain; and a third DNA sequence encoding a light chain polypeptide comprising a light chain variable domain, such that the said first DNA sequence, said second DNA sequence and said third DNA sequences are transfected in said mammalian cell in a pre-determined ratio; translating the said first DNA sequence, said second DNA sequence, and said third DNA sequence in the at least one mammalian cell such that said heavy and light chain polypeptides are expressed as a glycosylated monovalent antibody in said at least one stable mammalian cell, wherein said glycosylated monovalent asymmetric antibody has a higher ADCC as compared to a corresponding wild-type antibody.

Provided herein is a method of producing a glycosylated monovalent antigen-binding construct in stable mammalian cells, comprising: transfecting at least one stable mammalian cell with: a first DNA sequence encoding a first heavy chain polypeptide comprising a heavy chain variable domain and a first Fc domain polypeptide; a second DNA sequence encoding a second heavy chain polypeptide comprising a second Fc domain polypeptide, wherein said second heavy chain polypeptide is devoid of a variable domain; and a third DNA sequence encoding a light chain polypeptide comprising a light chain variable domain, such that the said first DNA sequence, said second DNA sequence and said third DNA sequences are transfected in said mammalian cell in a pre-determined ratio; translating the said first DNA sequence, said second DNA sequence, and said third DNA sequence in the at least one mammalian cell such that said heavy and light chain polypeptides are expressed as the desired glycosylated monovalent asymmetric antibody in said at least one stable mammalian cell.

Also provided are transgenic organisms modified to contain nucleic acid molecules described herein to encode and express monovalent antigen-binding constructs described herein.

Pharmaceutical Compositions

The antigen binding constructs described herein can be formulated and administered by any method well known to one of skill in the art and depending on the application. In some embodiments the antigen-binding construct is formulated in a pharmaceutical composition of the antigen-binding construct and a pharmaceutically acceptable carrier.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In some aspects, the carrier is a man-made carrier not found in nature. Water can be used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the antigen-binding constructs is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

In certain embodiments is a pharmaceutical composition comprising the monovalent antigen-binding construct described herein and an adjuvant. In certain embodiments is the pharmaceutical composition described herein, further comprising a drug molecule conjugated to the monovalent antigen-binding construct. In certain embodiments, the drug molecule is for the treatment of an autoimmune disorder. In some embodiments, the drug molecule is for the treatment of a cancer. In some embodiments, the drug molecule is a chemotherapeutic agent.

Biological and Therapeutic Uses

In certain embodiments, constructs described herein, are used in assays to test for one or more biological activities. If a construct exhibits an activity in a particular assay, it is likely that the antigen binding construct comprised by the antigen-binding construct is implicated in the diseases associated with the biological activity. Thus, the construct is of use in a treatment of the associated disease.

In certain embodiments is use of a monovalent antigen-binding construct described herein for the manufacture of a medicament for inhibiting multimerization of an antigen molecule. In certain embodiments is use of a monovalent antigen-binding construct for inhibiting binding of an antigen to its cognate binding partner.

In certain embodiments, provided is a method of treating a disease or disorder comprising administering to a patient in which such treatment, prevention or amelioration is desired, an antigen-binding construct described herein, in an amount effective to treat, prevent or ameliorate the disease or disorder.

In certain embodiments, antigen-binding constructs described herein are used in the diagnosis, prognosis, prevention and/or treatment of diseases and/or disorders of the endocrine system. In some embodiments, antigen-binding constructs described herein are used in the diagnosis, prognosis, prevention and/or treatment of diseases and/or disorders of the nervous system.

In certain embodiments, antigen-binding constructs described herein are used in the diagnosis, prognosis, prevention and/or treatment of diseases and/or disorders of the immune system. In certain embodiments, antigen-binding constructs described herein are used in the diagnosis, prognosis, prevention and/or treatment of diseases and/or disorders of the respiratory system.

In certain embodiments, antigen-binding constructs described herein are used in the diagnosis, prognosis, prevention and/or treatment of diseases and/or disorders of the cardiovascular system. In some embodiments, antigen-binding constructs described herein are used in the diagnosis, prognosis, prevention and/or treatment of diseases and/or disorders of the reproductive system.

In certain embodiments, antigen-binding constructs described herein are used in the diagnosis, prognosis, prevention and/or treatment of diseases and/or disorders of the digestive system. In certain embodiments, antigen-binding constructs described herein are used in the diagnosis, prognosis, prevention and/or treatment of diseases or disorders relating to the blood.

In some embodiments, antigen-binding constructs described herein and/or polynucleotides encoding the antigen-binding constructs described herein, are used in the diagnosis, detection and/or treatment of diseases and/or disorders associated with activities that include, but are not limited to, prohormone activation, neurotransmitter activity, cellular signaling, cellular proliferation, cellular differentiation, and cell migration.

In an aspect, antigen-binding constructs described herein are directed to antibody-based therapies which involve administering antigen-binding constructs, to a patient for treating one or more of the disclosed diseases, disorders, or conditions. Therapeutic compounds described herein include, but are not limited to antigen-binding constructs described herein, nucleic acids encoding antigen-binding constructs described herein.

In a specific embodiment, are antibody-based therapies which involve administering antigen-binding constructs described herein comprising at least a fragment or variant of an antibody to a patient for treating one or more diseases, disorders, or conditions, including but not limited to: neural disorders, immune system disorders, muscular disorders, reproductive disorders, gastrointestinal disorders, pulmonary disorders, cardiovascular disorders, renal disorders, proliferative disorders, and/or cancerous diseases and conditions, and/or as described elsewhere herein.

The antigen-binding constructs described herein, comprising at least a fragment or variant of an antibody may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in an embodiment, human antibodies, fragments derivatives, analogs, or nucleic acids, are administered to a human patient for therapy or prophylaxis.

Provided are methods of treatment, inhibition and prophylaxis by administration to a subject of an effective amount of an antigen-binding construct or pharmaceutical composition described herein. In an embodiment, the antigen-binding construct is substantially purified (e.g., substantially free from substances that limit its effect or produce undesired side-effects). In certain embodiments, the subject is an animal, including but not limited to animals such as cows, pigs, horses, chickens, cats, dogs, etc., and in certain embodiments, a mammal, and most preferably human.

Various delivery systems are known and can be used to administer an antigen-binding construct formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the antigen-binding construct compositions described herein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it is desirable to administer the antigen-binding constructs, or compositions described herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the antigen-binding constructs or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen-binding constructs or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)).

In certain embodiments a one arm monovalent antigen-binding construct described herein is administered as a combination with other one arm monovalent or multivalent antibodies with non-overlapping binding target epitopes.

In some embodiments is a method of treating an immune system disorder comprising providing to a patient in need thereof an effective amount of a pharmaceutical composition described herein. In certain embodiments is a method of inhibiting growth of a tumor, comprising contacting the tumor with a composition comprising an effective amount of a monovalent antigen-binding construct described herein. Provided is a method of shrinking a tumor, comprising contacting the tumor with a composition comprising an effective amount of a monovalent antigen-binding construct described herein. In some embodiments is a method of inhibiting multimerization of an antigen molecule, comprising contacting the antigen with a composition comprising an effective amount of a monovalent antigen-binding construct described herein. Provided herein is a method of inhibiting binding of an antigen to its cognate binding partner comprising contacting the antigen with a composition comprising an amount of a monovalent antigen-binding construct sufficient to bind to the antigen.

Provided herein is a method of increasing antibody concentration in at least one target cell comprising providing to the target cell a monovalent antigen-binding construct comprising: an antigen-binding polypeptide construct which monovalently binds an antigen; a dimeric Fc domain; wherein said monovalent antigen-binding construct displays an increase in binding density and Bmax (maximum binding) to a target cell displaying said antigen as compared to a corresponding bivalent antigen-binding construct with two antigen binding regions, and wherein said monovalent antigen-binding construct shows better therapeutic efficacy compared to a corresponding bivalent antigen-binding construct, and wherein said efficacy is not caused by crosslinking of the antigen, antigen dimerization, prevention of antigen modulation, or prevention of antigen activation.

Provided herein are isolated monovalent antigen-binding constructs comprising an antigen-binding polypeptide construct which monovalently binds an antigen; and a dimeric Fc polypeptide construct comprising a CH3 domain; wherein said monovalent antigen-binding construct displays an increase in binding density and Bmax (maximum binding) to a target cell displaying said antigen as compared to a corresponding bivalent antigen-binding construct with two antigen binding regions, and wherein said monovalent antigen-binding construct shows better therapeutic efficacy compared to a corresponding bivalent antigen-binding construct, and wherein said efficacy is not caused by crosslinking of the antigen, antigen dimerization, prevention of antigen modulation, or prevention of antigen activation.

Provided herein are isolated monovalent antigen-binding construct that binds EGFR and/or HER2 comprising: an antigen binding polypeptide construct which monovalently binds EGFR and/or HER2; and a dimeric Fc polypeptide construct comprising a CH3 domain; wherein said antigen-binding construct is internalized by a target cell, wherein said construct displays an increase in binding density and Bmax (maximum binding) to EGFR and/or HER2 displayed on the target cell as compared to a corresponding bivalent antigen-binding construct which bivalently binds EGFR and/or HER2, and wherein said construct displays at least one of higher ADCC, higher ADCP and higher CDC as compared to said corresponding bivalent EGFR and/or HER2 binding antigen-binding constructs.

Also provided is a method of preventing antigen extracellular domain proteolytic cleavage by binding of the antigen to a monovalent antigen-binding construct provided herein.

Treatment of Cancers

Provided herein is the use of a monovalent antigen-binding construct described herein for the manufacture of a medicament for treating cancer. Also provided is use of a monovalent antigen-binding construct described herein for the manufacture of a medicament for an immune system disorder. In certain embodiments is use of a monovalent antigen-binding construct described herein for the manufacture of a medicament for inhibiting growth of a tumor. In certain embodiments is use of a monovalent antigen-binding construct described herein for the manufacture of a medicament for shrinking a tumor.

Provided herein is the use of a monovalent EGFR and/or HER2 binding antigen-binding construct described herein for the manufacture of a medicament for treating cancer. In certain embodiments, the cancer is a low EGFR and/or HER2 expressing cancer. In certain embodiments, the cancer is resistant to treatment with a bivalent EGFR and/or HER2 antibody. Provided herein is the use of a monovalent EGFR and/or HER2 binding antigen-binding construct described herein for the manufacture of a medicament for treating cancers resistant to treatment with Trastazaumab.

In one embodiment, the monovalent antigen-binding constructs described herein are used in the treatment of cancer. In one embodiment, monovalent antigen-binding constructs comprising an EGFR and/or HER2 binding polypeptide construct described herein are useful in the treatment of a cancer or any proliferative disease associated with EGFR and/or HER dysfunction, including HER1 dysfunction, HER2 dysfunction, HER 3 dysfunction, and/or HER4 dysfunction. In certain embodiments the cancer is at least one of breast cancer, triple negative breast cancer, KRAS mutation positive cancer, gastric cancer, brain cancer, lung cancer, ovarian cancer, epidermoid-derived cancer, bladder cancer, head and neck cancer, pancreatic cancer or is at least one type of carcinoma.

In one embodiment, EGFR and/or HER2 binding monovalent antigen-binding constructs described herein are used in the treatment of a breast cancer cell. In certain embodiments, the EGFR and/or HER2 binding monovalent antigen-binding constructs are used in the preparation of a pharmaceutical composition for administration to an individual suffering from cancer. In some embodiments is the treatment of cancer in an individual by providing to said individual an effective amount of at least one EGFR and/or HER2 binding monovalent antigen-binding construct described herein.

In one embodiment, an EGFR and/or HER2 binding monovalent antigen-binding construct described herein is used to treat patients that are partially responsive to current therapies. In one embodiment, EGFR and/or HER2 binding monovalent antigen-binding constructs described herein are used to treat patients that are resistant to current therapies. In another embodiment, EGFR and/or HER2 binding monovalent antigen-binding constructs described herein are used to treat patients that are developing resistance to current therapies.

In one embodiment, EGFR and/or HER2 binding monovalent antigen-binding constructs described herein are useful to treat patients that are unresponsive to current therapies. In certain embodiments, these patients suffer from a triple negative cancer. In some embodiments, the triple-negative cancer is a breast cancer with low to negligent expression of the genes for estrogen receptor (ER), progesterone receptor (PR) and Her2. In certain other embodiments the EGFR and/or HER2 binding monovalent antigen-binding constructs described herein are provided to patients that are unresponsive to current therapies, optionally in combination with one or more current anti-HER2 therapies. In some embodiments the current anti-HER2 therapies include, but are not limited to, anti-HER2 or anti-HER3 monospecific bivalent antibodies, trastuzumab, pertuzumab, T-DM1, a bi-specific HER2/HER3 scFv, or combinations thereof. In one embodiment, a monovalent antigen-binding construct described herein is used to treat patients that are not responsive to trastuzumab, pertuzumab, T-DM1, anti-HER2, or anti-HER3, alone or in combination.

In one embodiment, an EGFR and/or HER2 binding monovalent antigen-binding construct that comprise an antigen-binding polypeptide construct that binds EGFR and/or HER2 can be used in the treatment of patients with metastatic breast cancer. In one embodiment, an EGFR and/or HER2 binding monovalent antibody is useful in the treatment of patients with locally advanced or advanced metastatic cancer. In one embodiment, an EGFR and/or HER2 binding monovalent antibody is useful in the treatment of patients with refractory cancer. In one embodiment, an EGFR and/or HER2 binding monovalent antibody is provided to a patient for the treatment of metastatic cancer when said patient has progressed on previous anti-HER2 therapy. In one embodiment, an EGFR and/or HER2 binding monovalent antibody described herein can be used in the treatment of patients with triple negative breast cancers. In one embodiment, an EGFR and/or HER2 binding monovalent antibody described herein is used in the treatment of patients with advanced, refractory HER2-amplified, heregulin positive cancers.

In some types of EGFR-expressing cancers, for example non-small cell lung cancer therapy using the bivalent anti-EGFR antibody cetuximab is more efficacious against the cancer if the level of EGFR expression is high (Pirker et al., Lancet 13: 33-42 (2102). Methods are known in the art for determining the level of EGFR expression of a cell and for determining the level of EGFR expression in a tumor, and commercial kits are available for this purpose e.g. the DAKO pharmDX kit (Glostrup, Denmark). Tumors may be scored for membrane staining intensity of individual tumor cells in a sample (on a scale of 1+ to 3+) and also the fraction of tumor cells in the sample staining at each intensity. Membrane staining is graded as follows: 0=no staining; 1+=weak staining visible only at high magnification; 2+=between 1+ and 3+; 3+=dark linear membrane staining visible with low magnification. Pirker et al. reported a study in which the intensity of staining was integrated with the frequency of staining in the tumor sample. An immunochemistry (IHC) score on a scale of 1-300 for each tumor sample was calculated using the formula: 1×(percentage of cells staining 1+)+2×(percentage of cells staining 2+)+3×(percentage of cells staining 3+), giving a maximum score of 300 (for 100% of cells staining 3+). Tumor having IHC scores of 200 or higher were considered to be high-EGFR expressing tumors. This method of scoring was shown to be highly reproducible in a subsequent study (Ruschoff el al. Arch Pathol Lab Med 137: 1255-1261 (2013).

Also disclosed herein is a method of treating a subject having an epidermal growth factor receptor (EGFR)-expressing tumor, comprising: contacting the tumor with an effective amount of an isolated monovalent EGFR-binding construct comprising at least one antigen-binding polypeptide comprising a heavy chain variable domain coupled, with or without a linker, to a heterodimeric Fc, wherein the antigen-binding polypeptide specifically binds to EGFR. In some aspects, the construct binds to EGFR with a greater $B_{max}$ as compared to the corresponding isolated monospecific bivalent antigen-binding construct that specifically binds EGFR.

In certain aspects, a tumor to be treated by a method disclosed herein expresses a low level of EGFR. In certain aspects, the tumor expresses a low level of EGFR relative to a control tumor. In some aspects, the tumor expresses a first level of cell surface EGFR that is equal to or less than a second level of cell surface EGFR of one or more than one of the following cell lines: A431, A549, BT474, CACO2, HACAT, HCT116, JIMT1, MDA-MB-231, SKOV3, MCF7, or SKBR3. See Table AA below for further details. In certain aspects, the tumor expresses a median of about $3.5\times10^6$ or less EGFRs per cell. In certain aspects, the tumor expresses a median of about $2.8\times10^6$ or less EGFRs per cell. In certain aspects, the tumor expresses a median of about $1.2\times10^6$ or less EGFRs per cell. In certain aspects, the tumor expresses a median of about $2.4\times10^5$ or less EGFRs per cell. In certain aspects, the tumor expresses a median of about $2.6\times10^5$ or less EGFRs per cell. In certain aspects, the tumor expresses a median of about $4.2\times10^4$ or less EGFRs per cell. In certain aspects, a sample of the tumor expresses a median level of EGFR of less than 3+ when assessed using immunohistochemistry staining. In certain aspects, a sample of the tumor expresses a median level of EGFR of less than 2+ when assessed using immunohistochemistry staining. In certain aspects, a sample of the tumor expresses a median level of EGFR of less than 1+ when assessed using immunohistochemistry staining. In certain aspects the tumor expresses EGFRs at a level of 300 or less when assessed by the method described in Pirker et al. In certain aspects the tumor expresses EGFRs at a level of 200 or less when assessed by the method described in Pirker et al. In certain aspects the tumor expresses EGFRs at a level of 100 or less when assessed by the method described in Pirker et al.

In certain aspects, a subject treated by a method disclosed herein and administered a fixed dose of an isolated monovalent EGFR-binding construct disclosed herein experiences less skin toxicity from the treatment compared to a subject treated with a fixed dose of the corresponding isolated monospecific bivalent antigen-binding construct that specifically binds EGFR.

In certain aspects, a subject is treated by a method disclosed herein and administered a fixed dose of an isolated monovalent EGFR-binding construct disclosed herein, wherein following treatment, growth of the subject's keratinocytes is reduced less compared to a subject treated with a fixed dose of the corresponding isolated monospecific bivalent antigen-binding construct that specifically binds EGFR.

In certain aspects the EGFR-expressing tumor being treated with an isolated monovalent EGFR-binding construct is an epidermal cell-derived cancer, a lung cancer, a breast cancer, a triple negative breast cancer, a ductal breast ductal cancer, a pancreatic cancer, a head and neck cancer, a gastric cancer, an ovarian cancer, a HER2+ cancer, or a colorectal cancer. In certain aspects, the cancer is KRAS mutation-positive. In certain aspects the isolated monovalent EGFR-binding construct is afucosylated. In some aspects, the result of treatment is shrinking the tumor, inhibiting the growth of the tumor, increasing time to progression of the tumor, prolonging disease-free survival of the subject, or increasing the survival of the subject.

Also provided herein are EGFR and/or HER2 binding monovalent antigen-binding constructs to be administered in combination with other known therapies for the treatment of cancer. In accordance with this embodiment, the monovalent antigen-binding constructs can be administered in combination with other monovalent antigen-binding constructs or multivalent antibodies with non-overlapping binding target epitopes to significantly increase the $B_{max}$ and antibody dependent cytotoxic activity above FSAs. For example, a monovalent EGFR-binding construct according to the invention can be administered 1) in combination with one or more monovalent HER2-binding constructs such as OA-Tras or OA-Pert or 2) in combination with one or more a bivalent HER2-binding constructs such as pertuzumab or trastuzumab, or 3) in multiple combinations of non-competing antibodies directed at the same and different surface antigens on the same target cell. In certain embodiments, the monovalent antigen-binding constructs described herein are administered in combination with a therapy selected from Herceptin™, TDM1, afucosylated antibodies, antibodies conjugated to toxins such as DM1, or Perjeta™.

Provided herein is a method of treating cancer comprising providing to a patient in need thereof an effective amount of a pharmaceutical composition described herein. In one embodiment, the disease to be treated is cancer. In another embodiment, the cancer to be treated is a breast cancer, e.g., wherein the cells of the breast cancer express HER2 protein in high, medium, or low density. The following Table A6 describes the expression level of HER2 on several representative breast cancer cell lines (Subik et al. (2010) Breast Cancer: Basic Clinical Research: 4; 35-41; Prang et a. (2005) British Journal of Cancer Research: 92; 342-349). As shown in the table, MCF-7 and MDA-MB-231 cells are considered to be low HER2 expressing cells; SKOV3 cells are considered to be medium HER2 expressing cells, and SKBR3 cells are considered to be high HER2 expressing cells.

TABLE A6

| Cell Line | HER2 level | HER2 Bmax ($\times10^3$) |
|---|---|---|
| MCF-7 | 0-1+ | 25 |
| MDA-MB-231 | 0-1+ | 14 (triple negative) |
| SKOV3 | 2+ | 300 |
| SKBr3 | 3+ | 976 |

Gene Therapy:

In a specific embodiment, nucleic acids comprising sequences encoding antigen-binding constructs described herein are administered to treat, inhibit or prevent a disease or disorder associated with aberrant expression and/or activity of a protein, by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available in the art can be used.

In a specific embodiment comprising a nucleic acid encoding antigen-binding constructs described herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

Various publications are cited herein, the disclosures of which are incorporated by reference in their entireties.

REFERENCES

Bowles J A, Wang S Y, Link B K, Allan B, Beuerlein G, Campbell M A, Marquis D, Ondek B, Wooldridge J E, Smith B J, Breitmeyer J B, Weiner G J. Anti-CD20 monoclonal antibody with enhanced affinity for CD16 activates NK cells at lower concentrations and more effectively than rituximab. Blood. 2006 Oct. 15; 108(8): 2648-54. Epub 2006 Jul. 6.

Desjarlais J R, Lazar G A. Modulation of antibody effector function. Exp Cell Res. 2011 May 15; 317(9):1278-85.

Ferrara C, Grau S, Jäger C, Sondermann P, Brünker P, Waldhauer I, Hennig M, Ruf A, Rufer A C, Stihle M, Umaña P, Benz J. Unique carbohydrate-carbohydrate interactions are required for high affinity binding between FcgammaRIII and antibodies lacking core fucose. Proc Natl Acad Sci USA. 2011 Aug. 2; 108(31):12669-74.

Heider K H, Kiefer K, Zenz T, Volden M, Stilgenbauer S, Ostermann E, Baum A, Lamche H, Küpcü Z, Jacobi A, Müller S, Hirt U, Adolf G R, Borges E. A novel Fc-engineered monoclonal antibody to CD37 with enhanced ADCC and high proapoptotic activity for treatment of B-cell malignancies. Blood. 2011 Oct. 13; 118(15):4159-68. Epub 2011 Jul. 27. Blood. 2011 Oct. 13; 118(15): 4159-68. Epub 2011 Jul. 27.

Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I. Engineered antibody Fc variants with enhanced effector function. Proc Natl Acad Sci USA. 2006 Mar. 14; 103(11):4005-10. Epub 2006 Mar. 6.

Lu Y, Verres J M, Chiang N, Ou Q, Ding J, Adams C, Hong K, Truong B T, Ng D, Shen A, Nakamura G, Gong Q, Presta L G, Beresini M, Kelley B, Lowman H, Wong W L, Meng Y G. Identification of IgG(1) variants with increased affinity to FcγRIIIa and unaltered affinity to FcγRI and FcRn: comparison of soluble receptor-based and cell-based binding assays. J Immunol Methods. 2011 Feb. 28; 365(1-2):132-41. Epub 2010 Dec. 23.

Mizushima T, Yagi H, Takemoto E, Shibata-Koyama M, Isoda Y, Iida S, Masuda K, Satoh M, Kato K. Structural basis for improved efficacy of therapeutic antibodies on defucosylation of their Fc glycans. Genes Cells. 2011 November; 16(11):1071-1080.

Moore G L, Chen H, Karki S, Lazar G A. Engineered Fc variant antibodies with enhanced ability to recruit complement and mediate effector functions. MAbs. 2010 March-April; 2(2):181-9.

Nordstrom J L, Gorlatov S, Zhang W, Yang Y, Huang L, Burke S, Li H, Ciccarone V, Zhang T, Stavenhagen J, Koenig S, Stewart S J, Moore P A, Johnson S, Bonvini E. Anti-tumor activity and toxicokinetics analysis of MGAH22, an anti-HER2 monoclonal antibody with enhanced Fc-gamma receptor binding properties. Breast Cancer Res. 2011 Nov. 30; 13(6):R123. [Epub ahead of print]

Richards J O, Karki S, Lazar G A, Chen H, Dang W, Desjarlais J R. Optimization of antibody binding to FcgammaRIIa enhances macrophage phagocytosis of tumor cells. Mol Cancer Ther. 2008 August; 7(8):2517-27.

Schneider S, Zacharias M. Atomic resolution model of the antibody Fc interaction with the complement C1q component. Mol Immunol. 2012 May; 51(1):66-72.

Shields R L, Namenuk A K, Hong K, Meng Y G, Rae J, Briggs J, Xie D, Lai J, Stadlen A, Li B, Fox J A, Presta L G. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001 Mar. 2; 276(9):6591-604.

Stavenhagen J B, Gorlatov S, Tuaillon N, Rankin C T, Li H, Burke S, Huang L, Vijh S, Johnson S, Bonvini E, Koenig S. Fc optimization of therapeutic antibodies enhances their ability to kill tumor cells in vitro and controls tumor expansion in vivo via low-affinity activating Fcgamma receptors. Cancer Res. 2007 Sep. 15; 67(18):8882-90.

Stewart R, Thom G, Levens M, Güler-Gane G, Holgate R, Rudd P M, Webster C, Jermutus L, Lund J. A variant human IgG1-Fc mediates improved ADCC. Protein Eng Des Sel. 2011 September; 24(9):671-8. Epub 2011 May 18.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992).

Table AA provides a list of the cell lines used in the examples of specific embodiments shown herein.

TABLE AA

Cell lines used in the Examples showing the origin and the level of EGFR and HER2 expression

| Cell line | Type | EGFR | HER2 | Reference |
|---|---|---|---|---|
| A431 | epidermoid carcinoma | $3.5 \times 10^6$ (3+)/ $2.8 \times 10^6$ | low | Kurai 2007/ Spangler 2012/ Anido 2003 |
| A549 | lung alveolar adenocarcinoma | $1.2 \times 10^6$ | low (0) | Spangler 2012/ Nakamura 2005/ Bunn 2001 |

TABLE AA-continued

| Cell lines used in the Examples showing the origin and the level of EGFR and HER2 expression | | | | |
|---|---|---|---|---|
| Cell line | Type | EGFR | HER2 | Reference |
| BT474 | breast ductal carcinoma | (1+) | (3+) | Subik 2010 |
| CACO2 | epithelial colorectal adenocarcinoma | low | mid/low | Xu 2005 |
| HACAT | immortalized keratinocyte (non-cancerous) | mid/low | low | Rao 2012 |
| HCT116 | colon carcinoma | mid/low/2.4 × $10^5$ | mid/low | Xu 2005/ Spangler 2012 |
| JIMT1 | invasive breast ductal carcinoma | mid | mid/(3+) | Dragowska 2011/ Tanner 2004 |
| MDA-MB-231 | breast adenocarcinoma, triple negative breast cancer (TNBC) | mid/(1+) | (0-1+) | Neve 2006/ Subik 2010 |
| SKOV3 | ovarian carcinoma | 2.6 × $10^5$ | 1.4 × $10^6$ | McDonagh 2012 |
| MCF7 | invasive breast ductal carcinoma | (1+) | (0-1+) | Subik 2010 |
| SKBR3 | breast adenocarcinoma | 4.2 × $10^4$ (2+) (1+) | 1.8 × $10^6$/ (3+) | (Subik 2010)/ Xu 2005/ Pedersen 2010 |

*Expression level is based on results from immunohistological stains reported (when available), following the criteria described for HercepTest. References for receptor count per cell were reported in McDonagh et at Mol Cancer Ther. 2012 Mar; 11(3): 582-93, Subik et at Breast Cancer (Auckl). 2010 May 20; 4: 35-41, Kurai et al Clin Cancer Res 2007; 13(5): 1552-61, Gaborit et at J Biol Chem. 2011 Apr 1; 286(13): 11337-45, Spangler et al, PNAS 2010; 107(30): 13252-13257, Anido et al, Clin Cancer Res 2003; 9: 1274-1283, Nakamura et al, Cancer Letters 230 (2005) 33-46, Bunn et al, Clin Cancer Res 2001; 7: 3239-3250, Xu et al, Mol Cancer Ther 2005; 4: 435-442, Rao et al, Oncogene (2012) 31, 2888-2898, Dragowska et al. BMC Cancer 2011, 11: 420, Tanner et al, Mol Cancer Ther 2004; 3: 1585-1592 and Neve et al, Cancer Cell 2006 Dec; 10(6): 515-27. Some minor variations to the receptor count have been observed depending on the method employed for determination.

Example 1—Preparation of Exemplary OA-EGFR Antibodies and Controls

Table 1 provides an identification of the OA-EGFR antibodies and controls that were prepared.

TABLE 1

| List of OA-EGFR antibodies and controls | | |
|---|---|---|
| Molecules | variant # | description |
| hIgG1 | 6908 | polyclonal human IgG1 |
| Herceptin ™ | 6336 | commercial trastuzumab |
| FSA-Tras | 506 | full sized trastuzumab |
| OA-Tras | 1040 | one armed trastuzumab |
| Erbitux ™ | 7180 | commercial cetuximab |
| OA-CTX | 4353 | one armed cetuximab |
| OA-EG2 | 1323 | one armed domain antibody |
| OA-Pert | 4182 | one armed pertuzumab |
| OA-CTX-afuco | 7192 | afucosylated one armed cetuximab (Example 9) |
| OA-CTX-afuco-ADC | 7104 | afucosylated one armed cetuximab conjugated to DM1 (Example 10) |
| FSA-Tras-ADC | 6246 | FSA-Tras (v506) conjugated to DM1 |
| hIgG-ADC | 6249 | Human IGg1 conjugated to DM1 |

hIgG1 (Cat. No. 009-000-003) was purchased from Jackson ImmunoResearch (West Grove, Pa.).

Herceptin™ (trastuzumab) was purchased from Roche. Trastuzumab binds to extracellular domain 4 (ECD4) of HER2.

Erbitux™ (cetuximab) was purchased from Bristol-Meyers Squibb. Cetuximab binds to ECD3 of EGFR.

FSA-Tras (v506) is a wild-type trastuzumab produced in-house in CHO cells as a control. Both Fab HER2 binding domains are the same as trastuzumab and the Fc is a wild type homodimer; the epitope of the antigen binding domain is domain 4 of HER2.

OA-Tras (v1040) is a monovalent anti-HER2 antibody, where the HER2 binding domain is an Fab on chain A, and the Fc region is a heterodimer having the mutations T350V_L351Y_F405A_Y407V in Chain A (EU numbering), and T350V_T366L_K392L_T394W in Chain B (EU numbering); the epitope of the antigen binding domain is domain 4 of HER2.

OA-Pert (v4182) is a monovalent anti-HER2 antibody, where the HER2 binding domain is an Fab on chain A, and the Fc region is a heterodimer having the mutations T350V_L351Y_F405A_Y407V in Chain A, and T350V_T366L_K392L_T394W in Chain B. The epitope of the antigen binding domain is domain 2 of HER2.

OA-CTX (v4353) is a monovalent anti-EGFR antibody with a heterodimeric IgG1 Fc. The Fab, whose protein sequence was derived from Genbank accession numbers 1YY8_B and 1YY8_A (accessed on Nov. 10, 2014), is mounted on heavy chain A, containing T350V_L351Y_F405A_Y407V and heavy chain B corresponds to the Fc fragment with T350V_T366L_K392L_T394W. The epitope recognized by the antigen binding domain is domain 3 of EGFR. The molecule is also expected to be neutralizing, like cetuximab, in that it is capable of preventing both the ligand-dependent and ligand-independent activation of EGFR (Li et al Cancer Cell. 2005 April; 7(4):301-11).

OA-EG2 (v1323) is a one armed antibody of a single domain antibody EG2 (Bell et al Cancer Lett. 2010 Mar. 1; 289(1):81-90) on a heterodimeric IgG1 Fc. The Fab is mounted on heavy chain A, containing T350V_L351Y_F405A_Y407V and heavy chain B corresponds to the Fc fragment with T350V_T366L_K392L_T394W. OA-EG2 binds to an extracellular domain of EGFR and does not compete with cetuximab or EGF for EGFR binding.

OA-CTX-afuco is an afucosylated form of OA-CTX (see Example 9).

OA-CTX-afuco-ADC is an afucosylated form of OA-CTX that has been conjugated to DM1 (see example 10).

TABLE B

| SEQ ID NO | DESCRIPTION | SEQUENCE |
|---|---|---|
| 1 | 4353 VH | QVQLKQSGPGLVQPSQSLSITCTVSGESLTNYGVHWVRQSPGKGLEWLGVIWSGGNTDYNTPFTSRLSINKD NSKSQVFFKMNSLQSNDTAIYYCAPALTYYDYEFAYWGQGTLVTVSA |
| 41 | | CAGGTCCAGCTGAAGCAGAGCGGACCAGGACTGGTGCAGCCTTCACAGAGCCTGTCCATCACTTGCACCGTG TCCGGATTCTCTCTGACAAACTACGGAGTCCACTGGGTGCGACAGAGTCCAGGAAAAGGCCTGGAGTGGCTG GGCGTGATCTGGAGCGGAGGGAACACTGACTATAATACTCCTTTTACCAGTCGGCTGTCAATTAACAAGGAT AACTCTAAGAGTCAGGTGTTCTTTAAGATGAACAGCCTGCAGTCCAATGACACAGCTATCTACTATTGCGCT AGAGCACTGACTTACTATGATTACGAGTTCGCATATTGGGGGCAGGGAACACTGGTCACTGTGTCTGCC |
| 2 | 4353 VH CDR1 | GFSLTNYGVH |
| 42 | | GGATTCTCTCTGACAAACTACGGAGTCCAC |
| 3 | 4353 VH CDR2 | IWSGGNT |
| 43 | | ATCTGGAGCGGAGGGAACACT |
| 4 | 4353 VH CDR3 | ALTTYDYEFAY |
| 44 | | GCACTGACTTACTATGATTACGAGTTCGCATAT |
| 5 | 4353 VL | DILLTQSPVILSVSPGERVSFSCRASQSIGTNIHWYQQRTNGSPRLLIKYASESISGIPSRFSGSGSGTDFT LSINSVESEDIADYYCQQNNNWPTTFGAGTKLELK |
| 45 | | GACATCCTGCTGACTCAGAGCCCAGTGATCCTGTCAGTCAGCCCAGGAGAGCGGGTGTCCTTCTCTTGCAGA GCAAGTCAGTCAATCGGAACAAATATTCACTGGTACCAGCAGAGGACTAACGGCTCCCCTCGCCTGCTGATT AAGTATGCTAGCGAATCCATCTCTGGCATTCCATCTCGGTTCAGTGGCTCAGGGAGCGGAACAGACTTTACT CTGTCCATCAATTCTGTGGAGAGTGAAGACATTGCCGATTACTATTGCCAGCAGAACAATAACTGGCCCACC ACATTCGGCGCTGGGACCAAGCTGGAGCTGAAA |
| 6 | 4353 VL CDR1 | RASQSIGTNIH |
| 46 | | AGAGCAAGTCAGTCAATCGGAACAAATATTCAC |
| 7 | 4353 VL CDR2 | YASESIS |
| 47 | | TATGCTAGCGAATCCATCTCT |
| 8 | 4353 VL CDR3 | QQNNNWPTT |
| 48 | | CAGCAGAACAATAACTGGCCCACCACA |
| 9 | 4353 LC CL | RTVAAPSVFIFPPSDEQLKSGTASVVCLLNNFYPREAKVQWKVDNALQSGNSQESVTEQDSKDSTYSLSSTL TLSKADYEKHKVYACEVTHQGLSSPVIKSFNRGEC |
| 49 | | CGAACAGTGGCCGCTCCTTCTGTCTTCATCTTTCCCCCTAGTGACGAACAGCTGAAAAGCGGCACAGCCTCC GTGGTCTGTCTGCTGAATAACTTTTACCCAAGAGAGGCAAAGGTGCAGTGGAAAGTCGATAATGCCCTGCAG TCAGGGAACAGCCAGGAGTCCGTGACTGAACAGGACTCTAAGGATAGTACCTATTCACTGAGCTCCACTCTG ACCCTGTCCAAAGCTGATTACGAGAAGCACAAAGTGTATGCATGCGAAGTCACCCATCAGGGGCTGTCTAGT CCCGTGACAAAGAGCTTTAACCGGGGAGAGTGT |
| 10 | 4353 HC CH1 | ASTKGPSVFPLAPSSKSTSGGTAALGCLVKDIFPEPVTVSWNSGALTSGVHTFPAVLQSSGLYSLSSVVTVP SSSLGTQTYICNVNHKPSNTKVDKKV |
| 50 | | GCTAGTACCAAGGGACCAAGCGTGTTTCCACTGGCACCAAGCTCCAAATCAACCAGCGGAGGCACAGCAGCC CTGGGATGTCTGGTGAAGGACTACTTCCCAGAGCCCGTCACAGTGTCATGGAACAGCGGCGCACTGACATCC GGGGTCCATACTTTTCCTGCCGTGCTGCAGTCTAGTGGCCTGTACTCTCTGTCAAGCGTGGTCACCGTGCCA TCCTCTAGTCTGGGGACACAGACTTATATCTGCAACGTGAATCACAAGCCTTCCAATACAAAAGTCGACAAG AAAGTG |
| 11 | 4353 | EPKSCDKTHTCPPCPAPELLGGP |
| 51 | Hinge-1 | GAACCAAAGTCTTGTGATAAAACCCATACATGCCCACCTTGTCCTGCACCAGAGCTGCTGGGAGGACCA |
| 12 | 4353 | EPKSSDKTHTCPPCPAPELLGGP |
| 52 | Hinge-2 | GAACCTAAAAGCAGCGACAAGACCCACACATGCCCCCCTTGTCCAGCTCCAGAACTGCTGGGAGGACCA |
| 13 | 4353 CH2-1 | SVFLFPPKPKDTLMISRTPEVICVVVDVSHEDPEVKFNWYVDGVEVHNAKTKPREEQYNSTYRVVSVLTVLH QDWLNGKEYKCKVSNKALPAPIEKTISKAK |

TABLE B-continued

SEQUENCES

| SEQ ID NO | DESCRIPTION | SEQUENCE |
|---|---|---|
| 53 | | TCCGTGTTCCTGTTTCCACCCAAGCCCAAAGACACCCTGATGATTTCCCGCACTCCAGAAGTCACCTGCGTG GTCGTGGACGTGTCTCACGAGGACCCCGAAGTCAAGTTCAACTGGTACGTGGATGGCGTCGAGGTGCATAAT GCCAAGACAAAACCACGGGAGGAACAGTACAATAGTACTTATAGAGTCGTGTCAGTCCTGACCGTGCTGCAC CAGGACTGGCTGAACGGCAAGGAGTATAAGTGCAAAGTGAGCAATAAGGCCCTGCCCGCTCCTATCGAGAAA ACCATTAGCAAGGCAAAA |
| 14 | 4353 CH2-2 | SVFLFPPKPKDTLMISRTPEVICVVVDVSHEDPEVKFNWYVDGVEVHNAKTKPREEQYNSTYRVVSVLTVLH QDWLNGKEYKCKVSNKALPAPIEKTISKAK |
| 54 | | AGCGTGTTCCTGTTTCCACCCAAGCCCAAAGATACACTGATGATCAGCCGAACTCCCGAGGTCACCTGCGTG GTCGTGGACGTGTCCCACGAGGACCCCGAAGTCAAGTTCAACTGGTACGTGGACGGCGTCGAAGTGCATAAT GCAAAGACTAAACCACGGGAGGAACAGTACAACTCTACATATAGAGTCGTGAGTGTCCTGACTGTGCTGCAT CAGGATTGGCTGAACGGCAAAGAGTATAAGTGCAAAGTGTCTAATAAGGCCCTGCCTGCTCCAATCGAGAAA ACTATTAGTAAGGCAAAA |
| 15 | 4353 CH3-1 | GQPREPQVYVYPPSRDELTKNQVSLTCLVKGFYPSDIAVEWESNGQPENNYKTTPPVLDSDGSFALVSKLTV DKSRWQQGNVFSCSVMHEALHNHYTQKSLSLSPGK |
| 55 | | GGGCAGCCTAGGGAACCACAGGTCTACGTGTATCCTCCATCACGCGACGAGCTGACCAAGAACCAGGTCAGC CTGACATGTCTGGTGAAAGGGTTTTACCCCTCTGATATCGCTGTGGAGTGGGAAAGTAATGGACAGCCTGAA AACAATTATAAGACCACACCCCCTGTGCTGGACTCCGATGGATCTTTCGCCCTGGTCAGCAAGCTGACTGTG GATAAATCCAGGTGGCAGCAGGGCAACGTCTTTTCCTGTTCTGTGATGCATGAGGCTCTGCACAATCATTAC ACCCAGAAGAGTCTGTCACTGAGCCCTGGCAAA |
| 16 | 4353 CH3-2 | GQPREPQVYVLPPSRDELTKNQVSLLCLVKGFYPSDIAVEWESNGQPENNYLTWPPVLDSDGSFFLYSKLTV DKSRWQQGNVFSCSVMHEALHNHYTQKSLSLSPGK |
| 56 | | GGGCAGCCCAGGGAACCTCAGGTCTACGTGCTGCCTCCAAGTCGCGACGAGCTGACCAAGAACCAGGTCTCA CTGCTGTGTCTGGTGAAAGGATTCTATCCTTCCGATATTGCCGTGGAGTGGGAATCTAATGGCCAGCCAGAG AACAATTACCTGACCTGGCCCCCTGTGCTGGACAGCGATGGGTCCTTCTTTCTGTATTCAAAGCTGACAGTG GACAAAAGCAGATGGCAGCAGGGAAACGTCTTTAGCTGTTCCGTGATGCACGAAGCCCTGCACAATCATTAC ACCCAGAAGTCTCTGAGTCTGTCACCTGGCAAA |
| 17 | 4353 HC-1-Full | QVQLKQSGPGLVQPSQSLSITCTVSGFSLTNYGVHWVRQSPGKGLEWLGVIWSGGNTDINTPFTSRLSINKD NSKSQVFFKMNSLQSNDTAIYYCARALTYYDIEFAYWGQGTLVTVSAASTKGPSVFPLAPSSKSTSGGTAAL GCLVKDIFPEPVTVSWNSGALTSGVHTFPAVLQSSGLYSLSSVVTVPSSSLGTQTYICNVNHKPSNTKVDKK VEPKSCDKTHTCPPCPAPELLGGPSVFLFPPKPKDILMISRTPEVTCVVVDVSHEDPEVKFNWYVDGVEVHN AKTKPREEQYNSTYRVVSVLTVLHQDWLNGKEYKCKVSNKALPAPIEKTISKAKGQPREPQVYVYPPSRDEL TKNQVSLTCLVKGFYPSDIAVEWESNGQPENNYKTTPPVLDSDGSFALVSKLTVDKSRWQQGNVFSCSVMHE ALHNHYTQKSLSLSPGK |
| 18 | 4353 HC-2-Full | EPKSSDKTHTCPPCPAPELLGGPSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTISKAKGQPREPQVYVLPPSRDELT KNQVSLLCLVKGFYPSDIAVEWESNGQPENNYLTWPPVLDSDGSFFLYSKLTVDKSRWQQGNVFSCSVMHEA LHNHYTQKSLSLSPGK |
| 57 | | GAACCTAAAAGCAGCGACAAGACCCACACATGCCCCCCTTGTCCAGCTCCAGAACTGCTGGGAGGACCAAGC GTGTTCCTGTTTCCACCCAAGCCCAAAGATACACTGATGATCAGCCGAACTCCCGAGGTCACCTGCGTGGTC GTGGACGTGTCCCACGAGGACCCCGAAGTCAAGTTCAACTGGTACGTGGACGGCGTCGAAGTGCATAATGCA AAGACTAAACCACGGGAGGAACAGTACAACTCTACATATAGAGTCGTGAGTGTCCTGACTGTGCTGCATCAG GATTGGCTGAACGGCAAAGAGTATAAGTGCAAAGTGTCTAATAAGGCCCTGCCTGCTCCAATCGAGAAAACT ATTAGTAAGGCAAAAGGGCAGCCCAGGGAACCTCAGGTCTACGTGCTGCCTCCAAGTCGCGACGAGCTGACC AAGAACCAGGTCTCACTGCTGTGTCTGGTGAAAGGATTCTATCCTTCCGATATTGCCGTGGAGTGGGAATCT AATGGCCAGCCAGAGAACAATTACCTGACCTGGCCCCCTGTGCTGGACAGCGATGGGTCCTTCTTTCTGTAT TCAAAGCTGACAGTGGACAAAAGCAGATGGCAGCAGGGAAACGTCTTTAGCTGTTCCGTGATGCACGAAGCC CTGCACAATCATTACACCCAGAAGTCTCTGAGTCTGTCACCTGGCAAA |
| 19 | 4353 LC-Full | DILLTQSPVILSVSPGERVSFSCRASQSIGTNIHWYQQRTNGSPRLLIKYASESISGIPSRFSGSGSGTDFT LSINSVESEDIADYYCQQNNNWPTTFGAGTKLELKRTVAAPSVFIFPPSDEQLKSGTASVVCLLNNFYPREA KVQWKVDNALQSGNSQESVTEQDSKDSTYSLSSTLTLSKADIEKHKVYACEVTHQGLSSPVTKSFNRGEC |
| 58 | | GACATCCTGCTGACTCAGAGCCCAGTGATCCTGTCAGTCAGCCCAGGAGAGCGGGTGTCCTTCTCTTGCAGA GCAAGTCAGTCAATCGGAACAAATATTCACTGGTACCAGCAGAGGACTAACGGCTCCCCTCGCCTGCTGATT AAGTATGCTAGCGAATCCATCTCTGGCATTCCATCTCGGTTCAGTGGCTCAGGGAGCGGAACAGACTTTACT CTGTCCATCAATTCTGTGGAGAGTGAAGACATTGCCGATTACTATTGCCAGCAGAACAATAACTGGCCCACC ACATTCGGCGCTGGGACCAAGCTGGAGCTGAAACGAACAGTGGCCGCTCCTTCTGTCTTCATCTTTCCCCCT AGTGACGAACAGCTGAAAAGCGGCACAGCCTCCGTGGTCTGTCTGCTGAATAACTTTTACCCAAGAGAGGCA AAGGTGCAGTGGAAAGTCGATAATGCCCTGCAGTCAGGGAACAGCCAGGAGTCCGTGACTGAACAGGACTCT AAGGATAGTACCTATTCACTGAGCTCCACTCTGACCCTGTCCAAAGCTGATTACGAGAAGCACAAAGTGTAT GCATGCGAAGTCACCCATCAGGGGCTGTCTAGTCCCGTGACAAAGAGCTTTAACCGGGGAGAGTGT |
| 20 | 1323 VHH | QVKLEESGGGLVQAGDSLRVSCAASGRDFSDYVMGWFRQAPGKEREFVAAISRNGLTTRYADSVKGRFTISR DNDKNMVYLQMNSLKPEDTAVYYCAVNSAGTYVSPRSREYDYWGQGTQVIVSS |

TABLE B-continued

SEQUENCES

| SEQ ID NO | DESCRIPTION | SEQUENCE |
|---|---|---|
| 21 | 1323 VHH CDR1 | GRDFSDYVMG |
| 22 | 1323 VHH CDR2 | ISRNGLTT |
| 23 | 1323 VHH CDR3 | NSAGTYVSPRSREYDY |
| 24 | 1323 Hinge-1 | EPKSCDKTHTCPPCPAPELLGGP |
| 25 | 1323 Hinge-2 | EPKSSDKTHTCPPCPAPELLGGP |
| 59 | | GAACCTAAAAGCAGCGACAAGACCCACACATGCCCCCCTTGTCCAGCTCCAGAACTGCTGGGAGGACCA |
| 26 | 1323 CH2-1 | SVFLEPPKPKDTLMISRTPEVTCVVVDVSHEDPEVKFNWYVDGVEVHNAKTKPREEQYNSTYRVVSVLTVLH QDWLNGKEYKCKVSNKALPAPIEKTISKAK |
| 27 | 1323 CH2-2 | SVFLEPPKPKDTLMISRTPEVICVVVDVSHEDPEVKFNWYVDGVEVHNAKTKPREEQYNSTYRVVSVLTVLH QDWLNGKEYKCKVSNKALPAPIEKTISKAK |
| 60 | | AGCGTGTTCCTGTTTCCACCCAAGCCCAAAGATACACTGATGATCAGCCGAACTCCCGAGGTCACCTGCGTG GTCGTGGACGTGTCCCACGAGGACCCCGAAGTCAAGTTCAACTGGTACGTGGACGGCGTCGAAGTGCATAAT GCAAAGACTAAACCACGGGAGGAACAGTACAACTCTACATATAGAGTCGTGAGTGTCCTGACTGTGCTGCAT CAGGATTGGCTGAACGGCAAAGAGTATAAGTGCAAAGTGTCTAATAAGGCCCTGCCTGCTCCAATCGAGAAA ACTATTAGTAAGGCAAAA |
| 28 | 1323 CH3-1 | GQPREPQVYVYPPSRDELTKNQVSLTCLVKGFYPSDIAVEWESNGQPENNYKTTPPVLDSDGSFALVSKLTV DKSRWQQGNVFSCSVMHEALHNHITQKSLSLSPGK |
| 29 | 1323 CH3-2 | GQPREPQVYVLPPSRDELTKNQVSLLCLVKGFYPSDIAVEWESNGQPENNYLTWPPVLDSDGSFFLYSKLTV DKSRWQQGNVFSCSVMHEALHNHYTQKSLSLSPGK |
| 61 | | GGGCAGCCCAGGGAACCTCAGGTCTACGTGCTGCCTCCAAGTCGCGACGAGCTGACCAAGAACCAGGTCTCA CTGCTGTGTCTGGTGAAAGGATTCTATCCTTCCGATATTGCCGTGGAGTGGGAATCTAATGGCCAGCCAGAG AACAATTACCTGACCTGGCCCCCTGTGCTGGACAGCGATGGGTCCTTCTTTCTGTATTCAAAGCTGACAGTG GACAAAAGCAGATGGCAGCAGGGAAACGTCTTTAGCTGTTCCGTGATGCACGAAGCCCTGCACAATCATTAC ACCCAGAAGTCTCTGAGTCTGTCACCTGGCAAA |
| 30 | 1323 HC-1-Full | |
| 31 | 1323 HC-2-Full | EPKSSDKTHTCPPCPAPELLGGPSVFLFPPKPKDTLMISRTPEVICVVVDVSHEDPEVKFNWYVDGVEVHNA KTKPREEQYNSTYRVVSVLTVLHQDWLNGKEYKCKVSNKALPAPIEKTISKAKGQPREPQVYVLPPSRDELT KNQVSLLCLVKGFYESDIAVEWESNGQPENNYLTWPPVLDSDGSFELYSKLTVDKSRWQQGNVFSCSVMHEA LHNHITQKSLSLSPGK |
| 62 | | GAACCTAAAAGCAGCGACAAGACCCACACATGCCCCCCTTGTCCAGCTCCAGAACTGCTGGGAGGACCAAGC GTGTTCCTGTTTCCACCCAAGCCCAAAGATACACTGATGATCAGCCGAACTCCCGAGGTCACCTGCGTGGTC GTGGACGTGTCCCACGAGGACCCCGAAGTCAAGTTCAACTGGTACGTGGACGGCGTCGAAGTGCATAATGCA AAGACTAAACCACGGGAGGAACAGTACAACTCTACATATAGAGTCGTGAGTGTCCTGACTGTGCTGCATCAG GATTGGCTGAACGGCAAAGAGTATAAGTGCAAAGTGTCTAATAAGGCCCTGCCTGCTCCAATCGAGAAAACT ATTAGTAAGGCAAAAGGGCAGCCCAGGGAACCTCAGGTCTACGTGCTGCCTCCAAGTCGCGACGAGCTGACC AAGAACCAGGTCTCACTGCTGTGTCTGGTGAAAGGATTCTATCCTTCCGATATTGCCGTGGAGTGGGAATCT AATGGCCAGCCAGAGAACAATTACCTGACCTGGCCCCCTGTGCTGGACAGCGATGGGTCCTTCTTTCTGTAT TCAAAGCTGACAGTGGACAAAAGCAGATGGCAGCAGGGAAACGTCTTTAGCTGTTCCGTGATGCACGAAGCC CTGCACAATCATTACACCCAGAAGTCTCTGAGTCTGTCACCTGGCAAA |
| 32 | OA-Tras HC-1 | EVQLVESGGGLVQPGGSLRLSCAASGFNIKDTYIHWVRQAPGKGLEWVARIYPTNGYTRYADSVKGRFTISA DTSKNTAYLQMNSLRAEDTAVYYCSRWGGDGFYAMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPREPQVYVYPPSRDE LTKNQVSLTCLVKGFYPSDIAVEWESNGQPENNYKTTPPVLDSDGSFALVSKLTVDKSRWQQGNVFSCSVMH EALHNHYTQKSLSLSPGK |
| 63 | | GAAGTCCAGCTGGTCGAAAGCGGAGGAGGACTGGTGCAGCCAGGAGGGTCTCTGCGACTGAGTTGCGCCGCT TCAGGCTTCAACATCAAGGACACCTACATTCACTGGGTGCGCCAGGCTCCTGGAAAAGGCCTGGAGTGGGTG GCACGAATCTATCCAACTAATGGATACACCCGGTATGCAGACAGCGTGAAGGGCCGGTTCACCATTAGCGCA GATACATCCAAAAACACTGCCTACCTGCAGATGAACAGCCTGCGAGCCGAAGATACTGCTGTGTACTATTGC AGTCGGTGGGGAGGCGACGGCTTCTACGCTATGGATTATTGGGGGCAGGGAACCCTGGTCACAGTGAGCTCC GCATCTACAAAGGGGCCTAGTGTGTTTCCACTGGCCCCCTCTAGTAAATCCACCTCTGGGGGAACAGCAGCC CTGGGATGTCTGGTGAAGGACTATTTCCCAGAGCCCGTCACTGTGAGTTGGAACTCAGGCGCCCTGACATCC GGGGTCCATACTTTTCCTGCTGTGCTGCAGTCAAGCGGCCTGTACTCTCTGTCCTCTGTGGTCACCGTGCCA AGTTCAAGCCTGGGGACTCAGACCTATATCTGCAACGTGAATCACAAGCCAAGCAATACAAAAGTCGACAAG AAAGTGGAACCCAAGAGCTGTGATAAAACACATACTTGCCCCCCTTGTCCTGCACCAGAGCTGCTGGGAGGA CCATCCGTGTTCCTGTTTCCACCCAAGCCTAAAGACACCCTGATGATTTCCAGGACTCCAGAAGTCACCTGC GTGGTCGTGGACGTGTCTCACGAGGACCCCGAAGTCAAGTTCAACTGGTACGTGGATGGCGTCGAGGTGCAT |

TABLE B-continued

SEQUENCES

| SEQ ID NO | DESCRIPTION | SEQUENCE |
|---|---|---|
| | | AATGCCAAGACAAAACCCAGGGAGGAACAGTACAACTCAACTTATCGCGTCGTGAGCGTCCTGACCGTGCTG<br>CACCAGGACTGGCTGAACGGCAAGGAGTATAAGTGCAAAGTGAGCAATAAGGCTCTGCCCGCACCTATCGAG<br>AAAACCATTAGCAAGGCCAAAGGGCAGCCTAGAGAACCACAGGTCTACGTGTATCCTCCAAGCAGGGACGAG<br>CTGACCAAGAACCAGGTCTCCCTGACATGTCTGGTGAAAGGGTTTTACCCCAGTGATATCGCTGTGGAGTGG<br>GAATCAAATGGACAGCCTGAAAACAATTATAAGACCACACCCCCTGTGCTGGACAGCGATGGCAGCTTCGCT<br>CTGGTCTCCAAGCTGACTGTGGATAAATCTCGGTGGCAGCAGGGCAACGTCTTTAGTTGTTCAGTGATGCAT<br>GAGGCACTGCACAATCATTACACCCAGAAGAGCCTGTCCCTGTCTCCCGGCAAA |
| 33 | OA-Tras HC-2 | EPKSSDKTHTCPPCPAPELLGGPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREPQVYVLPPSRDELT<br>KNQVSLLCLVKGFYPSDIAVEWESNGQPENNYLTWPPVLDSDGSFFLYSKLTVDKSRWQQGNVFSCSVMHEA<br>LHNHYTQKSLSLSPGK |
| 64 | | GAACCTAAAAGCAGCGACAAGACCCACACATGCCCCCCTTGTCCAGCTCCAGAACTGCTGGGAGGACCAAGC<br>GTGTTCCTGTTTCCACCCAAGCCCAAAGATACACTGATGATCAGCCGAACTCCCGAGGTCACCTGCGTGGTC<br>GTGGACGTGTCCCACGAGGACCCCGAAGTCAAGTTCAACTGGTACGTGGACGGCGTCGAAGTGCATAATGCA<br>AAGACTAAACCACGGGAGGAACAGTACAACTCTACATATAGAGTCGTGAGTGTCCTGACTGTGCTGCATCAG<br>GATTGGCTGAACGGCAAAGAGTATAAGTGCAAAGTGTCTAATAAGGCCCTGCCTGCTCCAATCGAGAAAACT<br>ATTAGTAAGGCAAAAGGGCAGCCCAGGGAACCTCAGGTCTACGTGCTGCCTCCAAGTCGCGACGAGCTGACC<br>AAGAACCAGGTCTCACTGCTGTGTCTGGTGAAAGGATTCTATCCTTCCGATATTGCCGTGGAGTGGGAATCT<br>AATGGCCAGCCAGAGAACAATTACCTGACCTGGCCCCCTGTGCTGGACAGCGATGGGTCCTTCTTTCTGTAT<br>TCAAAGCTGACAGTGGACAAAAGCAGATGGCAGCAGGGAAACGTCTTTAGCTGTTCCGTGATGCACGAAGCC<br>CTGCACAATCATTACACCCAGAAGTCTCTGAGTCTGTCACCTGGCAAA |
| 34 | OA-Tras LC | DIQMTQSPSSLSASVGDRVTITCRASQDVNTAVAWYQQKPGKAPKLLIYSASFLYSGVPSRFSGSRSGTDFT<br>LTISSLQPEDFATYYCQQHYTTPPTFGQGTKVEIKRTVAAPSVFIFPPSDEQLKSGTASVVCLLNNFYPREA<br>KVQWKVDNALQSGNSQESVTEQDSKDSTYSLSSTLTLSKADYEKHKVYACEVTHQGLSSPVTKSFNRGEC |
| 65 | | GATATTCAGATGACCCAGTCCCCTAGCTCCCTGTCCGCTTCTGTGGGCGACAGGGTCACTATCACCTGCCGC<br>GCATCTCAGGATGTGAACACCGCAGTCGCCTGGTACCAGCAGAAGCCTGGGAAAGCTCCAAAGCTGCTGATC<br>TACAGTGCATCATTCCTGTATTCAGGAGTGCCCAGCCGGTTTAGCGGCAGCAGATCTGGCACCGACTTCACA<br>CTGACTATCTCTAGTCTGCAGCCTGAGGATTTTGCCACATACTATTGCCAGCAGCACTATACCACACCCCCT<br>ACTTTCGGCCAGGGGACCAAAGTGGAGATCAAGCGAACTGTGGCCGCTCCAAGTGTCTTCATTTTTCCACCC<br>AGCGACGAACAGCTGAAATCCGGCACAGCTTCTGTGGTCTGTCTGCTGAACAACTTCTACCCCAGAGAGGCC<br>AAAGTGCAGTGGAAGGTCGATAACGCTCTGCAGAGTGGCAACAGCCAGGAGAGCGTGACAGAACAGGACTCC<br>AAAGATTCTACTTATAGTCTGTCAAGCACCCTGACACTGAGCAAGGCAGACTACGAAAAGCATAAAGTGTAT<br>GCCTGTGAGGTGACCCATCAGGGGCTGTCTTCTCCCGTGACCAAGTCTTTCAACCGAGGCGAATGT |
| 35 | OA-Pert HC-1 | EVQLVESGGGLVQPGGSLRLSCAASGFTFTDYTMDWVRQAPGKGLEWVADVNPNSGGSIYNQRFKGRFTLSV<br>DRSKNTLYLQMNSLRAEDTAVYYCARNLGPSFYFDYWGQGTLVTVSSASTKGPSVFPLAPSSKSTSGGTAAL<br>GCLVKDYFPEPVTVSWNSGALTSGVHTFPAVLQSSGLYSLSSVVTVPSSSLGTQTYICNVNHKPSNTKVDKK<br>VEPKSCDKTHTCPPCPAPELLGGPSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKTISKAKGQPREPQVYVYPPSRDEL<br>TKNQVSLTCLVKGFYPSDIAVEWESNGQPENNYKTTPPVLDSDGSFALVSKLTVDKSRWQQGNVFSCSVMHE<br>ALHNHITQKSLSLSPG |
| 66 | | GAAGTGCAGCTGGTCGAATCTGGAGGAGGACTGGTGCAGCCAGGAGGGTCCCTGCGCCTGTCTTGCGCCGCT<br>AGTGGCTTCACTTTTACCGACTACACCATGGATTGGGTGCGACAGGCACCTGGAAAGGGCCTGGAGTGGGTC<br>GCCGATGTGAACCCAAATAGCGGAGGCTCCATCTACAACCAGCGGTTCAAGGGCCGGTTCACCCTGTCAGTG<br>GACCGGAGCAAAAACACCCTGTATCTGCAGATGAATAGCCTGCGAGCCGAAGATACTGCTGTGTACTATTGC<br>GCCCGGAATCTGGGGCCCTCCTTCTACTTTGACTATTGGGGGCAGGGAACTCTGGTCACCGTGAGCTCCGCC<br>TCCACCAAGGGACCTTCTGTGTTCCCACTGGCTCCCTCTAGTAAATCCACATCTGGGGGAACTGCAGCCCTG<br>GGCTGTCTGGTGAAGGACTACTTCCCAGAGCCCGTCACAGTGTCTTGGAACAGTGGCGCTCTGACTTCTGGG<br>GTCCACACCTTTCCTGCAGTGCTGCAGTCAAGCGGGCTGTACAGCCTGTCCTCTGTGGTCACCGTGCCAAGT<br>TCAAGCCTGGGAACACAGACTTATATCTGCAACGTGAATCACAAGCCATCCAATACAAAAGTCGACAAGAAA<br>GTGGAACCCAAGTCTTGTGATAAAACCCATACATGCCCCCCTTGTCCTGCACCAGAGCTGCTGGGAGGACCA<br>AGCGTGTTCCTGTTTCCACCCAAGCCTAAAGATACACTGATGATTAGTAGGACCCCAGAAGTCACATGCGTG<br>GTCGTGGACGTGAGCCACGAGGACCCCGAAGTCAAGTTTAACTGGTACGTGGACGGCGTCGAGGTGCATAAT<br>GCCAAGACTAAACCCAGGGAGGAACAGTACAACAGTACCTATCGCGTCGTGTCAGTCCTGACAGTGCTGCAT<br>CAGGATTGGCTGAACGGGAAAGAGTATAAGTGCAAAGTGAGCAATAAGGCTCTGCCCGCACCTATCGAGAAA<br>ACAATTTCCAAGGCAAAAGGACAGCCTAGAGAACCACAGGTGTACGTGTATCCTCCATCAAGGGATGAGCTG<br>ACAAAGAACCAGGTCAGCCTGACTTGTCTGGTGAAAGGATTCTATCCCTCTGACATTGCTGTGGAGTGGGAA<br>AGTAATGGCCAGCCTGAGAACAATTACAAGACCACACCCCCTGTGCTGGACTCAGATGGCAGCTTCGCGCTG<br>GTGAGCAAGCTGACCGTCGACAAATCCCGGTGGCAGCAGGGGAATGTGTTTAGTTGTTCAGTCATGCACGAG<br>GCACTGCACAACCATTACACCCAGAAGTCACTGTCACTGTCACCAGGG |
| 36 | OA-Pert HC-2 | EPKSSDKTHTCPPCPAPELLGGPSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTISKAKGQPREPQVYVLPPSRDELT<br>KNQVSLLCLVKGFYPSDIAVEWESNGQPENNYLTWPPVLDSDGSFFLYSKLTVDKSRWQQGNVFSCSVMHEA<br>LHNHYTQKSLSLSPGK |
| 67 | | GAACCTAAAAGCAGCGACAAGACCCACACATGCCCCCCTTGTCCAGCTCCAGAACTGCTGGGAGGACCAAGC<br>GTGTTCCTGTTTCCACCCAAGCCCAAAGATACACTGATGATCAGCCGAACTCCCGAGGTCACCTGCGTGGTC<br>GTGGACGTGTCCCACGAGGACCCCGAAGTCAAGTTCAACTGGTACGTGGACGGCGTCGAAGTGCATAATGCA |

TABLE B-continued

| SEQUENCES | | |
|---|---|---|
| SEQ ID NO | DESCRIPTION | SEQUENCE |
| | | AAGACTAAACCACGGGAGGAACAGTACAACTCTACATATAGAGTCGTGAGTGTCCTGACTGTGCTGCATCAG<br>GATTGGCTGAACGGCAAAGAGTATAAGTGCAAAGTGTCTAATAAGGCCCTGCCTGCTCCAATCGAGAAAACT<br>ATTAGTAAGGCAAAAGGGCAGCCCAGGGAACCTCAGGTCTACGTGCTGCCTCCAAGTCGCGACGAGCTGACC<br>AAGAACCAGGTCTCACTGCTGTGTCTGGTGAAAGGATTCTATCCTTCCGATATTGCCGTGGAGTGGGAATCT<br>AATGGCCAGCCAGAGAACAATTACCTGACCTGGCCCCCTGTGCTGGACAGCGATGGGTCCTTCTTTCTGTAT<br>TCAAAGCTGACAGTGGACAAAAGCAGATGGCAGCAGGGAAACGTCTTTAGCTGTTCCGTGATGCACGAAGCC<br>CTGCACAATCATTACACCCAGAAGTCTCTGAGTCTGTCACCTGGCAAA |
| 37 | OA-Pert LC | DIQMTQSPSSLSASVGDRVTITCKASQDVSIGVAWYQQKPGKAPKLLIYSASYRYTGVPSRFSGSGSGTDFT<br>LTISSLQPEDFATYYCQQYYIYPYTFGQGTKVEIKRTVAAPSVFIFPPSDEQLKSGTASVVCLLNNFYPREA<br>KVQWKVDNALQSGNSQESVTEQDSKDSTYSLSSTLTLSKADYEKHKVYACEVTHQGLSSPVTKSFNRGEC |
| 68 | | GATATTCAGATGACCCAGTCCCCAAGCTCCCTGAGTGCCTCAGTGGGCGACCGAGTCACCATCACATGCAAG<br>GCTTCCCAGGATGTGTCTATTGGAGTCGCATGGTACCAGCAGAAGCCAGGCAAAGCACCCAAGCTGCTGATC<br>TATAGCGCCTCCTACCGGTATACCGGCGTGCCCTCTAGATTCTCTGGCAGTGGGTCAGGAACAGACTTTACT<br>CTGACCATCTCTAGTCTGCAGCCTGAGGATTTCGCTACCTACTATTGCCAGCAGTACTATATCTACCCATAT<br>ACCTTTGGCCAGGGGACAAAAGTGGAGATCAAGAGGACTGTGGCCGCTCCCTCCGTCTTCATTTTTCCCCCT<br>TCTGACGAACAGCTGAAAAGTGGCACAGCCAGCGTGGTCTGTCTGCTGAACAATTTCTACCCTCGCGAAGCC<br>AAAGTGCAGTGGAAGGTCGATAACGCTCTGCAGAGCGGCAACAGCCAGGAGTCTGTGACTGAACAGGACAGT<br>AAAGATTCAACCTATAGCCTGTCAAGCACACTGACTCTGAGCAAGGCAGACTACGAGAAGCACAAAGTGTAT<br>GCCTGCGAAGTCACACATCAGGGGCTGTCCTCTCCTGTGACTAAGAGCTTTAACAGAGGAGAGTGT |
| 38 | HER2 ECDs<br>Domain 1: 1-165<br>Domain 2: 166-322<br>Domain 3: 323-488<br>Domain 4: 489-607 | tqvctgtdmk lrlpaspeth ldmlrhlyqg cqvvqgnlel tylptnasls<br>flqdiqevqg yvliahnqvr qvplqrlriv rgtqlfedny alavldngdp<br>lnnttpvtga spgglrelql rslteilkgg vliqrnpqlc yqdtilwkdi<br>fhknnqlalt lidtnrsrac hpcspmckgs rcwgessedc qsltrtvcag<br>gcarckgplp tdccheqcaa gctgpkhsdc laclhfnhsg icelhcpalv<br>tyntdtfesm pnpegrytfg ascvtacpyn ylstdvgsct lvcplhnqev<br>taedgtqrce kcskpcarvc yglgmehlre vravtsaniq efagckkifg<br>slaflpesfd gdpasntapl qpeqlqvfet leeitgylyi sawpdslpdl<br>svfqnlqvir grilhngays ltlqglgisw lglrslrelg sglalihhnt<br>hlcfvhtvpw dqlfrnphqa llhtanrped ecvgeglach qlcarghcwg<br>pgptqcvncs qflrgqecve ecrvlqglpr eyvnarhclp chpecqpqng<br>svtcfgpead qcvacahykd ppfcvarcps gvkpdlsymp iwkfpdeega<br>cqpcpin |
| 39 | EGFR ECD<br>comprises 621 aa,<br>from aa 25-645 of<br>the full length<br>unprocessed sequence<br>ECD1 is 1-165<br>ECD2 is 166-310<br>ECD3 is 311-480<br>ECD4 is 481-621 | LEEKKVCQGTSNKLTQLGTFEDHFLSLQRMFNNCEVVLGNLEITYVQRNYDLSFLKTI<br>QEVAGYVLIALNTVERIPLENLQIIRGNMYYENSYALAVLSNYDANKTGLKELPMRNL<br>QEILHGAVRFSNNPALCNVESIQWRDIVSSDFLSNMSMDFQNHLGSCQKCDPSCPNGS<br>CWGAGEENCQKLTKIICAQQCSGRCRGKSPSDCCHNQCAAGCTGPRESDCLVCRKFRD<br>EATCKDTCPPLMLYNPTTYQMDVNPEGKYSFGATCVKKCPRNYVVTDHGSCVRACGAD<br>SYEMEEDGVRKCKKCEGPCRKVCNGIGIGEFKDSLSINATNIKHFKNCTSISGDLHIL<br>PVAFRGDSFTHTPPLDPQELDILKTVKEITGFLLIQAWPENRTDLHAFENLEIIRGRT<br>KQHGQFSLAVVSLNITSLGLRSLKEISDGDVIISGNKNLCYANTINWKKLFGTSGQKT<br>KIISNRGENSCKATGQVCHALCSPEGCWGPEPRDCVSCRNVSRGRECVDKCNLLEGEP<br>REFVENSECIQCHPECLPQAMNITCTGRGPDNCIQCAHYIDGPHCVKTCPAGVMGENN<br>TLVWKYADAGHVCHLCHPNCTYGCTGPGLEGCPTNGPKIPS |

Final expressed sequences excluding the signal peptide

Example 2: Expression and Purification of OA-EGFR Antibodies and Controls

The OA-EGFR antibodies and controls described in Example 1 were expressed and purified in 50 mL cultures as follows.

The genes encoding the antibody heavy and light chains were constructed via gene synthesis using codons optimized for human/mammalian expression. The final gene products were sub-cloned into the mammalian expression vector pTT5 (NRC-BRI, Canada) and expressed in CHO cells (Durocher, Y., Perret, S. & Kamen, A. High-level and high-throughput recombinant protein production by transient transfection of suspension-growing CHO cells. *Nucleic acids research* 30, E9 (2002)). The DNA of genes encoding the heavy and light chains of the antibody constructs were all generated by gene synthesis, except for v1323 which was cloned using standard molecular biology DNA recombination techniques.

The CHO cells were transfected in exponential growth phase (1.5 to 2 million cells/mL) with aqueous 1 mg/mL 25 kDa polyethylenimine (PEI, Polysciences) at a PEI:DNA ratio of 2.5:1. (Raymond C. et al. A simplified polyethylenimine-mediated transfection process for large-scale and high-throughput applications. Methods. 55(1):44-51 (2011)). In order to determine the optimal concentration range for forming Fc heterodimers, the DNA of the heavy chain A (HC-A), light chain (LC), and heavy chain B (HC-B) were initially transfected at different ratios. The optimal HC:Fc:LC DNA ratio of v4353 was 36:24:40. The optimal HC:Fc DNA ratio of v1323 was 60:40. Transfected cells were harvested after 5-6 days with the culture medium collected after centrifugation at 4000 rpm and clarified using a 0.45 μm filter.

The clarified culture medium was loaded onto a MabSelect SuRe (GE Healthcare) protein-A column and washed with 10 column volumes of PBS buffer at pH 7.2. The antibody was eluted with 10 column volumes of citrate buffer at pH 3.6 with the pooled fractions containing the antibody neutralized with TRIS at pH 11. The protein was then desalted using an Econo-Pac 10DG column (Bio-Rad).

The protein was further purified by gel filtration, 3.5 mg of the antibody mixture was concentrated to 1.5 mL and loaded onto a Superdex 200 HiLoad 16/600 200pg column via an AKTA Express FPLC (GE Healthcare) at a flow-rate of 1 mL/min PBS buffer at pH 7.4 was used at a flow-rate of 1 mL/min Fractions corresponding to the purified antibody were collected, concentrated to ~1 mg/mL and stored at −80° C.

FIG. 1A shows the SEC profile of v4353 after protein A purification with the main peak at retention of 79.95. FIG. 1B shows the SEC profile of v1323 after protein A purification with the main peak at retention at 84.74. FIG. 1C shows the purity of both v4353 and v1323 after protein A and SEC purification as measured by non-reducing SDS-PAGE analysis with species at approximately 110 kDa and 66 kDa, respectively. Table 2 below provides a summary of the yield of antibodies through the purification process.

TABLE 2

| Variant HC-A/HC-B/LC | Conc after protein A mg/ml | Amount mg after protein A | Conc after GFC mg/ml | Amount mg after GFC |
|---|---|---|---|---|
| v4353 (36/24/40) | 1.43 | 6.4 | 0.65 | 2.47 |
| v1323 (60/40/0) | 2.79 | 11.16 | 0.8 | 3 |

When expressed using optimized DNA ratios, the exemplary one armed antibodies v4353 and v1323 did not show significant amounts of homodimer contaminants or high molecular weight aggregates, as seen in the SEC chromatogram following the protein A purifications step (FIGS. 1A and B). SDS-PAGE of the pooled SEC fractions indicated a high level of purity of the heterodimeric Fc (FIG. 1C). The purity was further confirmed to be over 95% by UPLC SEC and mass spectroscopy.

V4353 was scaled up to a 10 L production without problem, yielding titres up to 97.5 mg/L after protein A and SEC purification.

Example 3: OA-EGFR Antibodies Bind Specifically to EGFR

This experiment was performed to assess the ability of two exemplary OA-EGFR antibodies, v4353 and v1323 to specifically bind to EGFR. Specific binding to EGFR was measured using surface plasmon resonance (SPR) according to the method described below, using the BIAcore T200 instrument (GE Healthcare).

Anti-human IgG Fc antibody (Jackson ImmunoResearch, Cat. No. 109-005-098) was covalently coupled to the Series S Sensor chip CMS (Cat. No. BR-1005-30, GE Healthcare) via primary amine groups. The chip was first equilibrated with HBS-EP (10 mM HEPES pH 7.4, 150 mM NaCl, 3.4 mM EDTA, 0.005% surfactant P20) for 5 min at a flow rate of 10 μl/min. The chip was then activated by injecting a 1 to 1 mixture of NHS (N-hydroxysuccinimide) and EDC (1-ethyl-3-(3-dimethylaminopropyl) carbodiimide), flowed at 10 μl/min for 7 min. The capture antibody was then injected at a flow rate of 10 μl/min for 7 min, and finally the excess reactive groups were deactivated by injecting ethanolamine at a flow rate 10 μl/min for 7 min.

The antibody to antigen binding was tested as follows. The chip surface was first stabilized by 3 identical analysis cycles of HBS-EP running buffer. The sample antibody was injected for capture at 100 nM at 10 μl/min, for 20 s to 2 min to achieve a capture level of approximately 100 RU (response units). The chip was then equilibrated using the running buffer. The antigen, which was HER2 extracellular domain (ECD) or EGFR ECD, was then injected at increasing concentrations (e.g. from 1, 3, 9, 27 to 81 nM) for measuring antibody binding, at a flow rate 30 μl/min over 3 to 4 minutes. This was followed by a dissociation step, in which the running buffer was flowed at 30 μl/min for about 20 min or until the antigen is fully dissociated. The surface was regenerated with the running buffer twice, flowed at flow rate 10 μl/min for 0.5 min each time, followed by 6 regeneration buffer (glycine-HCL pH 1.7) injection cycles flowed at 10 μl/min, for 0.25 min. This was repeated using the next higher antigen concentration until a set of binding sensograms was complete.

Figure 2:
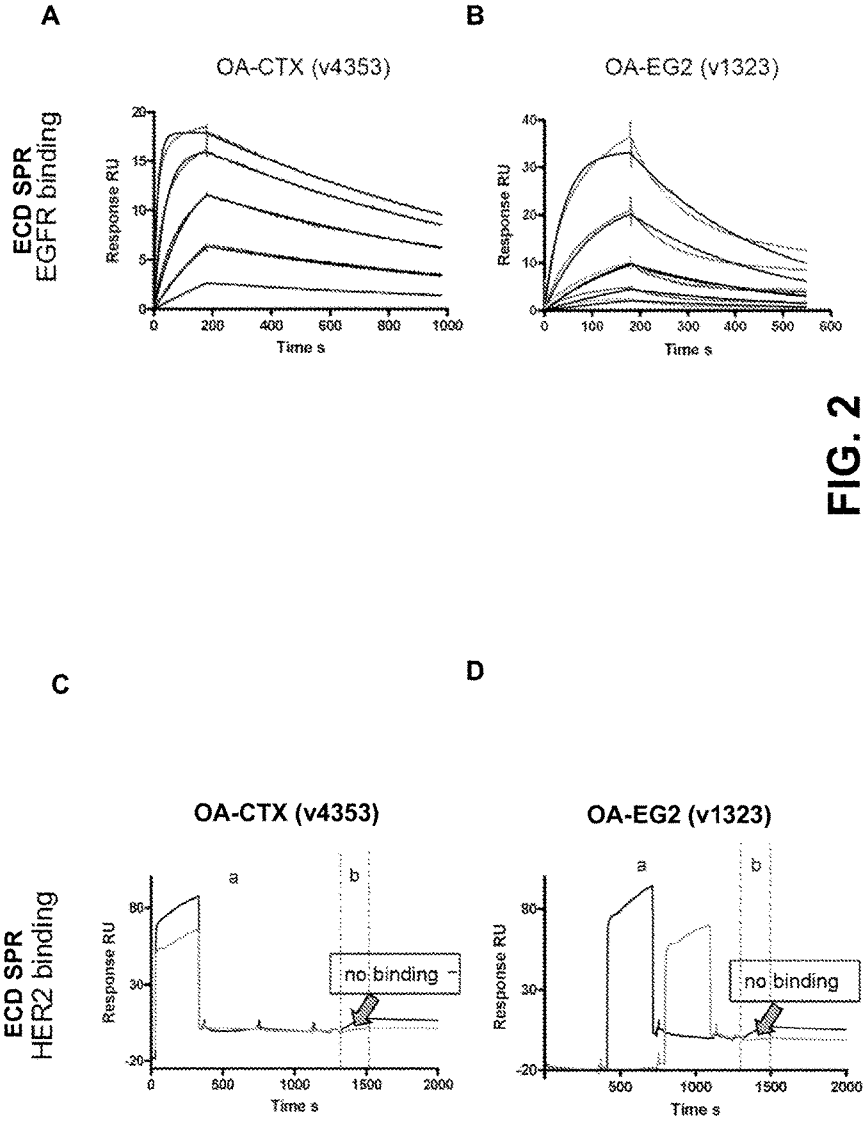
FIG. 2 depicts the ability of exemplary neutralizing and non-neutralizing OA-EGFR antibodies to bind to EGFR, as measured by Surface Plasmon Resonance (SPR).

The results are shown in FIGS. 2A to 2D. In FIGS. 2B and 2D, the absence of HER2 binding was confirmed in which subsection ‘a’ correspond to the sensorgram of the antibody capture and subsection ‘b’ correspond to the sensorgram following HER2 injection.

A summary of the EGFR binding characteristics for the OA-EGFR antibodies is shown in Table 3.

TABLE 3

| | ka (1/Ms) | kd (1/s) | KD (M) |
|---|---|---|---|
| v1323* | 3.11E+05 | 3.61E−03 | 1.16E−08 |
| v4353 | 9.22E+05 | 7.85E−04 | 8.51E−10 |

The binding of OA-CTX to EGFR was quantified by SPR with a $K_D$ of approximately 0.85 nM (FIG. 2A). This is comparable to the $K_D$ reported for cetuximab (1 nM) determined by similar SPR experiments using antibody capture protocols which characterizes the monovalent binding interactions. No binding was observed to HER2. The binding of OA-EG2 to EGFR was also determined, with a $K_D$ of approximately 12 nM. The binding of OA-EG2 was also specific to EGFR. Together, these results demonstrate that the one armed antibodies can bind different epitopes of EGFR by design and can retain the same monovalent binding affinity compared to the corresponding bivalent antibody from which they were derived.

Example 4: Ability of Exemplary OA-EGFR Antibodies to Bind to Cells Expressing a Low Level of EGFR (EGFR Low)

This experiment was performed in order to assess the binding of OA-EGFR antibodies to the breast BT-474 cancer cell line, a cell line that expresses low levels of EGFR (McDonagh et al Mol Cancer Ther. 2012 March; 11(3):582-93). The experiment was carried out as described below.

The BT-474 cells were incubated with various concentrations of antibodies, 8 concentration points distributed geometrically from 0.3 pM to 300 nM 4° C. for 1 hr. The cells were then washed 3 times with PBS, after which anti-human IgG-FITC was added in excess. The cells were further incubated for 1 hr at 4° C. in the dark, and washed again 3 times with PBS. Finally, the cells were resuspended in PBS and the MFI were measured using FACSCalibur (BD Biosciences).

Figure 3:
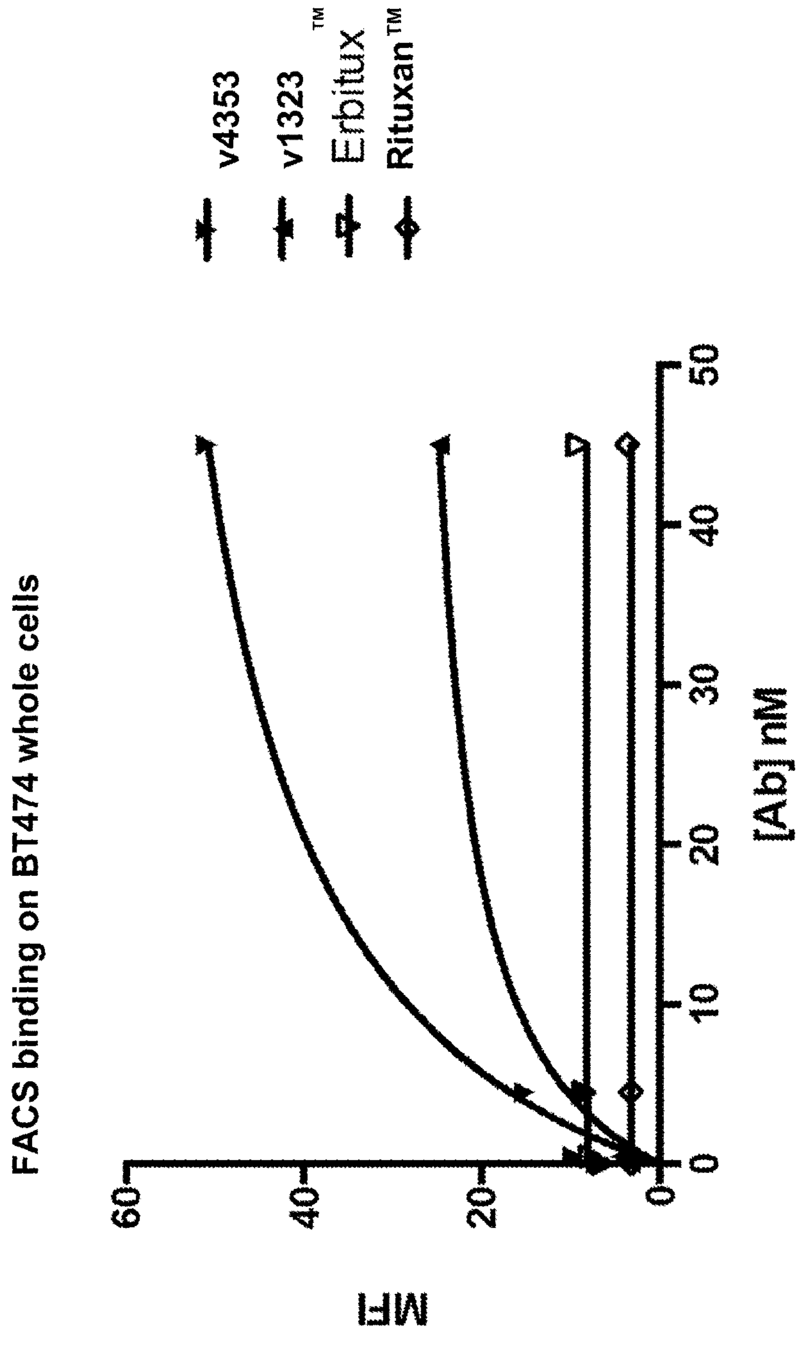
FIG. 3 depicts the ability of exemplary OA-EGFR antibodies to bind in a concentration-dependent and saturable manner to HER2 3+EGFR expressing breast cancer BT-474 cells. OA-EGFR antibodies show higher Bmax compared to Erbitux™, a full sized bivalent anti-EGFR antibody.

The results are shown in FIG. 3. Table 4A provides a summary of the cell binding data on BT-474.

TABLE 4A

| | Bmax (MFI) | $K_D$ (nM) |
|---|---|---|
| Erbitux | 8.2 | 0.0004 |
| OA-CTX | 65.5 | 13 |
| OA-EG2 | 29.2 | 8.2 |

The FACS binding results showed that the one armed antibodies displayed a higher Bmax than a corresponding bivalent antibody, towards saturating concentrations. OA-CTX displayed a higher Bmax than OA-EG2, which could be explained by different binding and dissociation kinetics to EGFR.

Example 5: Assessment of the Ability of Exemplary OA-EGFR Antibodies to Inhibit Growth of Cells EGFR-Expressing A431 Cells This experiment was performed to determine the ability of the exemplary OA-EGFR antibodies to inhibit the growth of an epidermoid carcinoma cell line (ATCC® CRL-1555) expressing high levels of EGFR. The growth inhibition assay was carried out as described below.

Five thousand A431 cells were seeded into each well of a 96-well plate. Antibodies OA-CTX v4353, OA-EG2 v1323 or Erbitux™ were added in triplicate to a final concentration of 300 nM, 30 nM, 3 nM and 0.3 nM. The final assay volume of the growth medium was 200 μL, and the 96-well plate was incubated 37° C. for 5 days. Media was removed from the plate, and 50 μL PBS was added to each well. Then, 50 μL of CellTiter-Glo® (Promega) reaction mixture was added to each well and the plate was incubated for 10 min. Finally, the RLU (relative light unit) values were read by a Pherastar plate reader. The percentage of cell growth relative to the untreated control was calculated by:

$$\% \text{ cell growth}=100\%\times(\text{RLUsample})/(\text{RLUuntreated})$$

Figure 4:
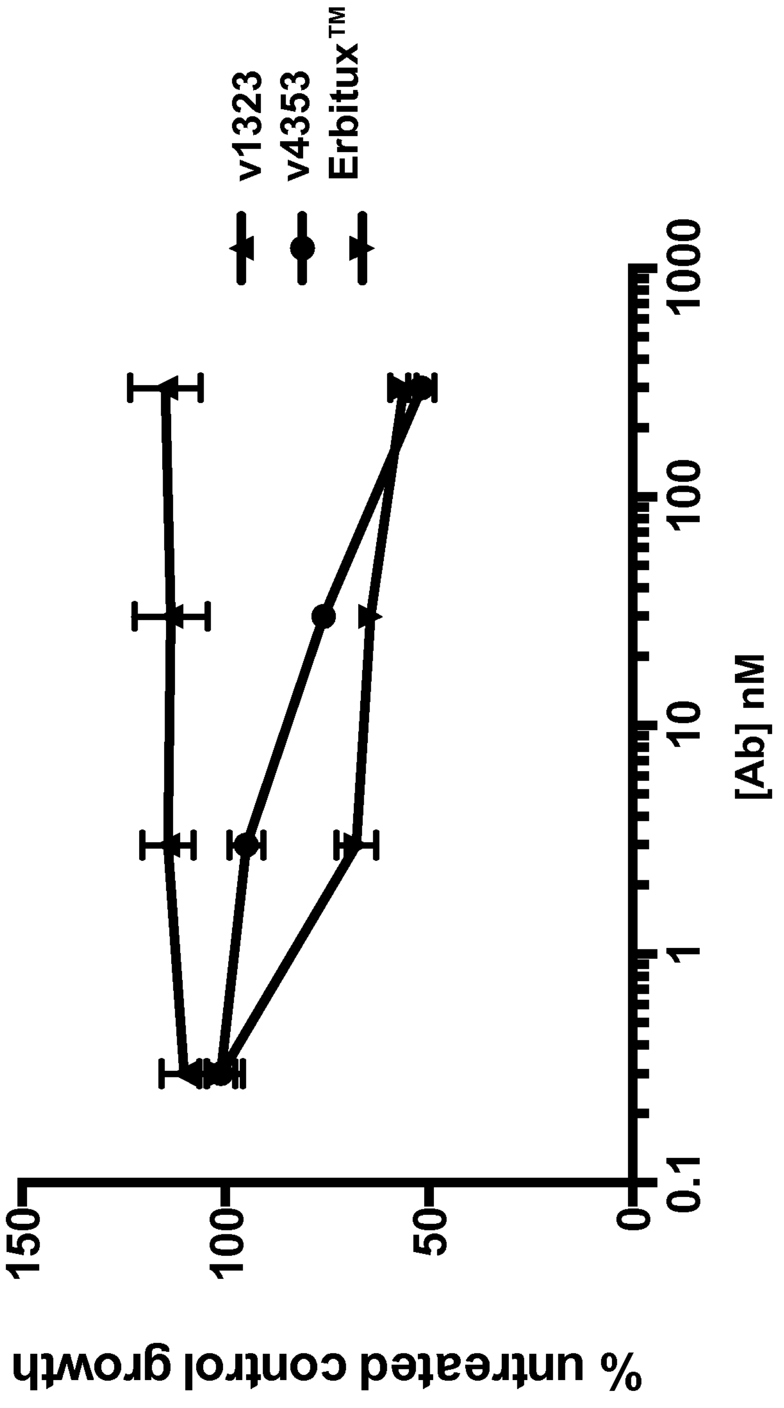
FIG. 4 depicts the ability of exemplary neutralizing and non-neutralizing OA-EGFR antibodies to inhibit the growth of A431 lung cancer cells expressing EGFR over a 5 day exposure, with inhibition seen with the neutralizing OA-EGFR v4353 but not the non-neutralizing OA-EGFR v1323.

The results are shown in FIG. 4. OA-CTX inhibited the growth of A431 as much as Erbitux™ at saturating conditions, whereas OA-EG2 did not inhibit the growth of A431. The inhibition of EGFR dependent growth in the high EGFR expressing A431 cells is consistent with OA-CTX's ability to neutralize EGF and OA-EG2's inability to neutralize EGF. The differential activity also reflects different abilities of OAAs (depending on the binding epitope) to block EGFR constitutive receptor signaling driving cell growth.

Example 6: Ability of Exemplary OA-EGFR Antibodies to Mediate ADCC

The ability of OA-EGFR antibodies to mediate ADCC in BT-474 a mammary ductal carcinoma-derived cell line was measured. The ADCC assay was carried out as described below.

The target BT-474 cells (10,000 cells, 50 μl) were added to each well of a 96-well plate, to which different concentrations of antibodies were added, distributed geometrically from 3 pM to 300 nM (final concentration). The plate was incubated for 30 min before PBMC effector cells were added to an effector cell to target cell (E: T) ratio of 25:1. The cells were gently mixed by cross shaking and the plate was further incubated at 37° C./5% $CO_2$ for 6 hr.

The percentage of cells lysed was determined by measuring the amount of LDH released into the supernatant using the LDH kit and Flexstation 3. The absorbance values at 492 nm were all background-subtracted with those at 650 nm. The calculation of the results was as shown below and the dose response curve parameters were fitted in Graphpad Prism:

$$\% \text{ cell lysis}=100\%\times(OD\text{sample}-OD\text{nonspecific})/(OD\text{max}-OD\text{min})$$

where: ODsample corresponds to the background subtracted value of the sample; ODnonspecific corresponds to the readout in the LDH assay when the target cells were incubated with the effector cells, without other treatment; ODmax corresponds to the maximum amount of target cell lysed. This readout was generated by adding 1% Triton X-100 to the target cells, incubated with antibody but without effector cells; ODmin corresponds to the minimum amount of target cell lysed. The target cells were incubated in the assay buffer without effector cells and antibody.

Figure 5:
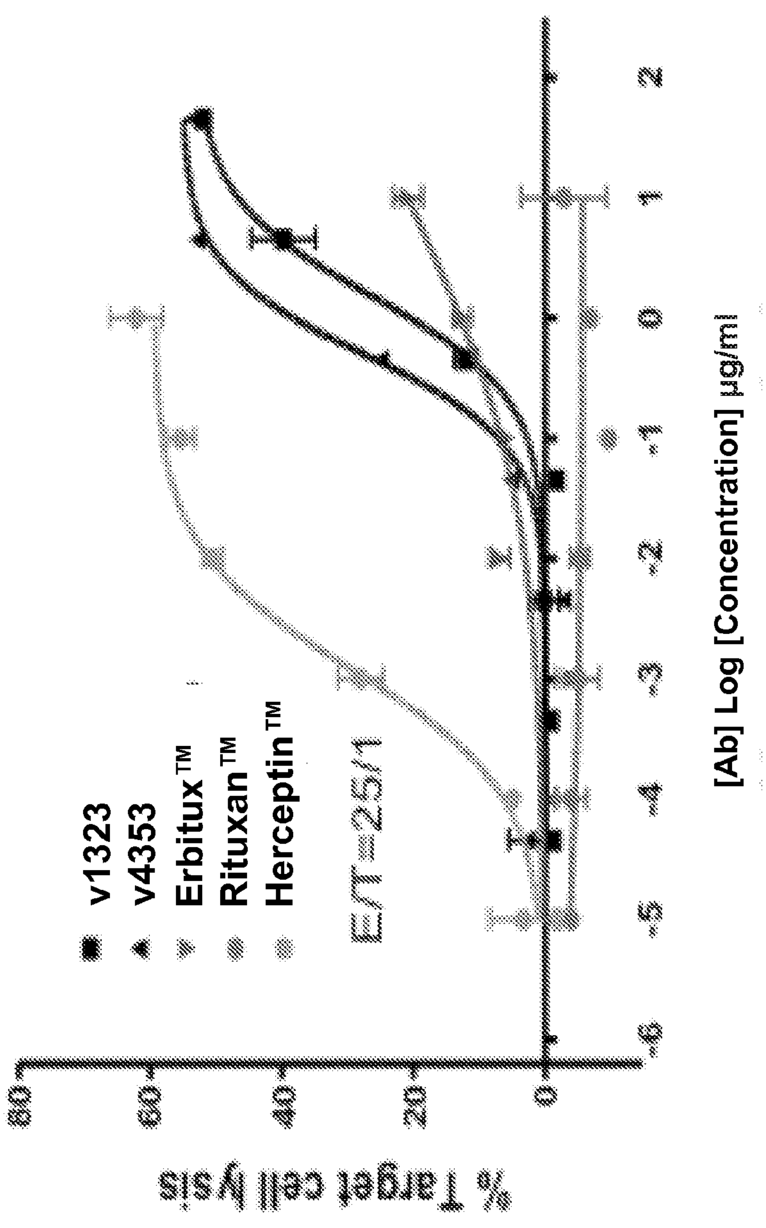
FIG. 5 depicts the ability of exemplary neutralizing and non-neutralizing OA-EGFR antibodies to mediate concentration dependent ADCC with an effector to target E:T ratio of 25:1 in breast BT-474 cancer cells.

The results are shown in FIG. 5. OA-CTX (v4353) and OA-EG2 (v1323) showed greater ADCC mediated cell lysis compared to Erbitux™.

Table 5 provides a summary of the dose response parameters of the ADCC lysis of BT-474 cells.

TABLE 5

| | Maximum cell lysis (%) | EC50 (nM) |
|---|---|---|
| Erbitux | 20* | n/a |
| OA-CTX v4353 | 55 | 5.2 |
| OA-EG2 v1323 | 52 | 22 |
| Herceptin | 59 | 0.008 |

*lysis at highest antibody concentration tested

Both exemplary OA-EGFR showed a higher percentage of target cell lysis compared to Erbitux™, with a difference of approximately 2-fold at the highest antibody concentration tested. This result was expected based on the increased level of cell surface decoration observed for the one armed antibodies over the corresponding full sized antibodies as shown in Example 4. Herceptin™ was also included as a positive control, and although BT-474 express 13-fold higher HER2 receptor level than EGFR, both OA-CTX v4353 and OA-EG2 v1323 were able to attain a similar level of maximum percentage ADCC lysis as Herceptin™. These results demonstrate that the one armed antibodies are able to achieve higher ADCC lysis not attainable by the corresponding full sized antibodies. This would likely be particularly important when the receptor level is not typically sufficient to induce efficient effector mediated cell killing. Additionally, the level of ADCC mediated by one armed antibodies can match that mediated by a full sized antibody targeting a different receptor that is expressed at a significantly higher level on the cell surface.

Example 7: Ability of an Exemplary OA-EGFR to be Internalized and to Downregulate Surface EGFR Expression The ability of v4353 to be internalized and to downregulate surface EGFR expression was measured in trastuzumab resistant breast cancer JIMT1 cells (expressing high levels of EGFR) cells.

This experiment was performed to determine whether an exemplary one armed anti-EGFR antibodies could be internalized in EGFR-expressing cells, as well as characterizing the properties of its combination with an anti-HER2 antibody. The direct internalization method was followed according to the protocol detailed in Schmidt, M. et al., Kinetics of anti-carcinoembryonic antigen antibody internalization: effects of affinity, bivalency, and stability. Cancer Immunol Immunother (2008) 57:1879-1890. Specifically, the antibodies were directly labeled using the AlexaFluor® 488 Protein Labeling Kit (Invitrogen, cat. no. A10235), according to the manufacturer's instructions.

For the internalization assay, 12 well plates were seeded with $1\times10^5$ cells/well and incubated overnight at 37° C./5% $CO_2$. The following day, the labeled antibodies were added at 200 nM in DMEM+10% FBS and incubated 24 hours at 37° C./5% $CO_2$. Under dark conditions, media was aspirated and wells were washed 2×500 µL PBS. To harvest cells, cell dissociation buffer was added (250 µL) at 37° C. Cells were pelleted and resuspended in 100 µL DMEM+10% FBS without or with anti-Alexa Fluor 488, rabbit IgG fraction (Molecular Probes, A11094, lot 1214711) at 50 µg/mL, and incubated on ice for 30 min. Prior to analysis 300 µL DMEM+10% FBS the samples filtered 4 µl propidium iodide was added. Samples were analyzed using the LSRII flow cytometer.

For the downregulation assay, the level of fluorescence of the antibodies were also measured for the cells incubated at 4° C.

The results of the internalization and downregulation experiment at 20 nM are shown in FIG. 6A. The results measured at 100 nM and 200 nM of the combinations are shown in FIG. 6B. For the combinations, the molecule that carries the fluorophore is marked by *. The measurement for 'surface 4 deg' of 1040+4353* was not available.

At 20 nM, OA-CTX (v4353) internalized to a similar extent compared to Erbitux and OA-CTX (v4353) downregulated surface EGFR but to a lesser extent than Erbitux.

At 100 nM, Erbitux™ did not potentiate the internalization of FSA-Tras (v506) nor HER2 downregulation.

At 200 nM, OA-CTX v4353+OA-Tras in combination, OA-CTX did not impact the internalization of OA-Tras nor HER2 receptor level induced by OA-Tras, and OA-Tras (v1040) appeared to slightly reduce the internalization of OA-CTX, but not the EGFR receptor level. OA-CTX v4353 downregulated surface EGFR to a lesser extent, as seen at 20 nM.

The extent of receptor downregulation and internalization were tested at different antibody concentrations. At 20 nM, 53% of EGFR remained on the surface when tested with OA-CTX v4353, but the Erbitux™ mediated a slightly higher level of receptor downregulation at 36%. However, both molecules were internalized to almost identical extents. Note also that a concentration dependence on receptor downregulation and internalization was observed when compared to OA-CTX tested at 200 nM.

At 100 nM, the impact of Erbitux™ on FSA-Tras internalization was tested, and the results showed that Erbitux™ did not impact the HER2 internalization and downregulation properties of FSA-Tras.

At 200 nM, the behavior of the one armed antibody combinations was investigated. Here, OA-CTX v4353 did not alter HER2 internalization and upregulation mediated by OA-Tras v1040, consistent with the observation for the full sized counterparts. However, OA-Tras appeared to slightly reduce the amount of internalization mediated by OA-CTX v4353, from 1300 MFI to 1050 MFI. It also appeared that the extent of EGFR downregulation was reduced in the combination.

The internalization profile of the exemplary one armed antibody indicates that it could be a suitable candidate for an antibody-drug conjugate (ADC).

Example 8: Anti-Tumor Activity of a Combination of OA-EGFR and OA-HER2 Antibodies in an SKOV3 Xenograft Model This experiment was carried out to determine if a combination of a OA-EGFR and OA-HER2 was able to decrease tumor volume or increase survival in a cell line-derived xenograft model.

A human ovarian cell line derived xenograft model, SKOV-3, was used to assess the antitumor efficacy of an anti-HER2 one armed antibody in combination with anti-EGFR one-armed monoclonal antibodies as single agents or in combinations to suppress tumor growth. Female Fox1n nude mice were inoculated with the tumor via the insertion of a 1 $mm^3$ tumor fragment in the subcutaneous tissue. Tumor measurements were taken biweekly until a volume of 200 $mm^3$ was reached; animals were then randomized into 3 treatment groups. The treatment groups were:
  Group (a) Non-specific hIgG control, dosed twice weekly
  Group (b) One Armed trastuzumab (OA-Tras; v1040), dosed twice weekly for 21 days, and then treatment was converted to One-Armed trastuzumab+One Armed pertuzumab (OA-Pert; v4182) on day 22
  Group (c) One-Armed trastuzumab+One-Armed cetuximab (OA-CTX; v4353), dosed twice weekly Treatment groups were dosed intravenously with a loading dose of 15 mg/kg on TO and maintenance doses of 10 mg/kg according to their dosing schedule for up to a total of 4 weeks. Tumor volume was evaluated by measuring tumor diameters biweekly during the treatment period and once a week during the follow-up period.

The serum concentrations on day 11 were determined for the test cohorts. For group b (OA-Tras), the mean serum concentration was 70.9 µg/ml (range of 35-95 µg/ml) and for group c (OA-Tras+OA-CTX), the mean serum concentration of total test antibodies was 165.6 µg/ml (range of 100-280 µg/ml).

Treatment of the SKOV-3 tumor bearing mice with group (c) most efficiently inhibited the growth of tumors compared to group a.

Figure 7:
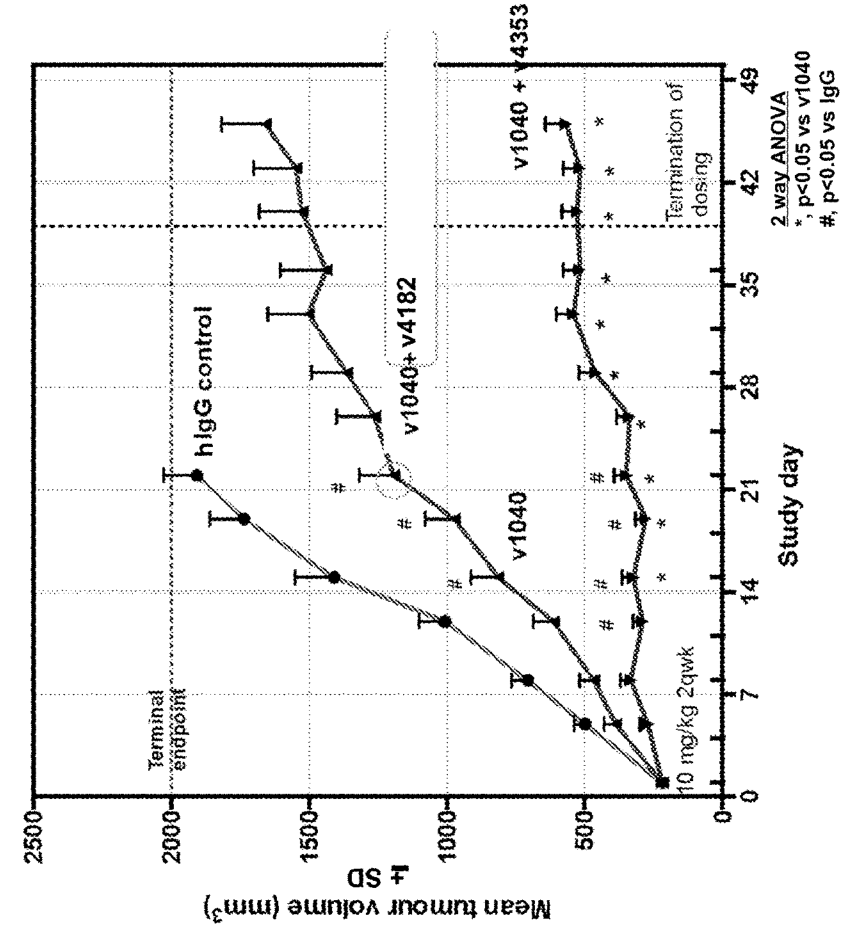
FIG. 7 depicts the ability of combinations of an exemplary OA-EGFR with an OA-HER2 antibody to inhibit growth of CTX-resistant established ovarian tumor SKOV3 in a mouse xenograft model.

The effect of the combination of OA antibodies on tumor volume is shown in FIG. 7.

Table 6 provides a summary of the in vivo tumour growth inhibition results at Day 22, in which drug conversion on selected cohorts occurred.

TABLE 6

| Day 22, n = 15 | Group (a) hIgG | Group (b) v1040 | Group (c) v1040 + v4353 |
|---|---|---|---|
| Mean TV ($mm^3$) | 1908 | 1194 | 349* |
| (% change from Baseline) | (+766%) | (+446%) | (+60%) |
| T/C (IgG) | 1 | 0.62 | 0.18 |
| Responders (TV <50% of IgG) | 0/15 | 7/15 | 15/15 |
| Complete response (>10% baseline regression) | 0/15 | 0/15 | 0/15 |
| RECIST assessment** | | | |
| Progressive disease (x > 20%) | 15/15 | 15/15 | 11/15 |
| Stable disease (−30% < x < 20%) | 0/15 | 0/15 | 4/15 |
| Partial response (−100% < x < −30%) | 0/15 | 0/15 | 0/15 |
| Complete response (x = −100%) | 0/15 | 0/15 | 0/15 |

*Similar mouse body weights across cohorts.
**x = % change in TV from baseline

Figure 8:
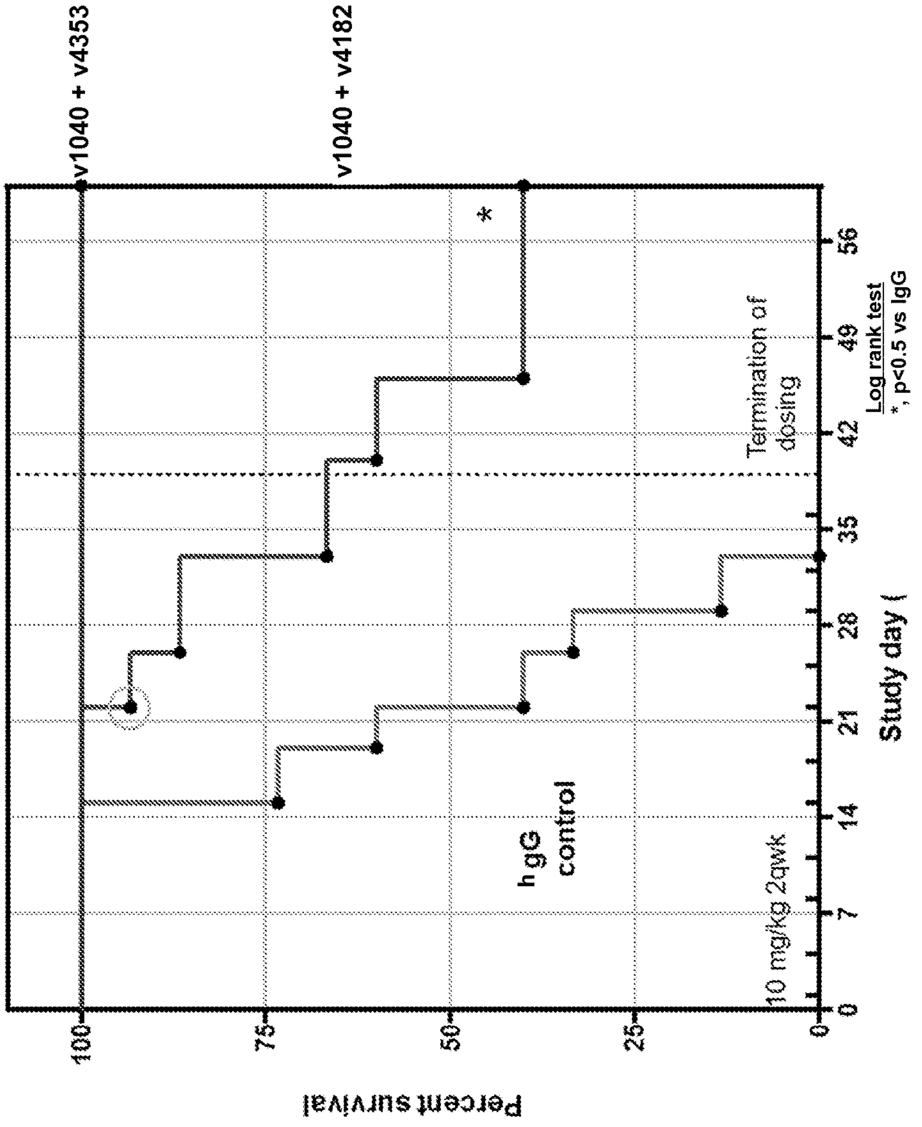
FIG. 8 depicts a Kaplan-Meier plot showing survival data for mice exposed to combinations of an exemplary OA-EGFR with an OA-HER2 antibody in the SKOV3 xenograft model of FIG. 7.

The results showing the effect of the combination of OA antibodies on survival rates are shown in FIG. 8.

In the SKOV3 mouse xenograft model, the OA-CTX+OA-Tras combination demonstrated the highest efficacy at inhibiting growth of established tumours. Statistical significance was established within 2 weeks of treatment with respect to the control and the other treatment groups (FIG. 7). Compared to OA-Tras, the addition of OA-CTX confers further tumour growth inhibition. An indirect comparison was made with the combination of two anti-HER2 one armed antibodies when the OA-Tras cohort was converted into a combination group by the addition of one armed pertuzumab, after which the tumour growth rate was not significantly reduced. The data suggests that tumour growth inhibition was more efficacious when treated by a combination of one-armed antibodies targeting different receptors. Based on the biological activity of the exemplary one armed antibodies observed in vitro in the same cancer cell line, it appears that the added efficacy arises from antibody mediated effector function from additional cell surface decoration.

The efficacy of the OA-CTX+OA-Tras was also apparent from the Kaplan-Meier plot (FIG. 8) in which a tumour volume of 2000 $mm^3$ was used as the terminal endpoint serving as surrogate readout for survival. As shown in FIG. 8, no mice in the hIgG control group survived past day 33 after treatment. In comparison, the survival of mice in the OA-Tras/+OA-Pert group was reduced to less than 33% on day 60. In the OA-CTX+OA-Tras group, however, all of the animals remained alive, further demonstrating the efficacy of the one armed antibody combination.

Overall, the exemplary combination of OAA has demonstrated superior tumour growth inhibition properties in vivo compared to controls. All tumours in the OAA combination cohort responded to the treatment, according to our internal criteria. Additionally, the OAA combination reduces the number of progressive diseases as well as at least a 2.3-fold delay in the mean time to progression compared to controls, according to the RECIST assessment of solid tumour growth.

Table 7 provides a summary of the results shown in the Kaplan-Meier plot (FIG. 8).

TABLE 7

| Terminations due to TV >2000 $mm^3$ (n = 15) | Group (a) hIgG v6908 | Group (b) OA-Tras v1040 (+OA-Pert v4182) | Group (c) OA-CTX v4353 + OA-Tras v1040 |
|---|---|---|---|
| Study day 22 | 9 | 1 | 0 |
| Study day 26 | 10 | 2 | 0 |
| Study day 29 | 13 | 2 | 0 |
| Study day 33 | 15 | 5 | 0 |
| Study day 46 | 15 | 9 | 0 |
| Median survival (days) | 22 | 46 | undefined |

Table 8 provides a summary of results on tumour growth kinetics.

TABLE 8

| Tumour growth Kinetics | hIgG | v1040 OA-Tras | v1040 + v4353 OA-Tras + OA-CTX |
|---|---|---|---|
| Mean Tumour Doubling Time (days) | 5.6 (n = 15) | 9.6 (n = 15) | 29* (n = 11) |

TABLE 8-continued

| Tumour growth Kinetics | hIgG | v1040 OA-Tras | v1040 + v4353 OA-Tras + OA-CTX |
|---|---|---|---|
| Mean time to progression by RECIST assessment (days) | <5 (n = 15) | <5.2 (n = 15) | >11.7 (n = 15)** |
| Mean TGD to 1000 $mm^3$ (days) | 12 | 22 | undefined |

**tumours identified as stable disease were assigned t = 22 days as the time limit for onset of progression for calculation purpose

Example 9: Transient CHO Expression, Purification and Yield of Afucosylated Exemplary Antibodies Afucosylated antibodies are known to enhance ADCC and other antibody effector functions. An afucosylated exemplary antibody (OA-CTX-afuco, v7192) was produced using the same transient CHO expression system and protein A and size exclusion chromatography purification procedure as described Example 2, with the addition of an extra clone encoding a GDP-6-deoxy-D-lyxo-4-hexulose reductase (RMD) from *Pseudomonas aeruginosa* PAO1 to 15% of the total DNA transfected (von Horsten et al Glycobiology (2010) 20 (12): 1607-1618), i.e. the final DNA ratios of HC:Fc:LC:RMD was 30.6:20.4:34:15.

Figure 9A:
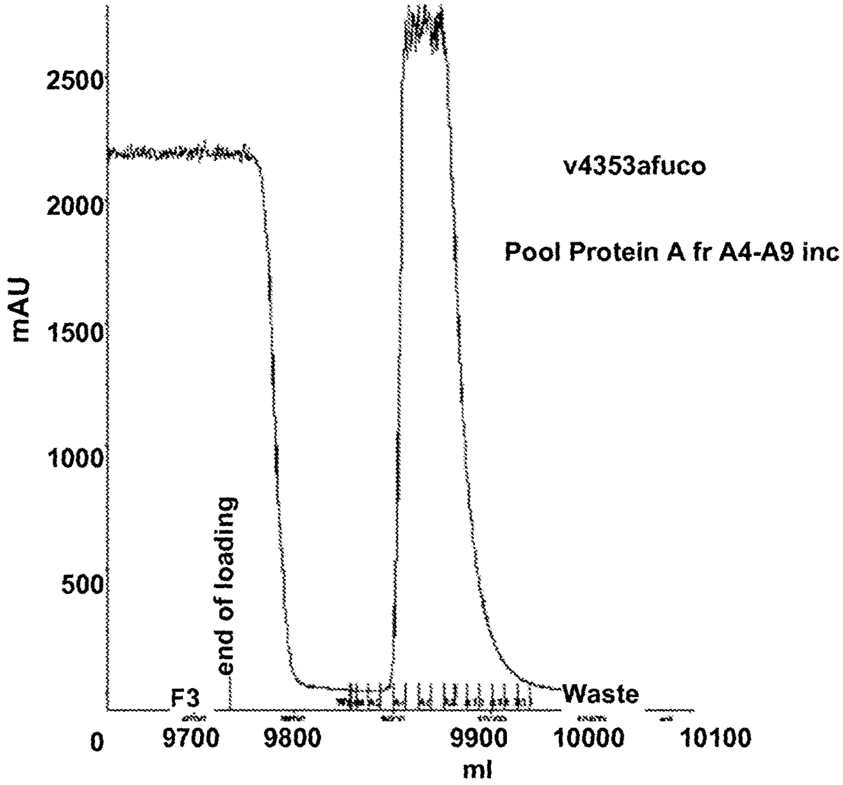
FIG. 9 shows the UPLC-SEC chromatogram of an exemplary afucosylated OA-EGFR v4353 (v7192) antibody following protein A and SEC purification.
Figure 9B:
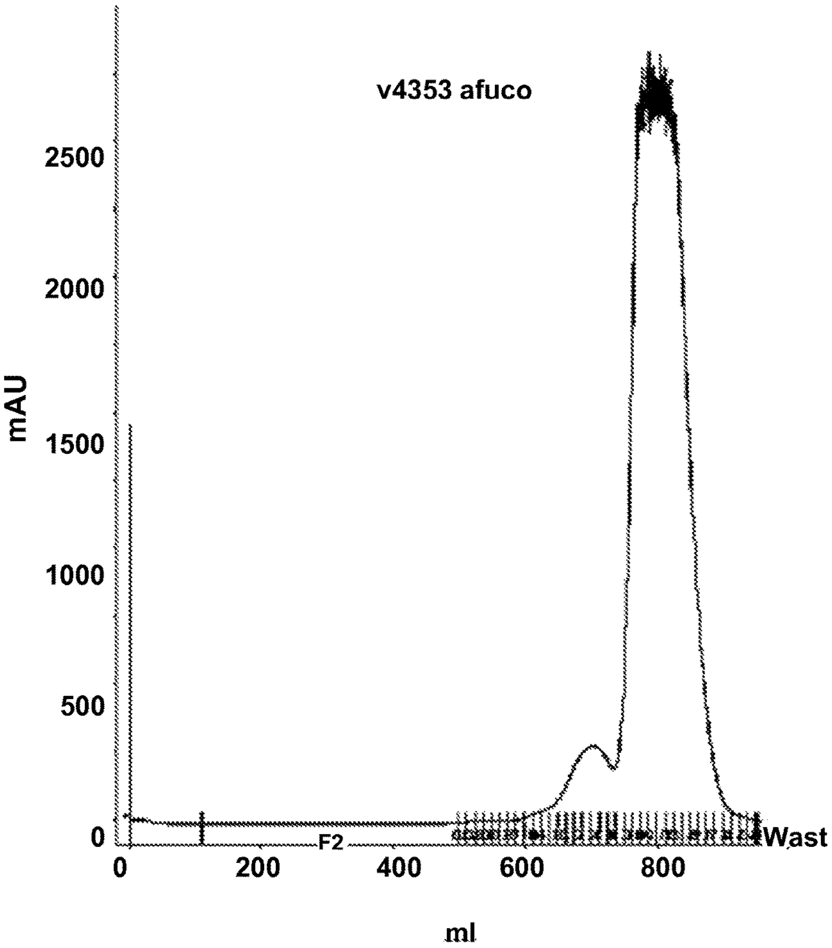

The afucosylated exemplary antibody was expressed in a 10 L culture. After protein A purification (FIG. 9A), 1 g of protein was recovered. Upon further purification by size exclusion chromatography using the Superdex 200 column (FIG. 9B), 975 mg of protein was recovered.

Figure 10A:
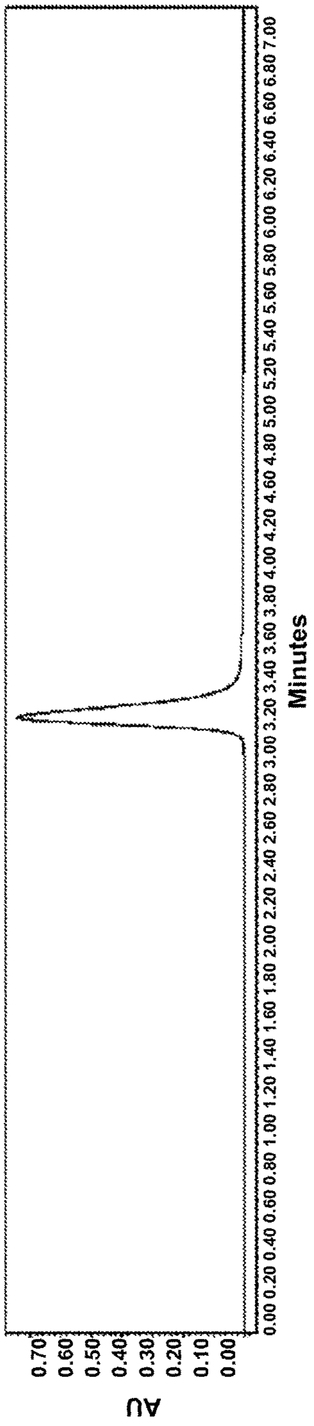
FIG. 10 shows the UPLC-SEC chromatogram (FIGS. 10A and 10B).
Figure 10B:
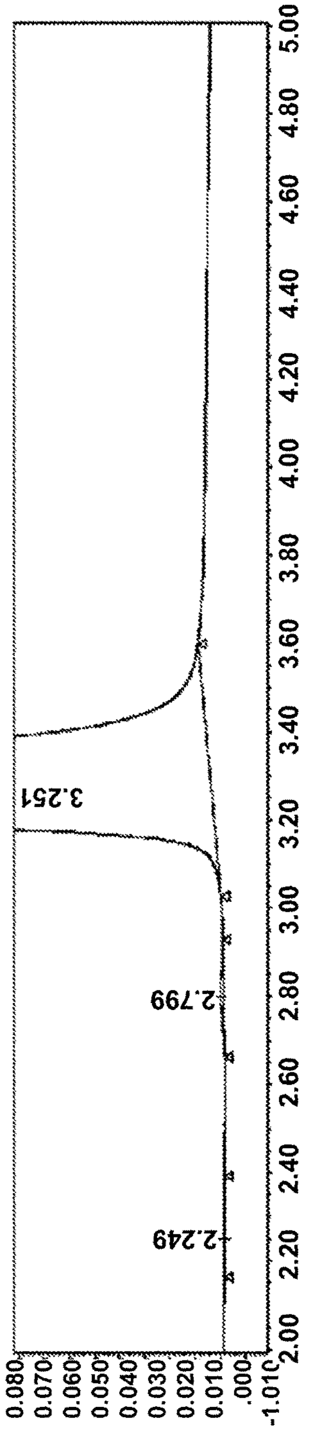

The endotoxin level was less than 0.001 EU/mg. The purity, as assessed by UPLC-SEC, was 99.81%. FIGS. 10A and 10B show the UPLC-SEC chromatograms of purified v7192.

In brief, the glycan analysis of the antibody was performed by first reducing the sample using 10 mM dithiothreitol (DTT) at 56° C. for 1 hr, alkylation with 55 mM iodoacetamide at room temperature for 1 hr, and then digestion with trypsin in 50 mM ammonium bicarbonate at 37° C. overnight. The digested sample was analyzed on the nanoLC-MS/MS on the Q-Tof Ultimate MS. The NCBI database was searched with Mascot to identify proteins sequences. MaxEnt3 (MassLynx) was used to deconvolute the glycopeptide ions and to quantify the relative abundance of different glycoforms.

No significant fucosylation was detected in the exemplary antibody by LC-MS (>98% afucosylated). FIG. 11 shows the glycan analysis of the tryptic digest of the exemplary afucosylated antibody v7192-afuco by LC-MS.

These results show that the exemplary OAA antibody can be produced in large scale as an afucosylated antibody, and purified to very high purity using standard procedures.

Table 9 is summarizes the purity and yield of the afucosylated exemplary antibody.

TABLE 9

| Variant | post protein A conc. (mg/ml) | post protein A yield (mg) | post SEC conc. (mg/ml) | post SEC yield (mg) |
|---|---|---|---|---|
| v7192 | 15.03 | 1022 | 7.8 | 975 |

Example 10: Conjugation of the Exemplary Antibodies to a Toxic Drug Payload to Generate an ADC Exemplary OA-CTX-afuco v7192 was conjugated to mertansine (DM1) to form an antibody-drug conjugate (ADC, v7104) using a one-step procedure.

Conjugation was performed as follows. The starting protein sample was first exchanged into a buffer composed of 50 mM potassium phosphate pH 6.5, 50 mM NaCl and 2 mM EDTA using a PD-10 column, and adjusted to a protein concentration of 10 mg/ml. A 10 mM solution of SMCC-DM1 (prepared in house) dissolved in dimethylacetamide (DMA) was then added to 7.5 molar equivalents of the protein sample. DMA was further added to a final concentration of 10% v/v and the sample was mixed briefly. The reaction mixture was incubated at 25° C. overnight with mixing. The progress of the reaction, determined by the content of unconjugated protein sample, was monitored by hydrophobic interaction chromatography-high performance liquid chromatography (HIC-HPLC). This was performed using the Tosoh TSK gel Butyl-NPR column (4.6 mm×3.5 mm×2.5 mm). Elution was performed at 1 ml/min using a gradient of 10-90% buffer B over 25 min followed by 100% buffer B for 4 min. Buffer A comprises 20 mM sodium phosphate, 1.5 M ammonium sulphate, pH 7.0. Buffer B comprises 20 mM sodium phosphate, 25% v/v isopropanol, pH 7.0. SMCC-DM1 was added in small increments until the amount of unconjugated protein was less than 5%. The product was then exchanged into a buffer composed of 20 mM sodium succinate pH 5.0 using a PD-10 column, and the protein concentration and drug-to-antibody ratio (DAR) were calculated based on the absorbance at 252 and 280 nm. The buffer was adjusted to a final composition of 20 mM sodium succinate, 6% w/v trehalose and 0.02% w/v polysorbate 20, pH 5.0. High performance liquid chromatography-size exclusion chromatography (HPLC-SEC) was performed to determine the purity of the ADC, using the Tosoh G3000-SWXL column (7.8 mm×30 cm), in 100 mM sodium phosphate, 300 mM sodium chloride, pH 7.0, at a flow rate of 1 ml/min.

Figure 12:
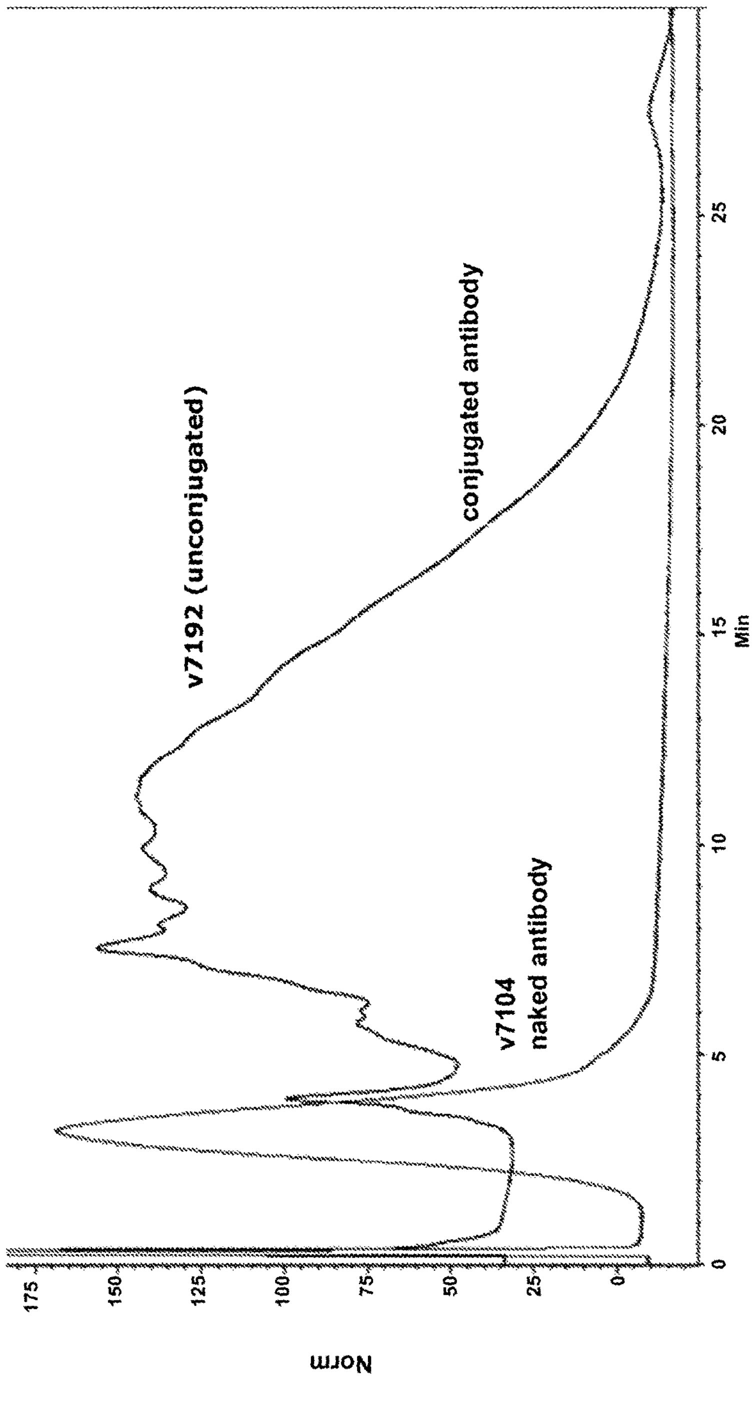
FIG. 12 shows the overlay of the HIC-HPLC chromatogram of the unconjugated v7104 and DM1-conjugated v7192 exemplary OA-EGFR antibodies.
Figure 13:
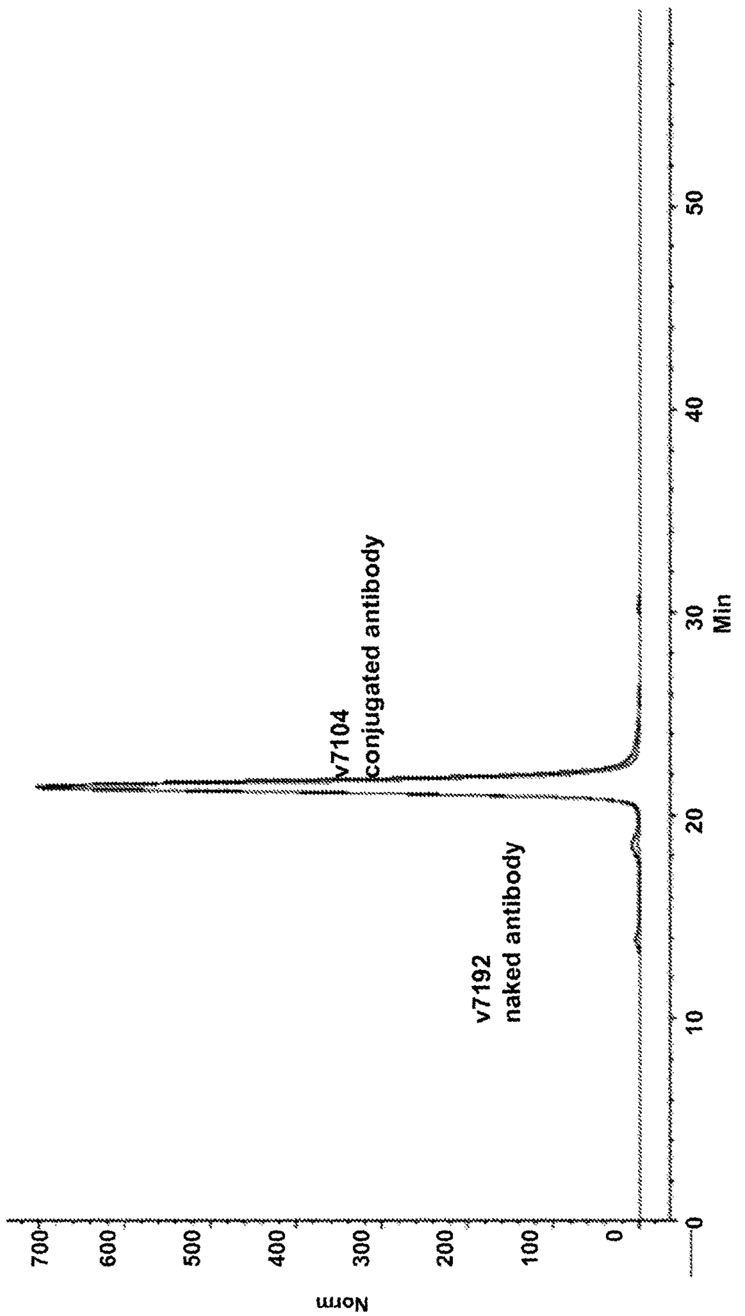
FIG. 13 shows the overlay of the HPLC-SEC chromatogram of the unconjugated v 7104 and conjugated v7192 exemplary OA-EGFR antibodies.

Conjugation was performed on 234 mg of afucosylated exemplary antibody, to yield an ADC of 98% purity and a DAR of 3.09. There was 3.63% of unconjugated antibody and 4.81% of high molecular weight (HMW) contaminant. The recovery was 73% and the endotoxin level was <0.25 EU/mg. FIG. 12 shows the overlay of the HIC-HPLC chromatogram of the unconjugated OA-CTX-afuco v7192 and the conjugated OA-CTX-afuco v7104. The delayed elution profile of v7192 was expected based on the increased hydrophobicity of the ADC as a result of chemical conjugation to SMCC-DM1. The breadth of the v7192 chromatogram is also consistent with the conjugation of SMCC-DM1 to a random number (typically between 0-10) of accessible lysine residues on the antibody. FIG. 13 shows the SEC-HPLC chromatogram of exemplary unconjugated afucosylated OA-CTX v7192 and the conjugated afucosylated OA-CTX v7104. The close superposition of the chromatogram shows that the overall structural integrity of the antibody is retained, and the exemplary OA-CTX-afuco is amenable to standard conjugation procedure without forming any undesired HMW contaminant.

These results show that the exemplary antibody is amenable to standard large scale conjugation procedures.

Example 11: Exemplary OA-EGFR Binds Cells with a Higher Bmax than the Corresponding Bivalent Antibody Whole cell binding assays were performed to compare the level of binding between the exemplary OA-EGFR and the corresponding bivalent antibody, on human tumour cells expressing different levels of target antigen EGFR (see Table AA for cell lines).

Flow cytometry was performed as described in Example 4, with the modification that the incubation of primary antibody was for 2 hr. Also, AF488 anti-human IgG (Fc specific) antibody (Jackson Immunochemicals) was used as secondary antibody for detection instead.

In all human tumour cell lines tested, the exemplary OA-CTX v4353 showed approximately a 1.38-1.68 fold higher Bmax than the corresponding bivalent antibody depending on the cell line tested. Additionally, the Bmax for the combination of OA-CTX+OA-Tras v1040 was higher than each of the individual OAAs by themselves, and is approximately equal to the sum of their individual Bmax's.

Figure 14:
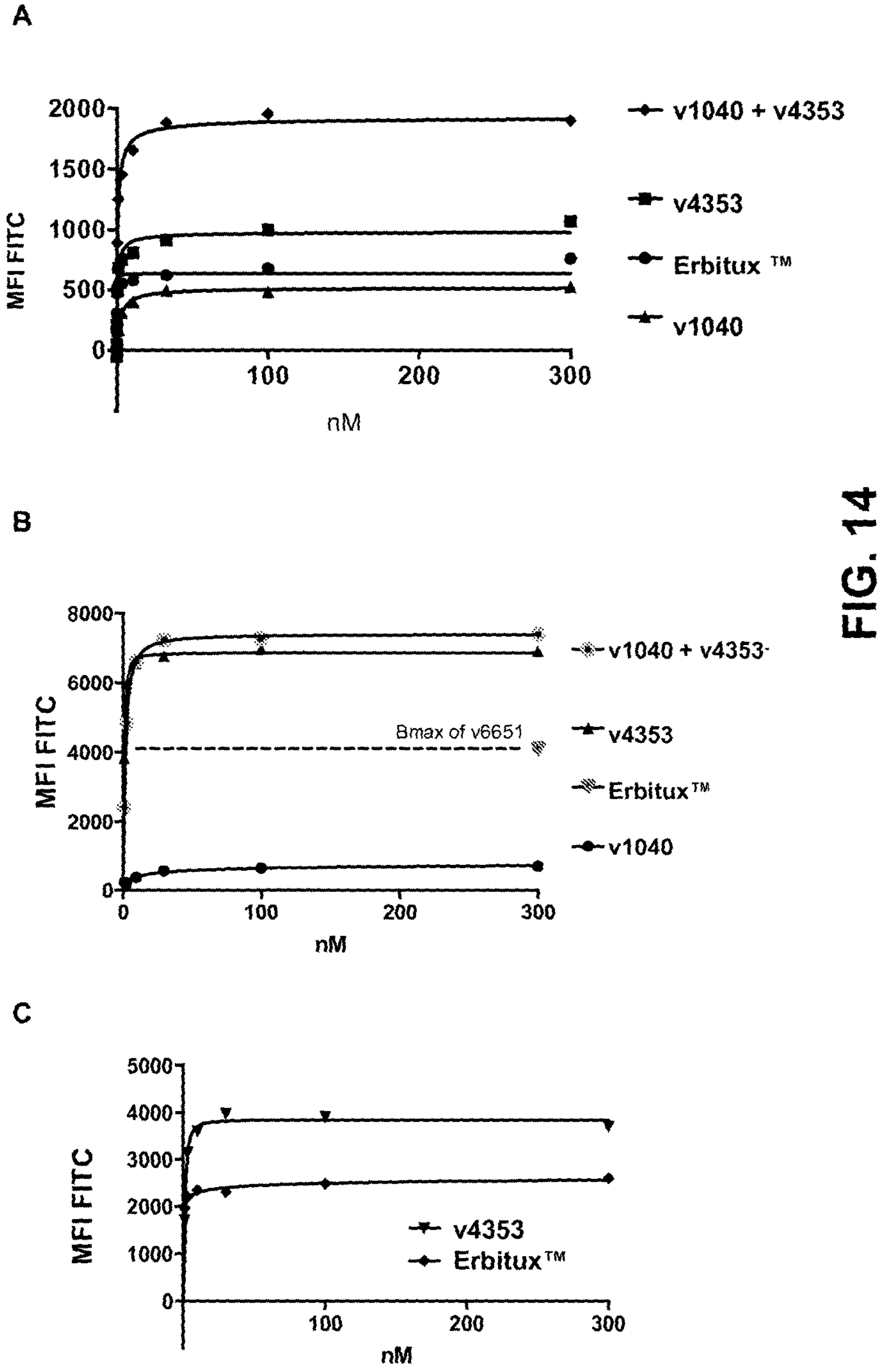
FIG. 14 shows the whole cell saturation binding on various human tumour cell lines. The Bmax fold increase of OA-EGFR compared to the corresponding bivalent antibody was 1.55, 1.68 and 1.38 in colorectal HCT116 (FIG. 14A), triple negative breast cancer (TNBC) MDA-MB-231 (FIG. 14 B) and ovarian SKOV3 (FIG. 14 C) respectively.

FIGS. 14A, 14B and 14C show the results of whole cell binding experiments on colorectal HCT116, breast MDA-MB-231 and ovarian SKOV3 cell lines.

The FACS binding results show that the exemplary OA-EGFR can bind human tumor cells to a higher level than the corresponding bivalent antibody in that more antibody molecules are bound to the cells. The level of cell binding can be further increased by using a combination of antibodies that do not compete for the same binding site.

Example 12: Ability of Exemplary OAAs to Mediate ADCC in Human Colorectal Cancer Cells Caco2

The ability of exemplary anti-EGFR OAAs to mediate ADCC in a different EGFR expressing cell, the human colorectal cancer cell line Caco2, was compared with that of a full size bivalent anti-EGFR antibody.

The ADCC assay was performed as described in Example 6, except that the PBMC E:T ratio was 50:1.

Both exemplary anti-EGFR OAAs v4353 and v1323 displayed slightly higher % target cell lysis (i.e. higher efficacy) than the bivalent Erbitux™ at 300 nM antibody concentration. There is however a large difference in EC50; the considerably lower potency of the exemplary v1323 is consistent with its relatively high dissociation rate from the cell surface EGFR. Nevertheless, the combination of v1040 (one armed anti-HER2 antibody) with v1323 results in slightly higher % target cell lysis at near-saturating concentrations. FIGS. 15A and 15B show the ADCC dose response curves of exemplary OAAs on Caco2 cells.

These results demonstrated that anti-EGFR OAAs mediate higher ADCC efficacy compared to bivalent anti-EGFR antibodies. The combination of antibodies binding different epitopes also leads to higher ADCC efficacy. This is consistent with the increased level of antibody binding the target cells. However, the relative increase between cell binding and ADCC efficacy appears to vary depending on the relevant receptor expression level of the target cells.

Example 13: Exemplary OAAs Show Higher ADCC Efficacy than the Corresponding Bivalent Antibody Afucosylation of antibodies is known to enhance effector function. The exemplary afucosylated OA-CTX-afuco v7192 was tested against the non-afucosylated counterpart v4353 in an ADCC assay on MDA-MB-231 (EGFR mid/high) to assess changes in efficacy and potency as a result of afucosylation.

Figure 16:
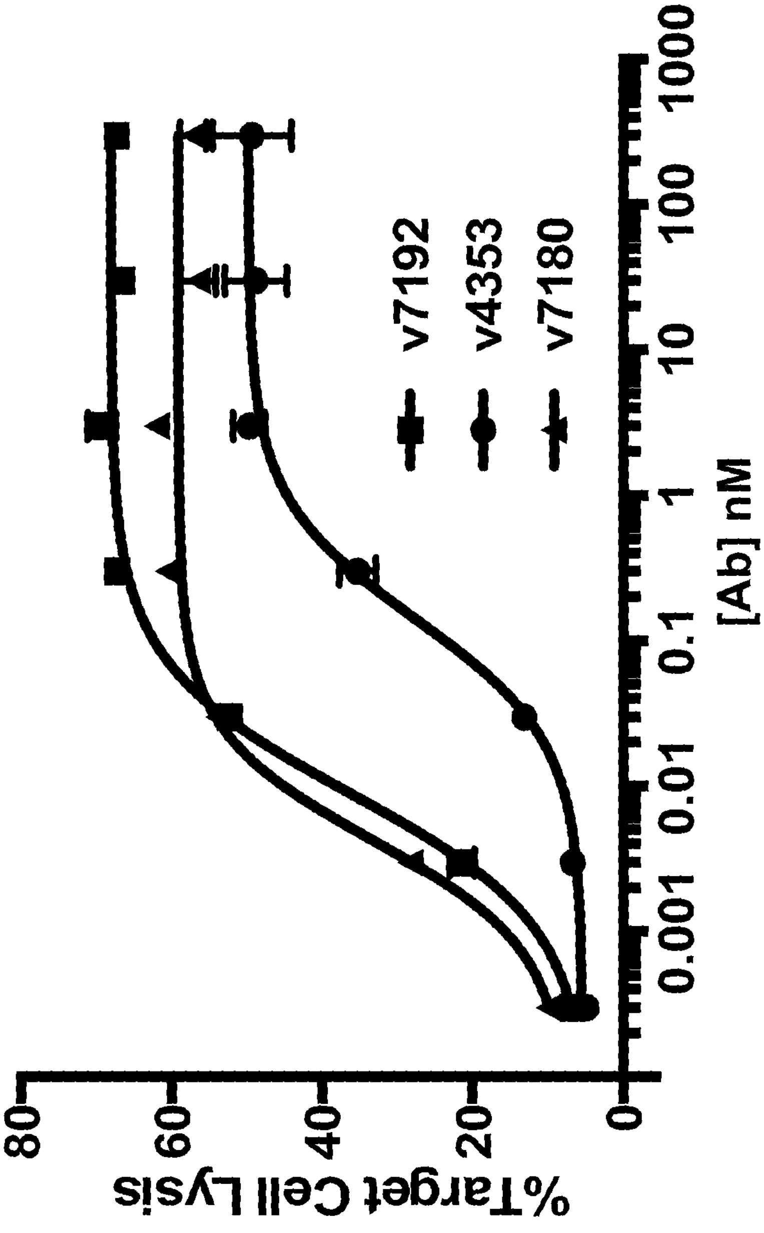
FIG. 16 shows the ADCC dose response curves of the afucosylated (v7192) and non-afucosylated (v4353) exemplary OA-EGFR on TNBC MDA-MB-231 cells assessed at a NK92 (CD16a: 158V/V) effector to target TNBC MDA-MB-231 E:T ratio of 5:1.

The ADCC assay was performed as described in Example 6, except that NK92/CD16a(158V/V) cells (generated by Genscript) were used as effector cells, at an E:T ratio of 5:1. The results are shown in FIG. 16.

The afucosylated exemplary OAA v7192 showed higher efficacy than the non-afucosylated counterpart v4353 (62% vs. 45% target cell lysis). The afucosylated antibody was also much more potent, with an EC50 of 9 pM, which was approximately 16-fold lower than the EC50 of the corresponding non-afucosylated OAA.

The afucosylated OAA v7192 also showed a slightly higher % target cell lysis compared to Erbitux™, (v7180) although they displayed similar potency.

These results demonstrated that afucosylation of the exemplary OAA can result in an enhanced efficacy and potency in effector mediated functions such as ADCC.

Example 14: Exemplary OA-ADC Inhibited Growth of Human Triple Negative Breast Cancer Cell Line MDA-MB-231

The potency and efficacy of the exemplary OA-CTX-afuco-ADC v7104 on the human triple negative breast cancer cell line MDA-MB-231 (EGFR mid/high, HER2 low, KRAS G13D mutant) was determined using an in vitro growth inhibition assay.

In brief, 2,000 MDA-MB-231 cells were seeded into 96-well plates and incubated for 24 hr at 37° C., 5% $CO_2$ in RPMI supplemented with 10% FBS. Then, antibodies were added in triplicate, starting from a final concentration of 30 nM which was serially diluted 3-fold down to 0.00457 nM. The cells were further incubated for 5 days. Cell growth was measured using the Sulforhodamine B (Sigma) assay following the manufacturer's recommended protocol. The untreated control cells grew approximately 6-fold over the course of the experiment.

Figure 17:
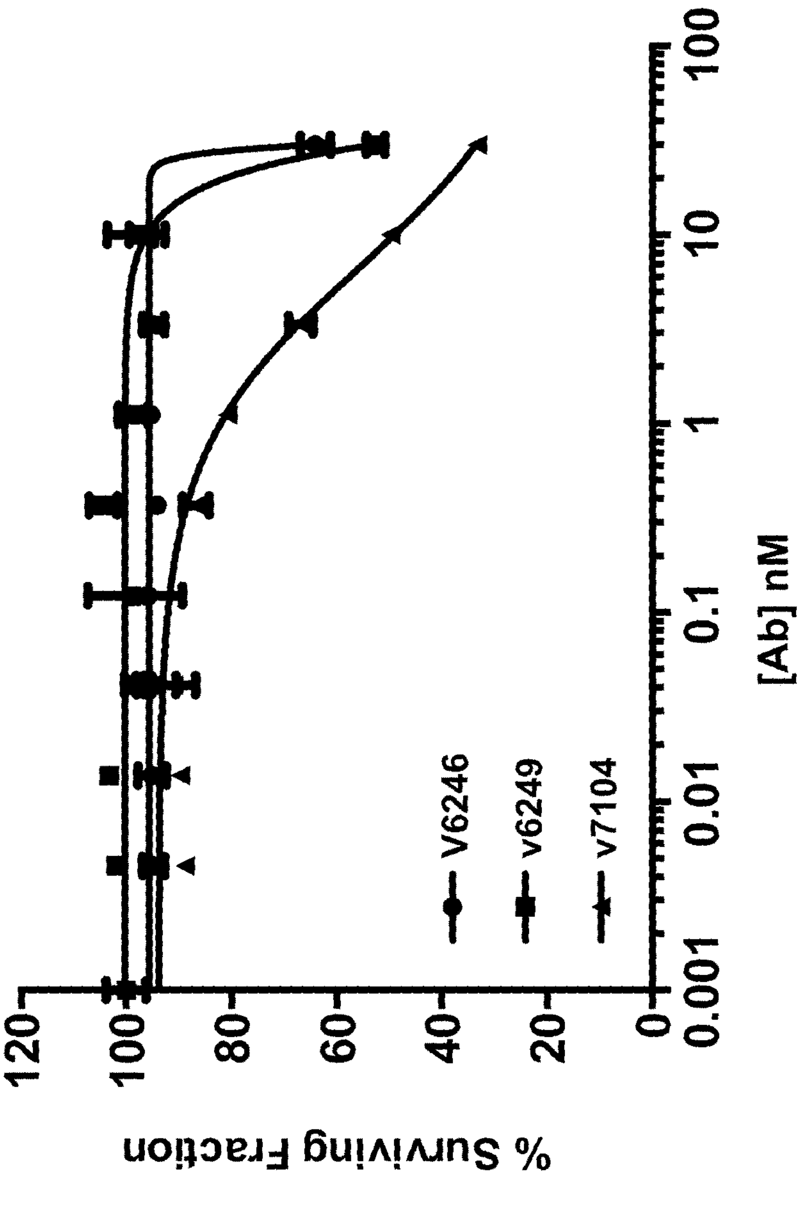
FIG. 17 shows the growth inhibition dose response curve of the exemplary OAADC on a human triple negative breast cancer cell line MDA-MB-231.
Figure 19:
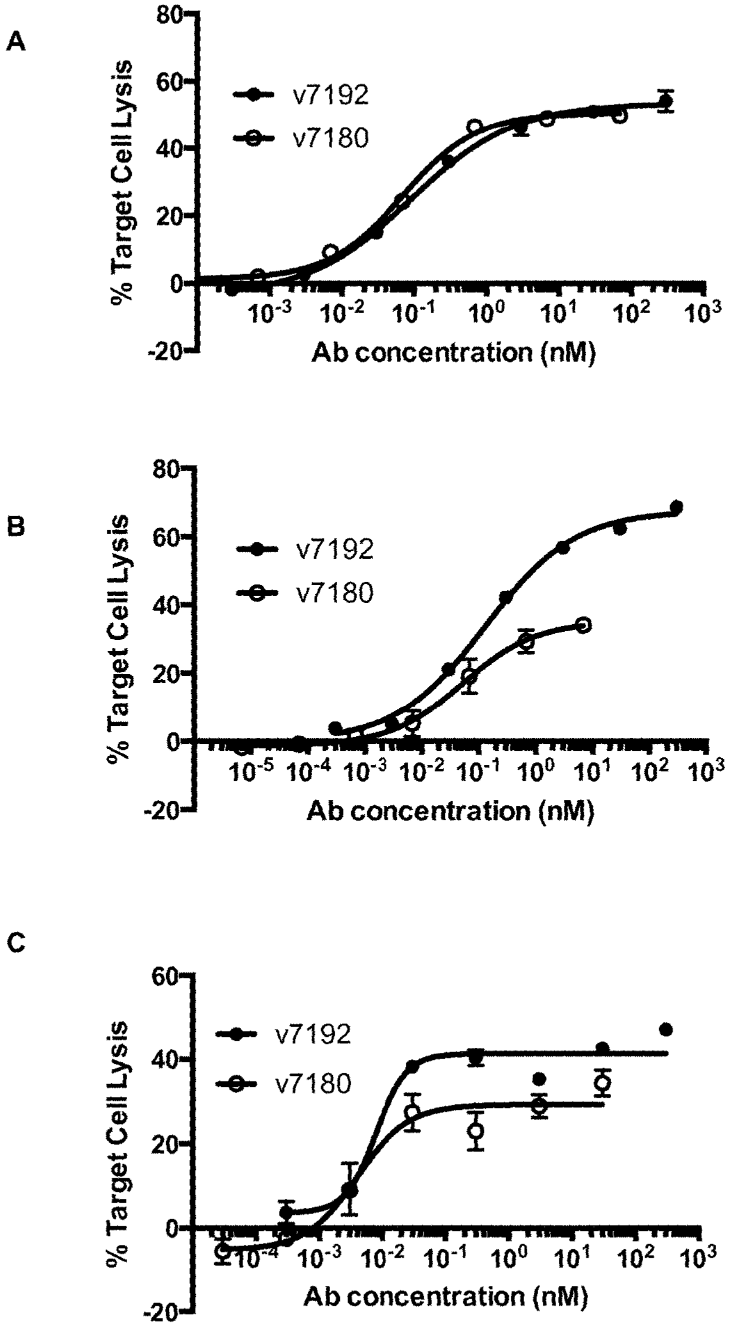
FIG. 19 shows the ADCC dose response curves of the afucosylated (v7192) exemplary OA-EGFR and Erbitux™ (v7180) on A431 cells A549 cells and HCT116 cells, which express on their cell surfaces high, medium and low levels of EGFR respectively.

The results in FIG. 17 show that the exemplary OA-CTX-afuco-ADC v7104 displayed significant growth inhibition (up to 50%) compared to the negative control v6249 (IgG-ADC), which showed no significant growth inhibition at up to 10 nM. At 30 nM, non-specific activity was observed for the control, but the exemplary OA-CTX-afuco-ADC exhibited higher growth inhibition levels of approximately 67%. Higher antibody concentrations were not tested. The EC50 of v7104 is estimated to be 3-10 nM whereas that of v6249 is approximately 30 nM.

T-DM1 (v6246, Trastuzumab emtansine produced in house) was also tested as another control, but it displayed the same dose response profile as the negative control v6249. This is not surprising considering the very low HER2 expression status on MDA-MB-231.

These results demonstrated that the exemplary OA-CTX-afuco-ADC is potent and efficacious against the EGFR expressing human triple negative breast cancer cell line MDA-MB-231. The results are consistent with the ability of the anti-EGFR OAA to become internalized by target cancer cells. Additionally, the OA-CTX-afuco-ADC demonstrated efficacy in a cell line with a KRAS G13D mutation, which is known to confer resistance to conventional anti-EGFR treatments such as cetuximab.

Example 15: Exemplary OAA Growth Inhibited Keratinocytes with Reduced Potency Skin rash is a side effect frequently observed among patients treated with EGFR inhibitors including anti-EGFR antibodies such as cetuximab. The direct toxicity of EGFR inhibitors on keratinocytes is believed to be one of the mechanisms that causes skin rash. The potential skin toxicity of exemplary anti-EGFR OAAs was assessed using a growth inhibition assay on HACAT keratinocytes (EGFR medium-expressors).

The growth inhibition assay was performed as described in Example 5. In brief, 5,000 or 10,000 HACAT cells were seeded into each well. After an overnight incubation, the cells were treated with antibodies and incubated at 37° C., 5% $CO_2$ for 3 or 5 days. The level of growth was determined using the CellTiter 96® AQueous Non-Radioactive Cell Proliferation Assay (MTS) kit (Promega). OA-CTX v4353 and OA-CTX-afuco v7192 were tested in the presence of 10% FBS and OA-EG2 v1323 was tested in the absence of FBS. The results are shown in FIGS. 18A and 18B.

The exemplary antibody OA-CTX v4353 showed similar growth inhibition properties to Erbitux™ at the highest concentration (300 nM) of antibody tested. However, OA-CTX showed a much reduced potency compared to Erbitux™ as evidenced by much less cell growth inhibition at lower antibody concentrations. The OA-CTX-afuco showed a dose response similar to that of OA-CTX.

In comparison, OA-EG2 showed no significant growth inhibition at the concentrations tested. This is consistent with EG2 being an antibody that does not neutralize EGFR.

The results indicate that the exemplary OA-CTX antibody has lower toxicity against skin cells than the corresponding bivalent antibody.

Example 416: ADCC Activity of Exemplary OAA in Human Cancer Cells Expressing Different EGFR Levels Additional human cancer cell lines expressing different levels of EGFR were further tested to demonstrate the superior ADCC activity of the monovalent anti-EGFR OAA over the bivalent counterpart.

The relative level of EGFR expression and antibody binding (at 300 nM) on the cancer cell lines were performed as described in Example 11, using Alexa Fluor 488-conjugated AffiniPure Fab Fragment Goat Anti-Human IgG(H+L) as secondary antibody.

The ADCC assay was performed as described in Example 6. A431 and A549 cells ADCC employed NK92/FcγR3a (158V/V) cells while HCT116 cells employed PMBC pre-stimulated overnight by IL2.

TABLE 14.1

Relative EGFR level on human cancer cell lines represented as median fluorescent intensity (MFI) values.

| Cell line | v4353 | v7192 | v7180 | EGFR level designation |
|---|---|---|---|---|
| A431 | 2300 | 2200 | 1700 | high (3+) |
| A549 | 200 | 200 | 130 | medium (2+) |
| HCT116 | 39 | 30 | 10 | low (1+) |

The relative EGFR expression of the 3 additional human cancer cell lines was determined. As shown in the table above, a high, medium and low EGFR expressing cell line was tested. These qualitative terms are assigned based on the literature reported EGFR level of A431, which is in the order of millions of receptor molecules per cell, and is being considered as a high level of receptor expression.

In the high EGFR expressing A431 epidermoid cancer cells, the ADCC potency (EC50 of 0.09 nM vs 0.07 nM) and efficacy (53% vs 51%) between the exemplary v7192 and the control v7180 were very similar.

In the medium EGFR expressing A549 lung cancer cells, v7192 showed a similar potency to v7180 (EC50 of 0.13 nM vs 0.052 nM), but a 1.9-fold enhancement in ADCC efficacy (68% vs 35%).

Similarly, in the low EGFR expressing HCT116 colorectal cancer cells, the potency between the monovalent v7192 and bivalent v7180 was similar (EC50 8 pM vs 4 pM) but the OAA confers a 1.4-fold enhancement in efficacy.

These results show the OAA mediates equal or better efficacy than the corresponding bivalent antibody in different EGFR expressing cancer cells. Specifically, the monovalent antibody is expected to be similar to the bivalent counterpart in high EGFR expressing cells, but is expected to significantly enhance the efficacy in lower EGFR expressing cells without any significant loss of potency.

The reagents employed in the examples are generally commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents, and patent applications mentioned in this specification are herein incorporated by reference into the specification to the same extent as if each individual publication, patent or patent application was specifically and individually indicated to be incorporated herein by reference.

The invention claimed is:

1. A method of treating a subject having an epidermal growth factor receptor (EGFR)-expressing tumor, comprising: contacting the tumor with an effective amount of an isolated monovalent EGFR-binding construct comprising one antigen-binding polypeptide construct comprising a heavy chain variable domain and a light chain variable domain, or a single domain antibody coupled, with or without a linker, to a heterodimeric Fc, the Fc comprising two CH3 sequences comprising one or more asymmetric amino acid substitutions that promote formation of a heterodimeric Fc, wherein the antigen-binding polypeptide construct comprises three variable heavy chain CDRs as set forth in SEQ ID NOs:2, 3 and 4, and three variable light chain CDRs as set forth in SEQ ID NOs:6, 7, and 8, or wherein the antigen-binding polypeptide construct is a single domain antibody having three variable heavy chain CDRs as set forth in SEQ ID NOs:21, 22 and 23.

2. The method of claim 1, wherein the Fc is a heterodimeric human IgG1 Fc, wherein the antigen-binding polypeptide construct binds to an epitope located in the extracellular domain of EGFR, wherein the subject experiences less skin toxicity from the treatment compared to a subject treated with the isolated corresponding monospecific bivalent antigen-binding construct that binds or specifically binds EGFR, and wherein the tumor expresses a first level of cell surface EGFR that is equal to or less than a second level of cell surface EGFR of one or more of the following cell lines: A431, A549, BT474, CACO2, HCT116, JIMT1, MDA-MB-231, SKOV3, MCF7, or SKBR3.

3. The method according to claim 1, wherein the isolated monovalent EGFR-binding construct is OA-CTX (v4353) or OA-EG2 (v1323).

4. The method according to claim 1 wherein the monovalent EGFR-binding construct is afucosylated.

5. The method according to claim 1 wherein the monovalent EGFR-binding construct is conjugated to a drug, optionally wherein the drug is a maytansinoid.

6. The method according to claim 1, wherein a) the tumor expresses a first level of cell surface EGFR that is equal to or less than a second level of cell surface EGFR of one or more of the following cell lines: A431, A549, BT474, CACO2, HCT116, JIMT1, MDA-MB-231, SKOV3, MCF7, or SKBr3; b) the tumor expresses a median of $3.5\times10^6$ or less, $2.8\times10^6$ or less, $1.2\times10^6$ or less, $2.4\times10^5$ or less, $2.6\times10^5$ or less, or $4.2\times10^4$ or less EGFRs per cell, or c) wherein the tumor is an epidermal cell-derived cancer, a lung cancer, a breast cancer, a triple negative breast cancer, a ductal breast cancer, a gastric cancer, an ovarian cancer, a HER2+ cancer, glioblastoma, a cervical cancer, a renal cancer, an uterine cancer, or a colorectal cancer, optionally wherein the tumor is resistant or refractory to trastuzumab and/or pertuzumab and/or cetuximab.

7. The method according to claim 1 wherein a) the treatment results in shrinking the tumor, inhibiting the growth of the tumor, increasing time to progression of the tumor, prolonging disease-free survival of the subject, decreasing metastases, increasing the progression-free survival of the subject, or increasing the overall survival of a population of subjects, and/or b) wherein the subject is administered a fixed dose of the construct and experiences less skin toxicity from the treatment compared to a subject treated with a fixed dose of the corresponding isolated monospecific bivalent antigen-binding construct that binds or specifically binds EGFR, and wherein the fixed dose is determined on a molar basis, or the growth of the subject's keratinocytes is reduced less following treatment with a fixed dose of the construct compared to a subject treated with a fixed dose of the corresponding isolated monospecific bivalent antigen-binding construct that binds or specifically binds EGFR, and wherein the fixed dose is determined on a molar basis.

8. The method according to claim 1 wherein the method further comprises providing an additional agent, optionally wherein the additional agent binds HER2, or wherein the additional agent is pertuzumab or trastuzumab, optionally wherein the additional agent is a second isolated antigen binding construct, optionally wherein a) the second isolated antigen binding construct binds or specifically binds to HER2 or an extracellular domain of HER2, b) the second isolated antigen binding construct binds or specifically binds to ECD2 and/or ECD4 of HER2, or c) the second isolated antigen binding construct is an isolated monovalent antigen binding construct wherein the antigen-binding polypeptide construct of the second isolated antigen binding construct binds or specifically binds HER2 or an extracellular domain of HER2.

9. The method according to claim 5, wherein the maytansinoid is DM1.

10. The method according to claim 1, wherein the monovalent antigen-binding polypeptide construct comprises a VH sequence as set forth in SEQ ID NO:1 and a VL sequence as set forth in SEQ ID NO:5, or wherein the monovalent antigen-binding polypeptide construct comprises a VHH sequence as set forth in SEQ ID NO:20.

11. The method according to claim 1, wherein the isolated monovalent EGFR-binding construct blocks binding of EGF to EGFR on the tumor, blocks constitutive EGFR signaling in the tumor, or results in internalization of the isolated monovalent EGFR-binding construct.

12. The method of claim 1, wherein the Fc isotype is human IgG.

13. The method of claim 10, wherein the monovalent antigen-binding polypeptide construct comprises (1) a HC-1 sequence as set forth in SEQ ID NO:17, a HC-2 sequence as set forth in SEQ ID NO:18, and a LC sequence as set forth in SEQ ID NO:19; or (2) a HC-1 sequence as set forth in SEQ ID NO:30 and a HC-2 sequence as set forth in SEQ ID NO:31.

14. An isolated monovalent antigen-binding construct comprising:

one antigen-binding polypeptide construct comprising a heavy chain variable domain and a light chain variable domain, or a single domain antibody, wherein the monovalent antigen-binding polypeptide construct specifically binds epidermal growth factor receptor (EGFR), wherein the monovalent antigen-binding polypeptide construct comprises three variable heavy chain CDRs as set forth in SEQ ID NOs:2, 3 and 4, and three variable light chain CDRs as set forth in SEQ ID NOs:6, 7, and 8, or wherein the monovalent antigen-binding polypeptide construct is a single domain antibody having three variable heavy chain CDRs as set forth in SEQ ID NOs:21, 22 and 23; and a heterodimeric Fc, the Fc comprising two CH3 sequences comprising one or more asymmetric amino acid substitutions that promote formation of a heterodimeric Fc, wherein the Fc is coupled, with or without a linker, to the antigen-binding polypeptide.

15. The construct according to claim 14, wherein the monovalent antigen-binding polypeptide construct (1) comprises a VH sequence as set forth in SEQ ID NO:1 and a VL sequence as set forth in SEQ ID NO:5, or (2) comprises a VHH sequence as set forth in SEQ ID NO:20.

16. The construct of claim 14, wherein the Fc isotype is human IgG.

17. The construct of claim 15, wherein the monovalent antigen-binding polypeptide construct comprises (1) a HC-1 sequence as set forth in SEQ ID NO:17, a HC-2 sequence as set forth in SEQ ID NO:18, and a LC sequence as set forth in SEQ ID NO:19; or (2) a HC-1 sequence as set forth in SEQ ID NO:30 and a HC-2 sequence as set forth in SEQ ID NO:31.

18. A pharmaceutical composition comprising the isolated monovalent antigen-binding construct of claim 14 and a pharmaceutically acceptable carrier.

19. A vector or set of vectors comprising one or more polynucleotides encoding the isolated monovalent antigen-binding construct according to claim 14.

20. An isolated cell comprising one or more polynucleotides encoding the isolated monovalent antigen-binding construct according to claim 14.

21. A method of obtaining the isolated monovalent antigen-binding construct according to claim 14, the method comprising the steps of: (a) obtaining a host cell culture, wherein the host cell comprises one or more nucleic acid sequences encoding the antigen-binding construct; (b) culturing the host cell culture under conditions sufficient to express the isolated monovalent antigen-binding construct; and (c) recovering the antigen-binding construct from the host cell culture.

* * * * *

SEQUENCE LISTING

```
<160> NUMBER OF SEQ ID NOS: 70

<210> SEQ ID NO 1
<211> LENGTH: 119
<212> TYPE: PRT
<213> ORGANISM: Homo sapiens

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 2
<211> LENGTH: 10
<212> TYPE: PRT
<213> ORGANISM: Homo sapiens

<400> SEQUENCE: 2

Gly Phe Ser Leu Thr Asn Tyr Gly Val His
1               5                   10


<210> SEQ ID NO 3
<211> LENGTH: 7
<212> TYPE: PRT
<213> ORGANISM: Homo sapiens

<400> SEQUENCE: 3

Ile Trp Ser Gly Gly Asn Thr
```

1 5

<210> SEQ ID NO 4
<211> LENGTH: 11
<212> TYPE: PRT
<213> ORGANISM: Homo sapiens

<400> SEQUENCE: 4

Ala Leu Thr Tyr Tyr Asp Tyr Glu Phe Ala Tyr
1 5 10

<210> SEQ ID NO 5
<211> LENGTH: 107
<212> TYPE: PRT
<213> ORGANISM: Homo sapiens

<400> SEQUENCE: 5

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys
100 105

<210> SEQ ID NO 6
<211> LENGTH: 11
<212> TYPE: PRT
<213> ORGANISM: Homo sapiens

<400> SEQUENCE: 6

Arg Ala Ser Gln Ser Ile Gly Thr Asn Ile His
1 5 10

<210> SEQ ID NO 7
<211> LENGTH: 7
<212> TYPE: PRT
<213> ORGANISM: Homo sapiens

<400> SEQUENCE: 7

Tyr Ala Ser Glu Ser Ile Ser
1 5

<210> SEQ ID NO 8
<211> LENGTH: 9
<212> TYPE: PRT
<213> ORGANISM: Homo sapiens

<400> SEQUENCE: 8

Gln Gln Asn Asn Asn Trp Pro Thr Thr
1 5

<210> SEQ ID NO 9
<211> LENGTH: 107
<212> TYPE: PRT

<213> ORGANISM: Homo sapiens

<400> SEQUENCE: 9

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 10
<211> LENGTH: 98
<212> TYPE: PRT
<213> ORGANISM: Homo sapiens

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 11
<211> LENGTH: 23
<212> TYPE: PRT
<213> ORGANISM: Homo sapiens

<400> SEQUENCE: 11

```
Glu Pro Lys Ser Cys Asp Lys Thr His Thr Cys Pro Pro Cys Pro Ala
1               5                   10                  15

Pro Glu Leu Leu Gly Gly Pro
            20
```

<210> SEQ ID NO 12
<211> LENGTH: 23
<212> TYPE: PRT
<213> ORGANISM: Homo sapiens

<400> SEQUENCE: 12

```
Glu Pro Lys Ser Ser Asp Lys Thr His Thr Cys Pro Pro Cys Pro Ala
1               5                   10                  15

Pro Glu Leu Leu Gly Gly Pro
```

20

<210> SEQ ID NO 13
<211> LENGTH: 102
<212> TYPE: PRT
<213> ORGANISM: Homo sapiens

<400> SEQUENCE: 13

Ser Val Phe Leu Phe Pro Pro Lys Pro Lys Asp Thr Leu Met Ile Ser
1 5 10 15

Arg Thr Pro Glu Val Thr Cys Val Val Val Asp Val Ser His Glu Asp
20 25 30

Pro Glu Val Lys Phe Asn Trp Tyr Val Asp Gly Val Glu Val His Asn
35 40 45

Ala Lys Thr Lys Pro Arg Glu Glu Gln Tyr Asn Ser Thr Tyr Arg Val
50 55 60

Val Ser Val Leu Thr Val Leu His Gln Asp Trp Leu Asn Gly Lys Glu
65 70 75 80

Tyr Lys Cys Lys Val Ser Asn Lys Ala Leu Pro Ala Pro Ile Glu Lys
85 90 95

Thr Ile Ser Lys Ala Lys
100

<210> SEQ ID NO 14
<211> LENGTH: 102
<212> TYPE: PRT
<213> ORGANISM: Homo sapiens

<400> SEQUENCE: 14

Ser Val Phe Leu Phe Pro Pro Lys Pro Lys Asp Thr Leu Met Ile Ser
1 5 10 15

Arg Thr Pro Glu Val Thr Cys Val Val Val Asp Val Ser His Glu Asp
20 25 30

Pro Glu Val Lys Phe Asn Trp Tyr Val Asp Gly Val Glu Val His Asn
35 40 45

Ala Lys Thr Lys Pro Arg Glu Glu Gln Tyr Asn Ser Thr Tyr Arg Val
50 55 60

Val Ser Val Leu Thr Val Leu His Gln Asp Trp Leu Asn Gly Lys Glu
65 70 75 80

Tyr Lys Cys Lys Val Ser Asn Lys Ala Leu Pro Ala Pro Ile Glu Lys
85 90 95

Thr Ile Ser Lys Ala Lys
100

<210> SEQ ID NO 15
<211> LENGTH: 107
<212> TYPE: PRT
<213> ORGANISM: Homo sapiens

<400> SEQUENCE: 15

Gly Gln Pro Arg Glu Pro Gln Val Tyr Val Tyr Pro Pro Ser Arg Asp
1 5 10 15

Glu Leu Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

```
Ala Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 16
<211> LENGTH: 107
<212> TYPE: PRT
<213> ORGANISM: Homo sapiens

<400> SEQUENCE: 16

Gly Gln Pro Arg Glu Pro Gln Val Tyr Val Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Leu Thr Trp Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 17
<211> LENGTH: 449
<212> TYPE: PRT
<213> ORGANISM: Homo sapiens

<400> SEQUENCE: 17

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Val
340 345 350

Tyr Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Ala Leu Val Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 18
<211> LENGTH: 232
<212> TYPE: PRT
<213> ORGANISM: Homo sapiens

<400> SEQUENCE: 18

Glu Pro Lys Ser Ser Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 19
<211> LENGTH: 214
<212> TYPE: PRT
<213> ORGANISM: Homo sapiens

<400> SEQUENCE: 19

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 20
<211> LENGTH: 125
<212> TYPE: PRT
<213> ORGANISM: Homo sapiens

<400> SEQUENCE: 20

```
Gln Val Lys Leu Glu Glu Ser Gly Gly Gly Leu Val Gln Ala Gly Asp
1               5                   10                  15

Ser Leu Arg Val Ser Cys Ala Ala Ser Gly Arg Asp Phe Ser Asp Tyr
            20                  25                  30

Val Met Gly Trp Phe Arg Gln Ala Pro Gly Lys Glu Arg Glu Phe Val
        35                  40                  45

Ala Ala Ile Ser Arg Asn Gly Leu Thr Thr Arg Tyr Ala Asp Ser Val
    50                  55                  60

Lys Gly Arg Phe Thr Ile Ser Arg Asp Asn Asp Lys Asn Met Val Tyr
65                  70                  75                  80

Leu Gln Met Asn Ser Leu Lys Pro Glu Asp Thr Ala Val Tyr Tyr Cys
                85                  90                  95

Ala Val Asn Ser Ala Gly Thr Tyr Val Ser Pro Arg Ser Arg Glu Tyr
            100                 105                 110

Asp Tyr Trp Gly Gln Gly Thr Gln Val Thr Val Ser Ser
        115                 120                 125
```

<210> SEQ ID NO 21
<211> LENGTH: 10
<212> TYPE: PRT
<213> ORGANISM: Homo sapiens

<400> SEQUENCE: 21

```
Gly Arg Asp Phe Ser Asp Tyr Val Met Gly
1               5                   10
```

<210> SEQ ID NO 22
<211> LENGTH: 8
<212> TYPE: PRT
<213> ORGANISM: Homo sapiens

<400> SEQUENCE: 22

```
Ile Ser Arg Asn Gly Leu Thr Thr
1               5
```

<210> SEQ ID NO 23
<211> LENGTH: 16
<212> TYPE: PRT
<213> ORGANISM: Homo sapiens

<400> SEQUENCE: 23

```
Asn Ser Ala Gly Thr Tyr Val Ser Pro Arg Ser Arg Glu Tyr Asp Tyr
1               5                   10                  15
```

<210> SEQ ID NO 24
<211> LENGTH: 23
<212> TYPE: PRT
<213> ORGANISM: Homo sapiens

<400> SEQUENCE: 24

```
Glu Pro Lys Ser Cys Asp Lys Thr His Thr Cys Pro Pro Cys Pro Ala
1               5                   10                  15

Pro Glu Leu Leu Gly Gly Pro
            20
```

<210> SEQ ID NO 25
<211> LENGTH: 23
<212> TYPE: PRT
<213> ORGANISM: Homo sapiens

<400> SEQUENCE: 25

```
Glu Pro Lys Ser Ser Asp Lys Thr His Thr Cys Pro Pro Cys Pro Ala
1               5                   10                  15

Pro Glu Leu Leu Gly Gly Pro
            20
```

<210> SEQ ID NO 26
<211> LENGTH: 102
<212> TYPE: PRT
<213> ORGANISM: Homo sapiens

<400> SEQUENCE: 26

```
Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser His Glu Asp
            20                  25                  30

Pro Glu Val Lys Phe Asn Trp Tyr Val Asp Gly Val Glu Val His Asn
        35                  40                  45

Ala Lys Thr Lys Pro Arg Glu Glu Gln Tyr Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Ala Leu Pro Ala Pro Ile Glu Lys
                85                  90                  95

Thr Ile Ser Lys Ala Lys
            100
```

<210> SEQ ID NO 27
<211> LENGTH: 102
<212> TYPE: PRT
<213> ORGANISM: Homo sapiens

<400> SEQUENCE: 27

```
Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser His Glu Asp
            20                  25                  30

Pro Glu Val Lys Phe Asn Trp Tyr Val Asp Gly Val Glu Val His Asn
        35                  40                  45

Ala Lys Thr Lys Pro Arg Glu Glu Gln Tyr Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Ala Leu Pro Ala Pro Ile Glu Lys
                85                  90                  95

Thr Ile Ser Lys Ala Lys
            100
```

<210> SEQ ID NO 28
<211> LENGTH: 107
<212> TYPE: PRT
<213> ORGANISM: Homo sapiens

<400> SEQUENCE: 28

```
Gly Gln Pro Arg Glu Pro Gln Val Tyr Val Tyr Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Ala Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 29
<211> LENGTH: 107
<212> TYPE: PRT
<213> ORGANISM: Homo sapiens

<400> SEQUENCE: 29

Gly Gln Pro Arg Glu Pro Gln Val Tyr Val Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Leu Thr Trp Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 30

<400> SEQUENCE: 30

000


<210> SEQ ID NO 31
<211> LENGTH: 232
<212> TYPE: PRT
<213> ORGANISM: Homo sapiens

<400> SEQUENCE: 31

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 32
<211> LENGTH: 450
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 33
<211> LENGTH: 232
<212> TYPE: PRT
<213> ORGANISM: Homo sapiens

<400> SEQUENCE: 33

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125
```

```
Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 34
<211> LENGTH: 214
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 35
<211> LENGTH: 448
<212> TYPE: PRT
<213> ORGANISM: Homo sapiens

<400> SEQUENCE: 35
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Tyr Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
```

```
            420                 425                 430

Ala Leu His Asn His Tyr Thr Gln Lys Ser Leu Ser Leu Ser Pro Gly
        435                 440                 445


<210> SEQ ID NO 36
<211> LENGTH: 232
<212> TYPE: PRT
<213> ORGANISM: Homo sapiens

<400> SEQUENCE: 36

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 37
<211> LENGTH: 214
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 38
<211> LENGTH: 607
<212> TYPE: PRT
<213> ORGANISM: Homo sapiens

<400> SEQUENCE: 38

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220
```

```
Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn
        595                 600                 605
```

<210> SEQ ID NO 39
<211> LENGTH: 621
<212> TYPE: PRT
<213> ORGANISM: Homo sapiens

<400> SEQUENCE: 39

-continued

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415
```

```
Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser
    610                 615                 620


<210> SEQ ID NO 40
<211> LENGTH: 217
<212> TYPE: PRT
<213> ORGANISM: Homo sapiens

<400> SEQUENCE: 40

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175
```

```
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 41
<211> LENGTH: 357
<212> TYPE: DNA
<213> ORGANISM: Homo sapiens

<400> SEQUENCE: 41

caggtccagc tgaagcagag cggaccagga ctggtgcagc cttcacagag cctgtccatc     60

acttgcaccg tgtccggatt ctctctgaca aactacggag tccactgggt gcgacagagt    120

ccaggaaaag gcctggagtg gctgggcgtg atctggagcg gagggaacac tgactataat    180

actcctttta ccagtcggct gtcaattaac aaggataact ctaagagtca ggtgttcttt    240

aagatgaaca gcctgcagtc caatgacaca gctatctact attgcgctag agcactgact    300

tactatgatt acgagttcgc atattggggg cagggaacac tggtcactgt gtctgcc       357


<210> SEQ ID NO 42
<211> LENGTH: 30
<212> TYPE: DNA
<213> ORGANISM: Homo sapiens

<400> SEQUENCE: 42

ggattctctc tgacaaacta cggagtccac                                      30


<210> SEQ ID NO 43
<211> LENGTH: 21
<212> TYPE: DNA
<213> ORGANISM: Homo sapiens

<400> SEQUENCE: 43

atctggagcg gagggaacac t                                               21


<210> SEQ ID NO 44
<211> LENGTH: 33
<212> TYPE: DNA
<213> ORGANISM: Homo sapiens

<400> SEQUENCE: 44

gcactgactt actatgatta cgagttcgca tat                                  33


<210> SEQ ID NO 45
<211> LENGTH: 321
<212> TYPE: DNA
<213> ORGANISM: Homo sapiens

<400> SEQUENCE: 45

gacatcctgc tgactcagag cccagtgatc ctgtcagtca gcccaggaga gcgggtgtcc     60

ttctcttgca gagcaagtca gtcaatcgga acaaatattc actggtacca gcagaggact    120

aacggctccc ctcgcctgct gattaagtat gctagcgaat ccatctctgg cattccatct    180

cggttcagtg gctcagggag cggaacagac tttactctgt ccatcaattc tgtggagagt    240

gaagacattg ccgattacta ttgccagcag aacaataact ggcccaccac attcggcgct    300

gggaccaagc tggagctgaa a                                              321
```

<210> SEQ ID NO 46
<211> LENGTH: 33
<212> TYPE: DNA
<213> ORGANISM: Homo sapiens

<400> SEQUENCE: 46
agagcaagtc agtcaatcgg aacaaatatt cac 33

<210> SEQ ID NO 47
<211> LENGTH: 21
<212> TYPE: DNA
<213> ORGANISM: Homo sapiens

<400> SEQUENCE: 47
tatgctagcg aatccatctc t 21

<210> SEQ ID NO 48
<211> LENGTH: 27
<212> TYPE: DNA
<213> ORGANISM: Homo sapiens

<400> SEQUENCE: 48
cagcagaaca ataactggcc caccaca 27

<210> SEQ ID NO 49
<211> LENGTH: 321
<212> TYPE: DNA
<213> ORGANISM: Homo sapiens

<400> SEQUENCE: 49
cgaacagtgg ccgctccttc tgtcttcatc tttcccccta gtgacgaaca gctgaaaagc 60
ggcacagcct ccgtggtctg tctgctgaat aacttttacc caagagaggc aaaggtgcag 120
tggaaagtcg ataatgccct gcagtcaggg aacagccagg agtccgtgac tgaacaggac 180
tctaaggata gtacctattc actgagctcc actctgaccc tgtccaaagc tgattacgag 240
aagcacaaag tgtatgcatg cgaagtcacc catcaggggc tgtctagtcc cgtgacaaag 300
agctttaacc ggggagagtg t 321

<210> SEQ ID NO 50
<211> LENGTH: 294
<212> TYPE: DNA
<213> ORGANISM: Homo sapiens

<400> SEQUENCE: 50
gctagtacca agggaccaag cgtgtttcca ctggcaccaa gctccaaatc aaccagcgga 60
ggcacagcag ccctgggatg tctggtgaag gactacttcc cagagcccgt cacagtgtca 120
tggaacagcg gcgcactgac atccggggtc catacttttc ctgccgtgct gcagtctagt 180
ggcctgtact ctctgtcaag cgtggtcacc gtgccatcct ctagtctggg gacacagact 240
tatatctgca acgtgaatca caagccttcc aatacaaaag tcgacaagaa agtg 294

<210> SEQ ID NO 51
<211> LENGTH: 69
<212> TYPE: DNA
<213> ORGANISM: Homo sapiens

<400> SEQUENCE: 51
gaaccaaagt cttgtgataa aacccataca tgcccacctt gtcctgcacc agagctgctg 60
ggaggacca 69

<210> SEQ ID NO 52
<211> LENGTH: 69
<212> TYPE: DNA
<213> ORGANISM: Homo sapiens

<400> SEQUENCE: 52
gaacctaaaa gcagcgacaa gacccacaca tgcccccctt gtccagctcc agaactgctg 60
ggaggacca 69

<210> SEQ ID NO 53
<211> LENGTH: 306
<212> TYPE: DNA
<213> ORGANISM: Homo sapiens

<400> SEQUENCE: 53
tccgtgttcc tgtttccacc caagcccaaa gacaccctga tgatttcccg cactccagaa 60
gtcacctgcg tggtcgtgga cgtgtctcac gaggaccccg aagtcaagtt caactggtac 120
gtggatggcg tcgaggtgca taatgccaag acaaaaccac gggaggaaca gtacaatagt 180
acttatagag tcgtgtcagt cctgaccgtg ctgcaccagg actggctgaa cggcaaggag 240
tataagtgca aagtgagcaa taaggccctg cccgctccta tcgagaaaac cattagcaag 300
gcaaaa 306

<210> SEQ ID NO 54
<211> LENGTH: 306
<212> TYPE: DNA
<213> ORGANISM: Homo sapiens

<400> SEQUENCE: 54
agcgtgttcc tgtttccacc caagcccaaa gatacactga tgatcagccg aactcccgag 60
gtcacctgcg tggtcgtgga cgtgtcccac gaggaccccg aagtcaagtt caactggtac 120
gtggacggcg tcgaagtgca taatgcaaag actaaaccac gggaggaaca gtacaactct 180
acatatagag tcgtgagtgt cctgactgtg ctgcatcagg attggctgaa cggcaaagag 240
tataagtgca aagtgtctaa taaggccctg cctgctccaa tcgagaaaac tattagtaag 300
gcaaaa 306

<210> SEQ ID NO 55
<211> LENGTH: 321
<212> TYPE: DNA
<213> ORGANISM: Homo sapiens

<400> SEQUENCE: 55
gggcagccta gggaaccaca ggtctacgtg tatcctccat cacgcgacga gctgaccaag 60
aaccaggtca gcctgacatg tctggtgaaa gggttttacc cctctgatat cgctgtggag 120
tgggaaagta atggacagcc tgaaaacaat tataagacca cacccccctgt gctggactcc 180 gatggatctt tcgccctggt cagcaagctg actgtggata aatccaggtg gcagcagggc 240
aacgtctttt cctgttctgt gatgcatgag gctctgcaca atcattacac ccagaagagt 300
ctgtcactga gccctggcaa a 321

<210> SEQ ID NO 56
<211> LENGTH: 321
<212> TYPE: DNA
<213> ORGANISM: Homo sapiens

<400> SEQUENCE: 56
gggcagccca gggaacctca ggtctacgtg ctgcctccaa gtcgcgacga gctgaccaag 60
aaccaggtct cactgctgtg tctggtgaaa ggattctatc cttccgatat tgccgtggag 120
tgggaatcta atggccagcc agagaacaat tacctgacct ggccccctgt gctggacagc 180
gatgggtcct tctttctgta ttcaaagctg acagtggaca aaagcagatg gcagcaggga 240
aacgtcttta gctgttccgt gatgcacgaa gccctgcaca atcattacac ccagaagtct 300
ctgagtctgt cacctggcaa a 321

<210> SEQ ID NO 57
<211> LENGTH: 696
<212> TYPE: DNA
<213> ORGANISM: Homo sapiens

<400> SEQUENCE: 57
gaacctaaaa gcagcgacaa gacccacaca tgcccccctt gtccagctcc agaactgctg 60
ggaggaccaa gcgtgttcct gtttccaccc aagcccaaag atacactgat gatcagccga 120
actcccgagg tcacctgcgt ggtcgtggac gtgtcccacg aggaccccga agtcaagttc 180
aactggtacg tggacggcgt cgaagtgcat aatgcaaaga ctaaaccacg ggaggaacag 240
tacaactcta catatagagt cgtgagtgtc ctgactgtgc tgcatcagga ttggctgaac 300
ggcaaagagt ataagtgcaa agtgtctaat aaggccctgc ctgctccaat cgagaaaact 360
attagtaagg caaaagggca gcccagggaa cctcaggtct acgtgctgcc tccaagtcgc 420
gacgagctga ccaagaacca ggtctcactg ctgtgtctgg tgaaaggatt ctatccttcc 480
gatattgccg tggagtggga atctaatggc cagccagaga acaattacct gacctggccc 540
cctgtgctgg acagcgatgg gtccttcttt ctgtattcaa agctgacagt ggacaaaagc 600
agatggcagc agggaaacgt ctttagctgt tccgtgatgc acgaagccct gcacaatcat 660
tacacccaga agtctctgag tctgtcacct ggcaaa 696

<210> SEQ ID NO 58
<211> LENGTH: 642
<212> TYPE: DNA
<213> ORGANISM: Homo sapiens

<400> SEQUENCE: 58
gacatcctgc tgactcagag cccagtgatc ctgtcagtca gcccaggaga gcgggtgtcc 60
ttctcttgca gagcaagtca gtcaatcgga acaaatattc actggtacca gcagaggact 120
aacggctccc ctcgcctgct gattaagtat gctagcgaat ccatctctgg cattccatct 180
cggttcagtg gctcagggag cggaacagac tttactctgt ccatcaattc tgtggagagt 240
gaagacattg ccgattacta ttgccagcag aacaataact ggcccaccac attcggcgct 300
gggaccaagc tggagctgaa acgaacagtg gccgctcctt ctgtcttcat ctttcccccct 360 agtgacgaac agctgaaaag cggcacagcc tccgtggtct gtctgctgaa taacttttac 420
ccaagagagg caaaggtgca gtggaaagtc gataatgccc tgcagtcagg gaacagccag 480
gagtccgtga ctgaacagga ctctaaggat agtacctatt cactgagctc cactctgacc 540
ctgtccaaag ctgattacga gaagcacaaa gtgtatgcat gcgaagtcac ccatcagggg 600
ctgtctagtc ccgtgacaaa gagctttaac cggggagagt gt 642

<210> SEQ ID NO 59

<211> LENGTH: 69
<212> TYPE: DNA
<213> ORGANISM: Homo sapiens

<400> SEQUENCE: 59
gaacctaaaa gcagcgacaa gacccacaca tgcccccctt gtccagctcc agaactgctg 60
ggaggacca 69

<210> SEQ ID NO 60
<211> LENGTH: 306
<212> TYPE: DNA
<213> ORGANISM: Homo sapiens

<400> SEQUENCE: 60
agcgtgttcc tgtttccacc caagcccaaa gatacactga tgatcagccg aactcccgag 60
gtcacctgcg tggtcgtgga cgtgtcccac gaggaccccg aagtcaagtt caactggtac 120
gtggacggcg tcgaagtgca taatgcaaag actaaaccac gggaggaaca gtacaactct 180
acatatagag tcgtgagtgt cctgactgtg ctgcatcagg attggctgaa cggcaaagag 240
tataagtgca aagtgtctaa taaggccctg cctgctccaa tcgagaaaac tattagtaag 300
gcaaaa 306

<210> SEQ ID NO 61
<211> LENGTH: 321
<212> TYPE: DNA
<213> ORGANISM: Homo sapiens

<400> SEQUENCE: 61
gggcagccca gggaacctca ggtctacgtg ctgcctccaa gtcgcgacga gctgaccaag 60
aaccaggtct cactgctgtg tctggtgaaa ggattctatc cttccgatat tgccgtggag 120
tgggaatcta atggccagcc agagaacaat tacctgacct ggcccccctgt gctggacagc 180 gatgggtcct tctttctgta ttcaaagctg acagtggaca aaagcagatg gcagcaggga 240
aacgtcttta gctgttccgt gatgcacgaa gccctgcaca atcattacac ccagaagtct 300
ctgagtctgt cacctggcaa a 321

<210> SEQ ID NO 62
<211> LENGTH: 696
<212> TYPE: DNA
<213> ORGANISM: Homo sapiens

<400> SEQUENCE: 62
gaacctaaaa gcagcgacaa gacccacaca tgcccccctt gtccagctcc agaactgctg 60
ggaggaccaa gcgtgttcct gtttccaccc aagcccaaag atacactgat gatcagccga 120
actcccgagg tcacctgcgt ggtcgtggac gtgtcccacg aggaccccga agtcaagttc 180
aactggtacg tggacggcgt cgaagtgcat aatgcaaaga ctaaaccacg ggaggaacag 240
tacaactcta catatagagt cgtgagtgtc ctgactgtgc tgcatcagga ttggctgaac 300
ggcaaagagt ataagtgcaa agtgtctaat aaggccctgc ctgctccaat cgagaaaact 360
attagtaagg caaaagggca gcccagggaa cctcaggtct acgtgctgcc tccaagtcgc 420
gacgagctga ccaagaacca ggtctcactg ctgtgtctgg tgaaaggatt ctatccttcc 480
gatattgccg tggagtggga atctaatggc cagccagaga acaattacct gacctggccc 540
cctgtgctgg acagcgatgg gtccttcttt ctgtattcaa agctgacagt ggacaaaagc 600
agatggcagc agggaaacgt ctttagctgt tccgtgatgc acgaagccct gcacaatcat 660
tacacccaga agtctctgag tctgtcacct ggcaaa 696

<210> SEQ ID NO 63
<211> LENGTH: 1350
<212> TYPE: DNA
<213> ORGANISM: Homo sapiens

<400> SEQUENCE: 63
gaagtccagc tggtcgaaag cggaggagga ctggtgcagc caggagggtc tctgcgactg 60
agttgcgccg cttcaggctt caacatcaag gacacctaca ttcactgggt gcgccaggct 120
cctggaaaag gcctggagtg ggtggcacga atctatccaa ctaatggata cacccggtat 180
gcagacagcg tgaagggccg gttcaccatt agcgcagata catccaaaaa cactgcctac 240
ctgcagatga acagcctgcg agccgaagat actgctgtgt actattgcag tcggtgggga 300
ggcgacggct tctacgctat ggattattgg gggcagggaa ccctggtcac agtgagctcc 360
gcatctacaa aggggcctag tgtgtttcca ctggcccccct ctagtaaatc cacctctggg 420
ggaacagcag ccctgggatg tctggtgaag gactatttcc cagagcccgt cactgtgagt 480
tggaactcag gcgccctgac atccggggtc catacttttc ctgctgtgct gcagtcaagc 540
ggcctgtact ctctgtcctc tgtggtcacc gtgccaagtt caagcctggg gactcagacc 600
tatatctgca acgtgaatca caagccaagc aatacaaaag tcgacaagaa agtggaaccc 660
aagagctgtg ataaaacaca tacttgcccc ccttgtcctg caccagagct gctgggagga 720
ccatccgtgt tcctgtttcc acccaagcct aaagacaccc tgatgatttc caggactcca 780
gaagtcacct gcgtggtcgt ggacgtgtct cacgaggacc ccgaagtcaa gttcaactgg 840
tacgtggatg gcgtcgaggt gcataatgcc aagacaaaac ccagggagga acagtacaac 900
tcaacttatc gcgtcgtgag cgtcctgacc gtgctgcacc aggactggct gaacggcaag 960
gagtataagt gcaaagtgag caataaggct ctgcccgcac ctatcgagaa aaccattagc 1020
aaggccaaag ggcagcctag agaaccacag gtctacgtgt atcctccaag cagggacgag 1080
ctgaccaaga accaggtctc cctgacatgt ctggtgaaag ggttttaccc cagtgatatc 1140
gctgtggagt gggaatcaaa tggacagcct gaaaacaatt ataagaccac accccctgtg 1200
ctggacagcg atggcagctt cgctctggtc tccaagctga ctgtggataa atctcggtgg 1260
cagcagggca acgtctttag ttgttcagtg atgcatgagg cactgcacaa tcattacacc 1320
cagaagagcc tgtccctgtc tcccggcaaa 1350

<210> SEQ ID NO 64
<211> LENGTH: 696
<212> TYPE: DNA
<213> ORGANISM: Homo sapiens

<400> SEQUENCE: 64
gaacctaaaa gcagcgacaa gacccacaca tgcccccctt gtccagctcc agaactgctg 60
ggaggaccaa gcgtgttcct gtttccaccc aagcccaaag atacactgat gatcagccga 120
actcccgagg tcacctgcgt ggtcgtggac gtgtcccacg aggaccccga agtcaagttc 180
aactggtacg tggacggcgt cgaagtgcat aatgcaaaga ctaaaccacg ggaggaacag 240
tacaactcta catatagagt cgtgagtgtc ctgactgtgc tgcatcagga ttggctgaac 300
ggcaaagagt ataagtgcaa agtgtctaat aaggccctgc ctgctccaat cgagaaaact 360
attagtaagg caaaagggca gcccagggaa cctcaggtct acgtgctgcc tccaagtcgc 420
gacgagctga ccaagaacca ggtctcactg ctgtgtctgg tgaaaggatt ctatccttcc 480
gatattgccg tggagtggga atctaatggc cagccagaga acaattacct gacctggccc 540
cctgtgctgg acagcgatgg gtccttcttt ctgtattcaa agctgacagt ggacaaaagc 600
agatggcagc agggaaacgt ctttagctgt tccgtgatgc acgaagccct gcacaatcat 660
tacacccaga agtctctgag tctgtcacct ggcaaa 696

<210> SEQ ID NO 65
<211> LENGTH: 642
<212> TYPE: DNA
<213> ORGANISM: Homo sapiens

<400> SEQUENCE: 65
gatattcaga tgacccagtc ccctagctcc ctgtccgctt ctgtgggcga cagggtcact 60
atcacctgcc gcgcatctca ggatgtgaac accgcagtcg cctggtacca gcagaagcct 120
gggaaagctc caaagctgct gatctacagt gcatcattcc tgtattcagg agtgcccagc 180
cggtttagcg gcagcagatc tggcaccgac ttcacactga ctatctctag tctgcagcct 240
gaggattttg ccacatacta ttgccagcag cactatacca cacccctac tttcggccag 300 gggaccaaag tggagatcaa gcgaactgtg gccgctccaa gtgtcttcat ttttccaccc 360
agcgacgaac agctgaaatc cggcacagct tctgtggtct gtctgctgaa caacttctac 420
cccagagagg ccaaagtgca gtggaaggtc gataacgctc tgcagagtgg caacagccag 480
gagagcgtga cagaacagga ctccaaagat tctacttata gtctgtcaag caccctgaca 540
ctgagcaagg cagactacga aaagcataaa gtgtatgcct gtgaggtgac ccatcagggg 600
ctgtcttctc ccgtgaccaa gtctttcaac cgaggcgaat gt 642

<210> SEQ ID NO 66
<211> LENGTH: 1344
<212> TYPE: DNA
<213> ORGANISM: Homo sapiens

<400> SEQUENCE: 66
gaagtgcagc tggtcgaatc tggaggagga ctggtgcagc caggagggtc cctgcgcctg 60
tcttgcgccg ctagtggctt cacttttacc gactacacca tggattgggt gcgacaggca 120
cctggaaagg gcctggagtg ggtcgccgat gtgaacccaa atagcggagg ctccatctac 180
aaccagcggt tcaagggccg gttcaccctg tcagtggacc ggagcaaaaa caccctgtat 240
ctgcagatga atagcctgcg agccgaagat actgctgtgt actattgcgc ccggaatctg 300
gggccctcct tctactttga ctattggggg cagggaactc tggtcaccgt gagctccgcc 360
tccaccaagg gaccttctgt gttcccactg gctccctcta gtaaatccac atctggggga 420
actgcagccc tgggctgtct ggtgaaggac tacttcccag agcccgtcac agtgtcttgg 480
aacagtggcg ctctgacttc tggggtccac acctttcctg cagtgctgca gtcaagcggg 540
ctgtacagcc tgtcctctgt ggtcaccgtg ccaagttcaa gcctgggaac acagacttat 600
atctgcaacg tgaatcacaa gccatccaat acaaaagtcg acaagaaagt ggaacccaag 660
tcttgtgata aaacccatac atgccccccct tgtcctgcac cagagctgct gggaggacca 720
agcgtgttcc tgtttccacc caagcctaaa gatacactga tgattagtag gaccccagaa 780
gtcacatgcg tggtcgtgga cgtgagccac gaggaccccg aagtcaagtt taactggtac 840
gtggacggcg tcgaggtgca taatgccaag actaaaccca gggaggaaca gtacaacagt 900
acctatcgcg tcgtgtcagt cctgacagtg ctgcatcagg attggctgaa cgggaaagag 960

-continued

```
tataagtgca aagtgagcaa taaggctctg cccgcaccta tcgagaaaac aatttccaag   1020

gcaaaaggac agcctagaga accacaggtg tacgtgtatc ctccatcaag ggatgagctg   1080

acaaagaacc aggtcagcct gacttgtctg gtgaaaggat tctatccctc tgacattgct   1140

gtggagtggg aaagtaatgg ccagcctgag aacaattaca agaccacacc ccctgtgctg   1200

gactcagatg gcagcttcgc gctggtgagc aagctgaccg tcgacaaatc ccggtggcag   1260

caggggaatg tgtttagttg ttcagtcatg cacgaggcac tgcacaacca ttacacccag   1320

aagtcactgt cactgtcacc aggg                                          1344
```

```
<210> SEQ ID NO 67
<211> LENGTH: 696
<212> TYPE: DNA
<213> ORGANISM: Homo sapiens

<400> SEQUENCE: 67

gaacctaaaa gcagcgacaa gacccacaca tgcccccctt gtccagctcc agaactgctg     60

ggaggaccaa gcgtgttcct gtttccaccc aagcccaaag atacactgat gatcagccga    120

actcccgagg tcacctgcgt ggtcgtggac gtgtcccacg aggaccccga agtcaagttc    180

aactggtacg tggacggcgt cgaagtgcat aatgcaaaga ctaaaccacg ggaggaacag    240

tacaactcta catatagagt cgtgagtgtc ctgactgtgc tgcatcagga ttggctgaac    300

ggcaaagagt ataagtgcaa agtgtctaat aaggccctgc ctgctccaat cgagaaaact    360

attagtaagg caaaagggca gcccagggaa cctcaggtct acgtgctgcc tccaagtcgc    420

gacgagctga ccaagaacca ggtctcactg ctgtgtctgg tgaaaggatt ctatccttcc    480

gatattgccg tggagtggga atctaatggc cagccagaga acaattacct gacctggccc    540

cctgtgctgg acagcgatgg gtccttcttt ctgtattcaa agctgacagt ggacaaaagc    600

agatggcagc agggaaacgt ctttagctgt tccgtgatgc acgaagccct gcacaatcat    660

tacacccaga agtctctgag tctgtcacct ggcaaa                              696
```

```
<210> SEQ ID NO 68
<211> LENGTH: 642
<212> TYPE: DNA
<213> ORGANISM: Homo sapiens

<400> SEQUENCE: 68

gatattcaga tgacccagtc cccaagctcc ctgagtgcct cagtgggcga ccgagtcacc     60

atcacatgca aggcttccca ggatgtgtct attggagtcg catggtacca gcagaagcca    120

ggcaaagcac ccaagctgct gatctatagc gcctcctacc ggtataccgg cgtgccctct    180

agattctctg gcagtgggtc aggaacagac tttactctga ccatctctag tctgcagcct    240

gaggatttcg ctacctacta ttgccagcag tactatatct acccatatac ctttggccag    300

gggacaaaag tggagatcaa gaggactgtg gccgctccct ccgtcttcat ttttcccccct    360

tctgacgaac agctgaaaag tggcacagcc agcgtggtct gtctgctgaa caatttctac    420

cctcgcgaag ccaaagtgca gtggaaggtc gataacgctc tgcagagcgg caacagccag    480

gagtctgtga ctgaacagga cagtaaagat tcaacctata gcctgtcaag cacactgact    540

ctgagcaagg cagactacga gaagcacaaa gtgtatgcct gcgaagtcac acatcagggg    600

ctgtcctctc ctgtgactaa gagctttaac agaggagagt gt                       642
```

```
<210> SEQ ID NO 69
```

-continued

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Lys Pro Arg Glu Glu Gln Tyr Asn Ser Thr Tyr Arg
1               5                   10


<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Glu Gln Tyr Asn Ser Thr Tyr Arg
1               5
```